United States Patent
Marino et al.

(10) Patent No.: US 9,534,243 B2
(45) Date of Patent: Jan. 3, 2017

(54) NUCLEOTIDE ANALOGS AND PROCESS FOR MAKING SAME ENZYME

(71) Applicants: John P. Marino, Silver Spring, MD (US); Zvi Kelman, Gaithersburg, MD (US); Jerard Hurwitz, New York, NY (US); Gary G. Giulian, Gaithersburg, MD (US)

(72) Inventors: John P. Marino, Silver Spring, MD (US); Zvi Kelman, Gaithersburg, MD (US); Jerard Hurwitz, New York, NY (US); Gary G. Giulian, Gaithersburg, MD (US)

(73) Assignees: THE UNITED STATES OF AMERICA, AS REPRESENTED BY THE SECRETARY OF COMMERCE, Washington, DC (US); MEMORIAL SLOAN KETTERING CANCER CENTER, New York, NY (US); UNIVERSITY OF MARYLAND, College Park, MD (US)

( * ) Notice: Subject to any disclaimer, the term of this patent is extended or adjusted under 35 U.S.C. 154(b) by 541 days.

(21) Appl. No.: 14/174,981

(22) Filed: Feb. 7, 2014

(65) Prior Publication Data
US 2014/0170711 A1 Jun. 19, 2014

Related U.S. Application Data

(60) Provisional application No. 61/761,896, filed on Feb. 7, 2013.

(51) Int. Cl.
| | |
|---|---|
| C12P 21/06 | (2006.01) |
| C12P 19/32 | (2006.01) |
| C07H 19/10 | (2006.01) |
| C07H 19/207 | (2006.01) |
| C12P 19/30 | (2006.01) |

(52) U.S. Cl.
CPC ............... *C12P 19/32* (2013.01); *C07H 19/10* (2013.01); *C07H 19/207* (2013.01); *C12P 19/305* (2013.01); *C12Y 207/07* (2013.01); *Y02P 20/52* (2015.11)

(58) Field of Classification Search
CPC .................................................... C12N 21/06
See application file for complete search history.

(56) References Cited

U.S. PATENT DOCUMENTS

| | | | |
|---|---|---|---|
| 5,594,110 A | 1/1997 | Fiume | |
| 6,399,335 B1 | 6/2002 | Kao | |
| 6,914,052 B2 | 7/2005 | McLaughlin | |
| 7,211,647 B2 * | 5/2007 | Ishino | C12N 9/1252 435/69.1 |
| 2006/0248617 A1 * | 11/2006 | Imanaka | C07K 14/195 800/289 |
| 2012/0108533 A1 | 5/2012 | Herdewijn | |

FOREIGN PATENT DOCUMENTS

WO  2008104408  4/2008

OTHER PUBLICATIONS

Wu et al. 2003. Riboviron, viramidine, and adenosine-deaminase-catalyzed drug activation: implication for nucleoside prodrug desgin. J. Antimicoribal chemotherapy. 52(4): 543-546.*
Malet-Martino et al. (2002. Clinical studies of three oral prodtugs of 5-fluorouracil (capecitabine, UFT, S-1): A review. The Oncologist. 7:288-323.*
Tobias et al. 2001. Synthesis and biological studies of novel nucleoside phophoramidate prodrugs. J. Med. Chem. 44:4475-4480.*
Sundararaj et al. (2004. The cyberCell Database (CCDB): a comprehensive, self-updating, relational database to coordinate and facilitate in silico modeling of *Escherichia coli*. Nucleic Acids Res. 32:D293-D295.*
Regni et al. 2009. How the MccB bacterial ancestor of ubiquitin E1 inititates biosynthesis of the microcin C7 antibiotic. EMBO J 28(13): 1953-1964.*
Franchetti et al. 1994. Synthesis and evaluation of the anti-HIV activity of aza and deaza analgoues of IsoddA and their phosphates as prodrugs. J. Med. Chem. 37: 3534-3541.*

* cited by examiner

*Primary Examiner* — Karen Cochrane Carlson
(74) *Attorney, Agent, or Firm* — Toby D. Hain

(57) ABSTRACT

A process for making a nucleotide analog includes combining a first substrate that includes a linker and a base with a second substrate to form a substrate composition. An enzyme contacts the substrate composition and catalyzes formation of the nucleotide analog from the first substrate and the second substrate. Additionally, a composition includes the first substrate, second substrate, the enzyme, the nucleotide analog, and optional additives.

20 Claims, 4 Drawing Sheets

NUCLEOTIDE ANALOGS AND PROCESS FOR MAKING SAME ENZYME

CROSS REFERENCE TO RELATED APPLICATIONS

This application claims the benefit of U.S. Provisional Application Ser. No. 61/761,896 filed Feb. 7, 2013, the disclosure of which is incorporated herein by reference in its entirety.

STATEMENT REGARDING FEDERALLY SPONSORED RESEARCH

This invention was made with government support from the National Institute of Standards and Technology and also under Award No. MCB1048394 from the National Science Foundation. The government has certain rights in the invention.

SEQUENCE LISTING

This application contains a Sequence Listing. CD-ROM discs Copy 1 and Copy 2 are identical, contain a copy of the Sequence Listing under 37 CFR Section 1.821 (e), and are read-only memory computer-readable compact discs. Each CD-ROM disc contains a copy of the Sequence Listing in ASCII text format. The Sequence Listing is named "13-011 Sequence Listing_ST25.txt." The electronic file of the Sequence Listing contained on each of these CD-ROMs was created on Feb. 27, 2014, and is 7 kilobytes in size. The copies of the Sequence Listing on the CD-ROM discs are hereby incorporated by reference in their entirety.

BACKGROUND

Chemical synthesis has been used to produce various pharmaceutical compounds. Such synthesis typically includes numerous synthetic steps, which decrease the product yield as the number of steps increase. Moreover, chemical synthesis produces racemic mixtures of products, which generally must be resolved in order to isolate a particularly biologically active compound. Many synthetic methodologies are time consuming and require costly materials. As an alternative to chemical synthesis, an enzyme can be used to produce pharmaceutical compounds. However, enzymes can be inactivated under certain circumstances, including becoming denatured due to temperature, pH, and the like such that the reaction conditions must be monitored and controlled, which diminishes cost savings and require careful handling to maintain the enzyme's activity.

Thus, development of efficient synthetic methods for production of pharmaceutical compounds would be advantageous and would be favorably received in the art.

BRIEF DESCRIPTION

The above and other deficiencies are overcome by, in an embodiment, a process for making a nucleotide analog, the process comprising:
combining a first substrate comprising a compound of formula 1

$$P^3-P^2-P^1-L-Q \qquad \text{Formula 1}$$

with a second substrate comprising a compound of formula 27

$$R-Q^1-R^5 \qquad \text{Formula 27}$$

to form a substrate composition;
contacting the substrate composition with an enzyme; and
catalyzing, with the enzyme, formation of the nucleotide analog of formula 28 from the first substrate and the second substrate $$R-Q^1-P^1-L-Q \qquad \text{Formula 28}$$

wherein the enzyme comprises an amino acid sequence with a homology of at least 30% compared to an amino acid sequence comprising
MSKLLREVTPEERRLYYSGEWDAKKLPEFIVESI-ERREFGFDHTGEGPSDRK NAFSDVRDLEDYI-RATAPYAAYSSVAFYRNPQEMEGWLGAELVF-DIDAKD LPLRRCQNEHPSGQVCPICLEDAKELARDTLI-ILKEDFGFENIHVVYSGRGY HIRVIDEWALKLD-SKARERILSYVSAAEEVTFDDIQKRYIMLSSGY-FRVFRL RFGYFIQRINENHLKNIGLKRSTAEKLLDEKTRQ-DIVEKFVNKGLLAAFPEG VGYRTLLRLFGLST-TFSKAYFDGRVTVDLKRILRLPSTLHSKVGL-VATYIGS DEKRLEKFDPFKDAVPEFRKEEVQKAY-QEWKELHEG (SEQ ID NO: 1);
L is a linker comprising a structure of formula 3, formula 6, formula 7, formula 8, formula 9, formula 10, formula 11, or formula 12,

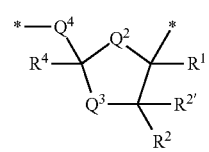

Formula 3

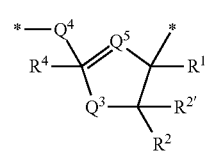

Formula 6

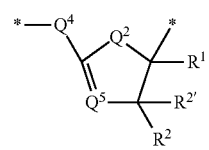

Formula 7

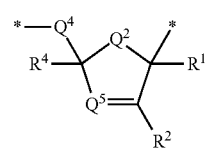

Formula 8

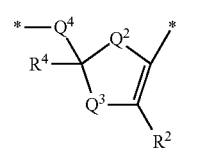

Formula 9

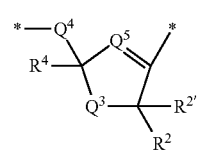

Formula 10

-continued

Formula 11
$*-Q^4-*$

Formula 12
$*-Q^4-Q^2-*$, wherein * is a point of attachment;

$Q^2$ and $Q^3$ are independently O, S, Se, NR, $CR_2$, or $C=CR_2$;

$Q^4$ is O, S, NR, $CR_2$, $CR_2CR_2$, $CR_2O$, $CR_2OCR_2$, $CR_2S$, $CR_2SCR_2$, $CR_2NR$, $CR_2NRCR_2$, alkenylene, alkylene, alkyleneoxy, alkynylene, amide, aralkylene, arylene, aryleneoxy, cycloalkylene, fluoroalkylene, heteroaralkylene, heteroarylene, heterocycloalkylene, or a single bond;

$Q^5$ is N or CR;

$R^1$, $R^2$, $R^{2'}$, and $R^4$ are independently R, OR, SR, $NR_2$, NROR, $NRNR_2$, $N_3$, $NO_2$, CHO, CN, $C(=O)NH_2$, or $C(=O)OR$; alternatively, $R^2$ and $R^{2'}$ together are =O, =S, =N—R, or $=CR_2$; and R is independently H, F, Cl, Br, I, OH, SH, NHOH, $NHNH_2$, CHO, C(=O)OH, alkenyl, alkenyleneamine, alkoxy, alkyl, alkyleneamine, alkynyl, amine, amino, aralkyl, aralkyloxy, aralkyloxy, aryl, aryleneamine, aryloxy, carbocyclic, carboxylic acid group or salt, cycloalkyl, cycloalkyloxy, haloalkyl, heteroaralkyl, heteroaryl, or heterocycloalkyl;

Q is a base comprising a structure of formula 13, formula 14, formula 15, or formula 16.

Formula 13
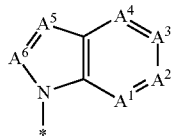

Formula 14
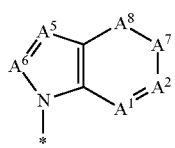

Formula 15
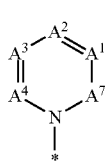

Formula 16
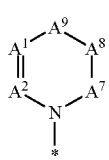

wherein $A^1$, $A^2$, $A^3$, $A^4$, $A^5$, and $A^6$ are independently N, C—$R^1$;

$A^7$, $A^8$, $A^9$ is independently N—$R^1$, $C(R^1)_2$, C=O, $C=C-(R^1)_2$, $C=N-R^1$; and $R^1$ is as defined above;

$P^1$ and $P^2$ are respectively a first phosphate group and a second phosphate group independently having a structure of formula 25, and $P^3$ is a third phosphate group having a structure of formula 26, Formula 25
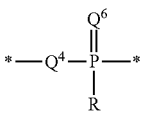

Formula 26
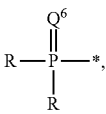

wherein $Q^6$ is O, NR, or S; and $Q^4$, R, and * are as defined above;

$Q^1$ is O, S, Se, NR, $CR_2$, or $C=CR_2$, cycloalkenylene, cycloalkylene, heterocycloalkenylene, heterocycloalkylene; and $R^5$ is H, F, Cl, Br, I, OH, SH, NHOH, $NHNH_2$, CHO, alkenyleneamine, alkyleneamine, amine, aryleneamine, or carboxylic acid group or salt.

Further disclosed is a composition comprising:

a first substrate comprising a compound of formula 29

Formula 29
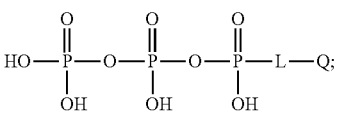

a second substrate comprising a compound of formula 27

$R-Q^1-R^5$;  Formula 27 an enzyme comprising an amino acid sequence with a homology of at least 30% compared to an amino acid sequence comprising

```
MSKLLREVTPEERRLYYSGEWDAKKLPEFIVESIERREFGFDHTGEGPSD
RKNAFSDVRDLEDYIRATAPYAAYSSVAFYRNPQEMEGWLGAELVFDIDA
KDLPLRRCQNEHPSGQVCPICLEDAKELARDTLIILKEDFGFENIHVVYS
GRGYHIRVIDEWALKLDSKARERILSYVSAAEEVTFDDIQKRYIMLSSGY
FRVFRLRFGYFIQRINENHLKNIGLKRSTAEKLLDEKTRQDIVEKFVNKG
LLAAFPEGVGYRTLLRLFGLSTTFSKAYFDGRVTVDLKRILRLPSTLHSK
VGLVATYIGSDEKRLEKFDPFKDAVPEFRKEEVQKAYQEWKELHEG;
and
``` a nucleotide analog formed by the enzyme from the first substrate and the second substrate, the nucleotide analog comprising a compound of formula 30

Formula 30
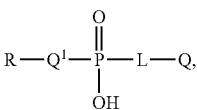

wherein L is a linker comprising a structure of formula 3, formula 6, formula 7, formula 8, formula 9, formula 10, formula 11, or formula 12

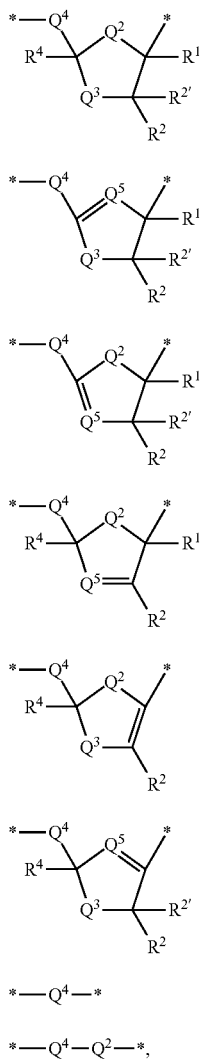

Formula 3

Formula 6

Formula 7

Formula 8

Formula 9

Formula 10

Formula 11

Formula 12 wherein * is a point of attachment;

$Q^2$ and $Q^3$ are independently O, S, Se, NR, $CR_2$, or $C=CR_2$, $Q^4$ is O, S, NR, $CR_2$, $CR_2CR_2$, $CR_2O$, $CR_2OCR_2$, $CR_2S$, $CR_2SCR_2$, $CR_2NR$, $CR_2NRCR_2$, alkenylene, alkylene, alkyleneoxy, alkynylene, amide, aralkylene, arylene, aryleneoxy, cycloalkylene, fluoroalkylene, heteroaralkylene, heteroarylene, heterocycloalkylene, or a single bond;

$Q^5$ is N or CR;

$R^1$, $R^2$, $R^{2'}$, and $R^4$ are independently R, OR, SR, $NR_2$, NROR, $NRNR_2$, $N_3$, $NO_2$, CHO, CN, $C(=O)NH_2$, or $C(=O)OR$; alternatively, $R^2$ and $R^{2'}$ together are $=O$, $=S$, $=N-R$, or $=CR_2$; and R is independently H, F, Cl, Br, I, OH, SH, NHOH, $NHNH_2$, CHO, $C(=O)OH$, alkenyl, alkenyleneamine, alkoxy, alkyl, alkyleneamine, alkynyl, amine, amino, aralkyl, aralkyloxy, aralkyloxy, aryl, aryleneamine, aryloxy, carbocyclic, carboxylic acid group or salt, cycloalkyl, cycloalkyloxy, haloalkyl, heteroaralkyl, heteroaryl, or heterocycloalkyl;

Q is a base comprising

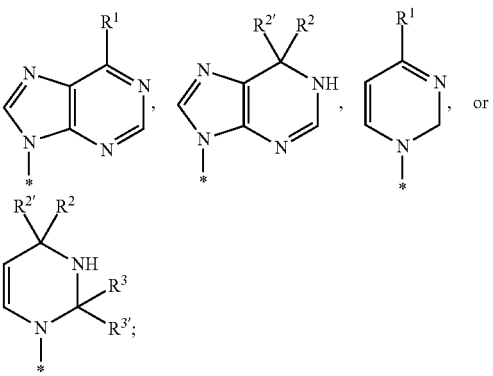

$Q^1$ is O, S, Se, NR, $CR_2$, or $C=CR_2$, cycloalkenylene, cycloalkylene, heterocycloalkenylene, heterocycloalkylene; and $R^5$ is H, F, Cl, Br, I, OH, SH, NHOH, $NHNH_2$, CHO, alkenyleneamine, alkyleneamine, amine, aryleneamine, or carboxylic acid group or salt.

BRIEF DESCRIPTION OF THE DRAWINGS

The following descriptions should not be considered limiting in any way. With reference to the accompanying drawings, like elements are numbered alike.

DETAILED DESCRIPTION

Figure 1:
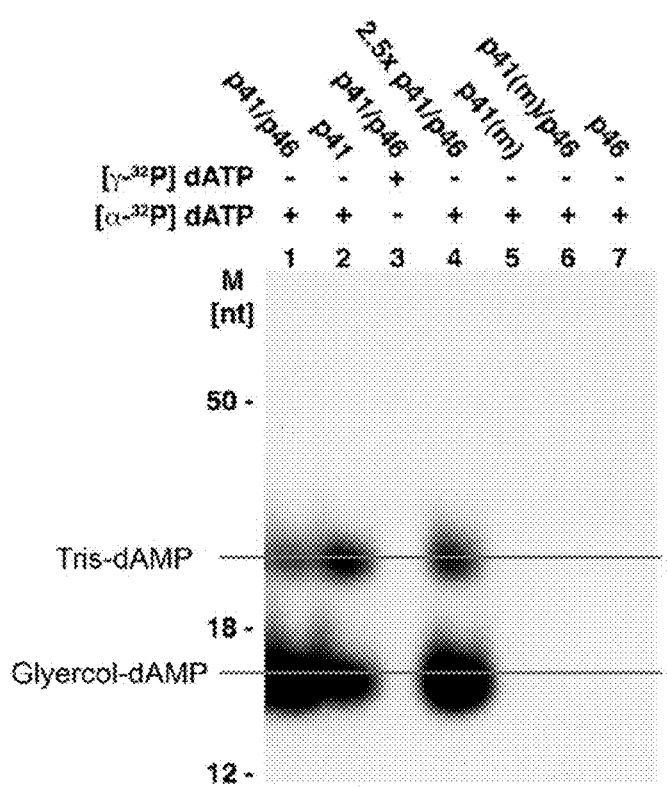
FIG. 1 shows a developed urea-PAGE gel indicating the presence or absence of nucleotide analogs in various experiments.

A detailed description of one or more embodiments is presented herein by way of exemplification and not limitation.

It has been found that an enzyme having a certain amino acid sequence or within a certain homology thereto catalytically forms a nucleotide analog. The enzyme forms the nucleotide analog from readily available materials in an efficient, one-pot manner. Beneficially, the enzyme is thermally stable and active over a wide range of conditions, and the resulting nucleotide analog is useful as, e.g., a prodrug. Moreover, the enzymatic synthesis herein advantageously is low cost, is applicable to numerous different substrates, and constitutes preparation of nucleotide analogs comporting with green chemistry principles.

According to an embodiment, a method for making a nucleotide analog includes combining a first substrate and a second substrate to form a substrate composition, contacting the substrate composition with an enzyme, and catalyzing (with the enzyme) formation of the nucleotide analog from the first substrate and the second substrate. In this manner, a chemical structure of the nucleotide analog incorporates a portion of the first substrate and a portion of the second substrate.

According to an embodiment, the first substrate is a compound of formula 1.

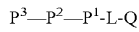  Formula 1 wherein Q is a base; L is a linker; and $P^1$, $P^2$, and $P^3$ respectively are a first phosphate group, a second phosphate group, and a third phosphate group.

Exemplary first substrates include ribonucleoside triphosphates and deoxyribonucleoside triphosphates such as adenosine triphosphate (ATP), cytosine triphosphate (CTP), guanosine triphosphate (GTP), uracil triphosphate (UTP), deoxyadenosine triphosphate (dATP), deoxycytosine triphosphate (dCTP), deoxyguanosine triphophosphate (dGTP), and deoxythymine triphosphate (dTTP). Additionally, the first substrate includes non-canonical nucleoside triphosphates (e.g., inosine and xanthine) as described more fully below.

According to an embodiment, the linker L is a divalent species that includes a sugar (e.g., a furanosyl ring or a pyranosyl ring), a modified sugar, or an acyclic group (e.g., an acyclic ether, an acyclic mercaptan, an acyclic (e.g., linear or branched) sugar, and the like). The modified sugar is a chemically-modified furanosyl sugar or a non-furanosyl sugar, a furanosyl sugar analog, a derivative including a bicyclic sugar, a morpholino, a tetrahydropyran, a cyclohexenyl, a cyclohexitol, a 2'-modified sugar, 3'-modified sugar a 4'-modified sugar, a 5'-modified sugar, a substituted compound of any of the foregoing modified sugars, or the like. Further, the modified sugar includes a structure that replaces a furanose ring of a naturally occurring nucleoside. In certain embodiments, the modified sugar is a non-furanose ring (e.g. a six-membered ring), or a group having a plurality of rings (fused, non-fused, or spiro).

In some embodiments, the linker L of the first substrate or the nucleotide analog is a sugar such as a ribose, deoxyribose, or dideoxyribose. In an embodiment, the linker L includes a derivative of ribose, deoxyribose, or dideoxyribose. Such derivatives include, e.g. replacement or deletion of a carbon or oxygen atom in a ring of the sugar with a different atom (e.g., a heteroatom or carbon), inclusion of a double bond in the ring, inclusion of a functional group attached to an atom in the ring, or replacement of the ring structure of a cyclic sugar with an acyclic structure. It is contemplated that any of the ring carbons in the sugar is substituted with a functional group (e.g., alkoxy), or OH or H is attached to the ring carbon atom. In some embodiments, the hydrogen or hydroxyl group of a ring carbon is modified or replaced with an oxy group, e.g., a functional group containing oxygen, or a protecting group.

Exemplary functional groups include alkenyl, alkoxy or aryloxy (e.g., OR, wherein R is H, alkyl, cycloalkyl, aryl, aralkyl, heteroaryl or sugar), alkyl, alkylamino, alkyl-thio-alkyl, alkynyl, amide (e.g., NHC(O)R, wherein R is alkyl, cycloalkyl, aryl, aralkyl, heteroaryl or sugar), amino (e.g., $NH_2$; alkylamino, heterocyclyl, arylamino, heteroaryl amino, or amino acid), aryl, arylamino, cyano, cycloalkyl, halo (e.g., F), heteroaryl amino, $N_3$, heterocyclyl, mercapto, thioalkoxy, or thioalkyl, which is optionally substituted.

In some embodiments, the linker L of the first substrate or the reaction product is a sugar or sugar derivative having a cyclic structure of formula 2

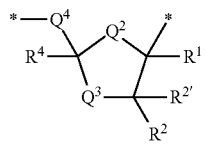  Formula 2 wherein * (asterisk) is a point of attachment;

$Q^2$ and $Q^3$ are independently O, S, Se, NR, $CR_2$, or $C=CR_2$;

$Q^4$ is O, S, NR, $CR_2$, $CR_2CR_2$, $CR_2O$, $CR_2OCR_2$, $CR_2S$, $CR_2SCR_2$, $CR_2NR$, $CR_2NRCR_2$, alkenylene, alkylene, alkyleneoxy, alkynylene, amide, amine, aralkylene, arylene, aryleneoxy, cycloalkylene, fluoroalkylene, heteroaralkylene, heteroarylene, heterocycloalkylene, or a single bond;

$R^1$, $R^2$, $R^{2'}$, and $R^4$ are independently R, OR, SR, $NR_2$, NROR, $NRNR_2$, $N_3$, $NO_2$, CHO, CN, $C(=O)NH_2$, or $C(=O)OR$; alternatively, $R^2$ and $R^{2'}$ together are =O, =S, =N—R, or $=CR_2$; and R is independently H, F, Cl, Br, I, OH, SH, NHOH, $NHNH_2$, CHO, $C(=O)OH$, alkenyl, alkenyleneamine, alkoxy, alkyl, alkyleneamine, alkynyl, amine, amino, aralkyl, aralkyloxy, aralkyloxy, aryl, aryleneamine, aryloxy, carbocyclic, carboxylic acid group or salt, cycloalkyl, cycloalkyloxy, haloalkyl, heteroaralkyl, heteroaryl, or heterocycloalkyl.

Exemplary $Q^4$ groups include —O—, —NH—, —S—, —C(O)—, C(O)—NH, NH—C(O)—NH, O—C(O)—NH, —C(S)—, —$CH_2$—, —$CH_2$—$CH_2$—, —$CH_2$—$CH_2$—$CH_2$—, —$CH_2$—$CH_2$—$CH_2$—$CH_2$—, —O—$CH_2$—, —$CH_2$—O—, —O—$CH_2$—$CH_2$—, —$CH_2$—O—$CH_2$—, —$CH_2$—$CH_2$—O—, —O—$CH_2$—$CH_2$—$CH_2$—, —$CH_2$—O—$CH_2$—$CH_2$—, —$CH_2$—$CH_2$—O—$CH_2$—, —$CH_2$—$CH_2$—$CH_2$—O—, —O—$CH_2$—$CH_2$—$CH_2CH_2$—, —$CH_2$—O—$CH_2$—$CH_2$—$CH_2$—, —$CH_2$—$CH_2$—O—$CH_2$—$CH_2$—, —$CH_2$—$CH_2$—$CH_2$—O—$CH_2$—, —$CH_2$—$CH_2$—$CH_2$—$CH_2$—O—$CH_2$—, —$CH_2$—$CH_2$—$CH_2$—$CH_2$—O—, —C(O)—NH—$CH_2$—, —C(O)—NH—$CH_2$—$CH_2$—, —$CH_2$—C(O)—NH—$CH_2$—, —$CH_2$—$CH_2$—C(O)—NH—, —C(O)—NH—$CH_2$—$CH_2$—$CH_2$—, —$CH_2$—C(O)—NH—$CH_2$—$CH_2$—, —$CH_2$—$CH_2$—C(O)—NH—$CH_2$—, —$CH_2$—$CH_2$—$CH_2$—C(O)—NH—, —C(O)—NH—$CH_2$—$CH_2$—$CH_2$—$CH_2$—, —$CH_2$—C(O)—NH—$CH_2$—$CH_2$—$CH_2$—, —$CH_2$—$CH_2$—C(O)—NH—$CH_2$—$CH_2$—, —$CH_2$—$CH_2$—$CH_2$—C(O)—NH—$CH_2$—, —$CH_2$—$CH_2$—$CH_2$—$CH_2$—C(O)—NH—, —$CH_2$—$CH_2$—C(O)—NH—$CH_2$—$CH_2$—, —$CH_2$—$CH_2$—C(O)—NH—, —NH—C(O)—$CH_2$—, —$CH_2$—NH—C(O)—$CH_2$—, —$CH_2CH_2$—NH—C(O)—NH—$CH_2$—, —C(O)—NH—$CH_2$—$CH_2$—, —O—C(O)—NH—$CH_2$—, —O—C(O)—NH—$CH_2$—$CH_2$—, —NH—$CH_2$—, —NH—$CH_2$—$CH_2$—, —$CH_2$—NH—$CH_2$—, —$CH_2$—$CH_2$—NH—$CH_2$—, —C(O)—$CH_2$—, —C(O)—$CH_2$—$CH_2$—, —$CH_2$—C(O)—$CH_2$—, —$CH_2$—$CH_2$—C(O)—$CH_2$—, —$CH_2$—$CH_2$—C(O)—$CH_2$—$CH_2$—, —$CH_2$—$CH_2$—C(O)—$CH_2$—$CH_2$—, —$CH_2$—$CH_2$—C(O)—, —$CH_2$—$CH_2$—$CH_2$—C(O)—NH—CH—$CH_2$—NH—, —$CH_2CH_2CH_2$—C(O)—NH—$CH_2$—$CH_2$—NH—C(O)—, —$CH_2$—$CH_2$—$CH_2$—C(O)—NH—$CH_2CH_2$—NH—C(O)—$CH_2$—, and the like.

In an embodiment, the linker L is a sugar or sugar derivative having a cyclic structure of formula 3, formula 4, or formula 5.

Formula 3

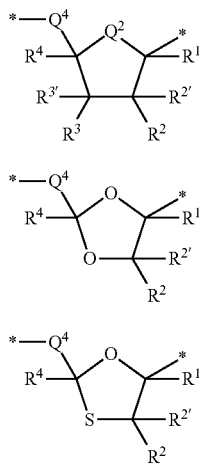

Formula 4

Formula 5

In some embodiments, the linker L is a cyclic structure having an unsaturated bond among the atoms in the cycle as in formula 6, formula 7, formula 8, formula 9, or formula 10.

Formula 6

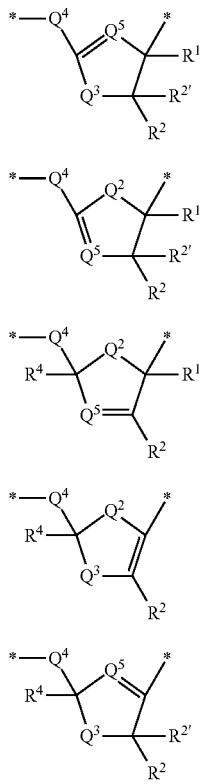

Formula 7

Formula 8

Formula 9

Formula 10

Exemplary linkers L with a cyclic ring structure include

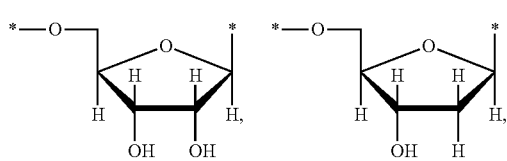

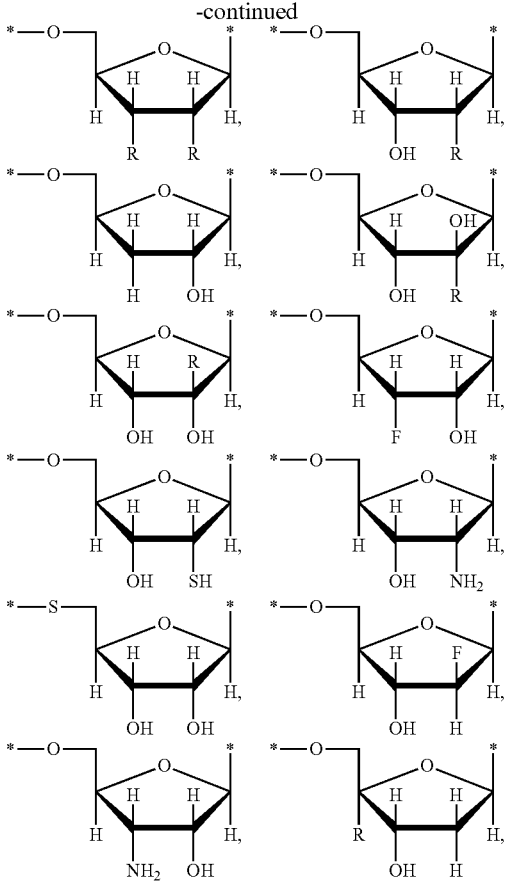

and the like.

According to an embodiment, the linker L includes an acyclic group. The acyclic group can be represented by a structure wherein a bond between atoms in, e.g., ribose ring (e.g. C1'-C2', C2'-C3', C3'-C4', C4'-O4', C1'-O4') or a ring atom (e.g., C1', C2', C3', C4' or O4') independently is absent. Thus, in an embodiment, the linker L is an acyclic group as in formula 11 or formula 12.

$$*-Q^4-*$$ Formula 11

$$*-Q^4-Q^2-*$$ Formula 12

Exemplary linkers L having an acyclic structure include

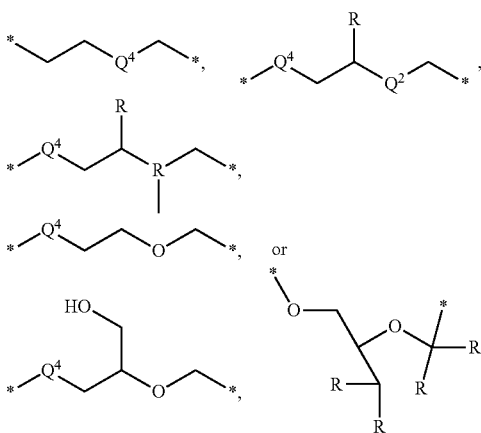

-continued or the like.

wherein each R is independently given as defined above. Further exemplary linkers L include —O—, —NH—, —S—, —C(O)—, C(O)—NH, NH—C(O)—NH, O—C(O)—NH, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$CH$_2$—, CH$_2$—O—CH$_2$—CH$_2$—CH$_2$—, —CH$_2$—CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —NH—C(O)—CH$_2$—, —CH$_2$—NH—C(O)—CH$_2$—, —CH$_2$CH$_2$—NH—C(O)—NH—CH$_2$—, —NH—C(O)—NH—CH$_2$—CH$_2$—, —CH$_2$—NH—C(O)—CH$_2$—CH$_2$—, —CH$_2$—CH$_2$—NH—C(O)—CH$_2$—CH$_2$—, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH$_2$—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH—CH$_2$—NH—, —CH$_2$CH$_2$CH$_2$—C(O)—NH—CH$_2$—CH$_2$—NH—C(O)—, —CH$_2$—CH$_2$—CH$_2$—C(O)—NH—CH$_2$CH$_2$—NH—C(O)—CH$_2$—, and the like.

In addition to the linker L, the first substrate and the nucleotide analog formed therefrom also include a base Q. In some embodiments, the base Q refers to a monovalent heterocyclic base of a naturally occurring nucleoside e.g., adenine, cytosine, guanidine, uracil, thymidine. Additionally, the base Q is naturally occurring or modified so that the base Q includes, e.g. an analog of a naturally occurring nucleoside.

In an embodiment, the base Q has a structure of formula 13, formula 14, formula 15, or formula 16.

Formula 13

Formula 14

Formula 15

Formula 16 wherein $A^1$, $A^2$, $A^3$, $A^4$, $A^5$, and $A^6$ are independently N, $CR^1$;

$A^7$, $A^8$, $A^9$ is independently $NR^1$, $C(R^1)$, C=O, C=C$(R^1)_2$, C—$NR^1$; and $R^1$ is as defined above.

Specifically, the base Q has a structure of formula 17, formula 18, formula 19, or formula 20.

Formula 17

Formula 18

Formula 19

Formula 20

More specifically, the base Q has a structure of formula 21, formula 22, formula 23, or formula 24.

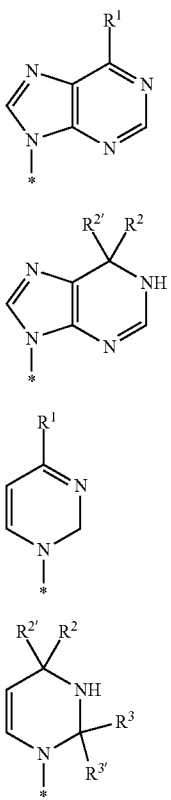

Formula 21

Formula 22

Formula 23

Formula 24 wherein $R^3$ and $R^{3'}$ are independently R, OR, SR, $NR_2$, NROR, $NRNR_2$, $N_3$, $NO_2$, CHO, CN, $C(=O)NH_2$, or $C(=O)OR$, alternatively, $R^3$ and $R^{3'}$ together are =O, =S, =NR, or $=CR_2$.

Thus, the base Q includes a monovalent species of a purine base (e.g., adenine (A), guanine (G)), a pyrimidine base (e.g., thymine (T), cytosine (C), uracil (U)), or a heterocyclic base that has been modified. Such modifications include a methylated purine or pyrimidine, an acylated purine or pyrimidine, an aminated or alkalyated ribose, or an aminated deoxyribose, or other heterocycle. In some embodiments, the base Q includes monovalent species of diaminopurine and its derivatives, inosine and its derivatives, alkylated purines or pyrimidines, acylated purines or pyrimidines, thiolated purines or pyrimidines, and the like, or addition of a protecting group (e.g., acetyl, difluoroacetyl, trifluoroacetyl, isobutyryl, benzoyl, 9-fluorenylmethoxycarbonyl, phenoxyacetyl, dimethylformamidine, dibutylformamidine, N,N-diphenyl carbamate) to the base Q.

Further exemplary bases Q are monovalent species of 1-methyladenine, 1-(aminoalkylamino-carbonylethylenyl)-2(thio)-pseudouracil, 1-(aminoalkylaminocarbonylethylenyl)-2,4-(dithio)pseudouracil, 1-(aminoalkylaminocarbonylethylenyl)-4-(thio)pseudouracil, 1-(aminoalkylaminocarbonylethylenyl)-pseudouracil, 1-(aminocarbonylethylenyl)-2(thio)-pseudouracil, 1-(aminocarbonylethylenyl)-2,4-(dithio)pseudouracil, 1-(aminocarbonylethylenyl)-4-(thio)pseudouracil, 1-(aminocarbonylethylenyl)-pseudouracil, 1-(aza)-2-(thio)-3-(aza)-phenoxazin-1-yl, 1-(aza)-2-(thio)-3-(aza)-phenthiazin-1-yl, 1-methylguanine, 1-methylinosine, 1-methylpseudouracil, 2-(alkyl)adenine, 2-(alkyl)guanine, 2-(amino)adenine, 2-(amino)purine, 2-(aminoalkyll)adenine, 2-(aminopropyl) adenine, 2-(halo)adenine, 2-(methylthio)-N6-(isopentenyl) adenine, 2-(propyl)adenine, 2-(propyl)guanine, 2-(thio)cytosine, 2-(thio)uracil, 2-aminopurine, 2-aza-inosinyl, 2-methyladenine, 2-methylguanine, 2-methylthio-N6-isopentyladenine, 2-pyridinone, 2-thiocytosine, 2-thiouracil, 3-(3-amino-3-carboxypropyl)uracil, 3-(alkyl)cytosine, 3-(deaza)-5-(aza)cytosine, 3-(methyl)-7-(propynyl)isocarbostyrilyl, 3-(methyl)cytosine, 3-(methyl)isocarbostyrilyl, 3-methyl isocarbostyrilyl, 3-methyl-7-propynyl isocarbostyrilyl, 3-methylcytosine, 3-nitropyrrole, 4-(fluoro)-6-(methyl)benzimidazole, 4-(methyl)benzimidazole, 4-(thio) uracil, 4-acetylcytosine, 4-fluoro-6-methylbenzimidazole, 4-methylbenzimidazle, 5-(1,3-diazole-1-alkyl)uracil, 5-(2-aminopropyl)uracil, 5-(2-bromovinyl)uracil, 5-(alkyl)-2-(thio)pseudouracil, 5-(alkyl)-2,4-(dithio)pseudouracil, 5-(alkyl)-4-(thio)pseudouracil, 5-(alkyl)cytosine, 5-(alkyl) pseudouracil, 5-(alkyl)uracil, 5-(alkynyl)cytosine, 5-(alkynyl)uracil, 5-(allylamino)uracil, 5-(aminoalkyl)uracil, 5-(aminoallyl)uracil, 5-(carboxyhydroxymethyl)uracil, 5-(carboxymethylaminomethyl)-uracil, 5-cyanoalkyl)uracil, 5-(dialkylaminoalkyl)uracil, 5-(dimethylaminoalkyl)uracil, 5-(guanidiniumalkyl)uracil, 5-(halo)cytosine, 5-(halo)uracil, 5-(methoxy)uracil, 5-(methoxycarbonylmethyl)-2-(thio) uracil, 5-(methoxycarbonyl-methyl)uracil, 5-(methyl)-2,5-(methyl)-2-(thio)pseudouracil, 5-(methyl)-2-(thio)uracil, 5-(methyl)-2,4-(dithio)pseudouracil, 5-(methyl)-4-(thio) pseudouracil, 5-(methyl)-4-(thio)uracil, 5-(methyl)cytosine, 5-(methyl)isocarbostyrilyl, 5-(methyl)pseudouracil, 5-(methylaminomethyl)-2,5-(methylaminomethyl)-2-(thio) uracil, 5-(methylaminomethyl)-4-(thio)uracil, 5-(methylaminomethyl)uracil, 5-(propynyl)cytosine, 5-(propynyl)uracil, 5-(trifluoromethyl)cytosine, 5-(trifluoromethyl)uracil, 5-bromouracil, 5-chlorouracil, 5-ethylcytosine, 5-ethyluracil, 5-fluorouracil, 5-hydroxymethyluracil, 5-iodouracil, 5-methoxyuracil, 5-methyl isocarbostyrilyl, 5-methyl-2-thiouracil, 5-methylcytosine, 5-nitroindole, 5-propyluracil, 6-(alkyl)adenine, 6-(alkyl)guanine, 6-(aza)pyrimidine, 6-(azo)cytosine, 6-(azo)thymine, 6-(azo)uracil, 6-(methyl)-7-(aza)indolyl, 6-(methyl)adenine, 6-(methyl)guanine, 6-hydroxyaminopurine, 6-methyl-7-azaindolyl, 6-thiopurine, 7-(alkyl)guanine, 7-(aminoalkylhydroxy)-1-(aza)-2-(thio)-3-(aza)-phenoxazin-1-yl, 7-(aminoalkylhydroxy)-1-(aza)-2-(thio)-3-(aza)-phenthiazin-1-yl, 7-(aza)indolyl, 7-(deaza)adenine, 7-(deaza)guanine, 7-(guanidiniumalkylhydroxy)-1-(aza)-2-(thio)-3-4 aza)-phenoxazin-1-yl, 7-(guanidiniumalkylhydroxy)-1-(aza)-2-(thio)-3-(aza)-phenthiazin-1-yl, 7-(guanidiniumalkylhydroxy)-1,3-(diaza)-2-(oxo)-phenoxazin-1-yl, 7-(methyl)guanine, 7-(propynyl) isocarbostyrilyl, 7-azaindolyl, 7-deaza-inosinyl, 7-methylguanine, 7-propynyl isocarbostyrilyl, 8-(alkenyl) adenine, 8-(alkenyl)guanine, 8-(alkyl)adenine, 8-(alkyl)guanine, 8-(alkynyl)adenine, 8-(alkynyl)guanine, 8-(amino)adenine, 8-(amino)guanine, 8-(halo)adenine, 8-(halo)guanine, 8-(hydroxyl)adenine, 8-(hydroxyl)guanine, 8-(thioalkyl)adenine, 8-(thioalkyl)guanine, 8-(thiol)adenine, 8-(thiol)guanine, 8-aminoguanine, K-aza-7-deazaadenine, 8-bromoadenine, 8-bromoguanine, 8-chloroguanine, 8-methylguanine, K-thioguanine, 9-(methyl)-imidizopyridinyl, aminoindolyl, dihydrouracil, hypoxanthine, imidizopyridinyl, inosine, inosinyl, isocarbostyrilyl, isoguanisine, N-(methyl)guanine, N3-(methyl)uracil, N4-(acetyl)cytosine, N6-(isopentyl)adenine, N6-(methyl)adenine, N6-isopentyladenine, N6-methyladenine, nitrobenzimidazolyl, nitroimidazolyl, nitroimidazolyl, nitroindolyl, nitropyrazolyl, nubularine, propynyl-7-(aza)indolyl, pseudouracil, pyrrolopyrimidinyl, pyrrolopyrizinyl, queosine, tubercidine, uracil-5-oxyacetic acid, uracil-5-oxyacetic acid methyl ester, xanthine, 1,3-

(diaza)-2-(oxo)-phenoxazin-1-yl, 1,3-(diaza)-2-(oxo)-phenthiazin-1-yl, 1,3,5-(triaza)-2,6-(dioxa)-naphthalene, 2,2-dimethylguanine, 2,4-(dithio)pseudouracil, 2,4,5-(trimethyl)phenyl-4-(methyl)indolyl, 2,6-(diamino)purine, 2,6-diaminopurine, 4-(dithio)uracil, 4,6-(dimethyl)indolyl, 4,6-dimethylindolyl, 7-(aminoalkylhydroxy)-1,3-(diaza)-2-(oxo)-phenoxazin-1-yl, 7-(aminoalkylhydroxy)-1,3-(diaza)-2-(oxo)-phenthiazin-1-yl, 7-(guanidiniumalkyl-hydroxy)-1,3-(diaza)-2-(oxo)-phenthiazin-1-yl, N,N-dimethyladenine, N6,N6-(dimethyl)adenine, and the like. It is contemplated that any of the above bases Q can be modified as an analog or substituted, e.g., O-alkylated, N-alkylated, or a halogenated.

In addition to the linker L, and the base Q, the first substrate also includes first phosphate group $P^1$, second phosphate group $P^2$, and third phosphate group $P^3$. The first phosphate group $P^1$ and the second phosphate group $P^2$ independently have a structure of formula 25.

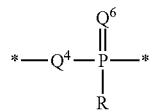

Formula 25 wherein $Q^6$ is O, NR, or S; and $Q^4$, R, and * are as defined above. In an embodiment, the first phosphate group $P^1$, and the second phosphate group $P^2$ have the formula

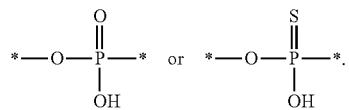

The third phosphate group P3 has a structure of formula 26.

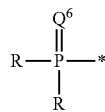

Formula 26 wherein Q6, R and * are as defined above. In an embodiment, the third phosphate group P3 has the formula

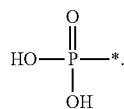

According to an embodiment, the first substrate reacts with the second substrate to form the nucleotide analog. Without wishing to be bound by theory, in forming the nucleotide analog, the first substrate and the second substrate are condensed via a hydrolysis reaction catalyzed by the enzyme. As such, in an embodiment, the $R^5$ group of the second substrate is a substituent that is cleaved from the *-$Q^1$-R (wherein * is a point of attachment) part of the second substrate, which is incorporated into the nucleotide analog. Therefore, the second substrate is any compound that includes an $R^5$ group that can participate in the enzyme catalyzed coupling reaction to the first substrate, particularly a group that participates in a hydrolysis reaction whereby *-$Q^1$-R is available to bond to first phosphate group P1 of the first substrate, as explained more fully below. In a particular embodiment, the second substrate includes a group $Q^1$, that after reaction with the second substrate, has a nitrogen atom or oxygen atom bonded to the phosphorous atom of the first phosphate group $P^1$ (from the second substrate) in the product nucleotide analog. That is, in the nucleotide analog, an O—P or N—P bond is formed, wherein the O atom (in the O—P bond) and the N atom (in the N—P bond) is from the $Q^1$ group of the second substrate, and the P atom is from the first phosphate group $P^1$ of the first substrate.-=

In an embodiment, the second substrate is a compound of formula 27.

R-Q-R<sup>5</sup>  Formula 27 wherein Q1 is O, S, Se, NR, $CR_2$, or $C=CR_2$, a cycloalkenylene, a cycloalkylene, a heterocycloalkenylene, a heterocycloalkylene; and $R^5$ is H, F, Cl, Br, I, OH, SH, NHOH, $NHNH_2$, CHO, an alkenyleneamine, an alkyleneamine, an amine, an aryleneamine, or a carboxylic acid group or salt.

In some embodiments, the second substrate is an alcohol, an amino acid, a chromophore, a fatty acid, a sugar, or a combination comprising at least one of the foregoing.

The sugar includes, e.g., a monosaccharide (e.g., glucose, galactose, mannose, fructose) a disaccharide (e.g., sucrose, lactose, maltose, trehalose, cellobiose), an oligosaccharide, or a combination comprising at least one of the foregoing. In some embodiments, the sugar is a sugar alcohol (also known as a polyol, polyhydric alcohol, or polyalcohol) that is a hydrogenated form of carbohydrate, whose carbonyl group (aldehyde or ketone, reducing sugar) has been reduced to a primary or secondary hydroxyl group. Thus, the sugar includes a sugar alcohol having the general formula $H(HCHO)_{n+1}H$ as well as a sugar having a formula of $H(HCHO)_nHCO$.

Exemplary polyols include triols, e.g., glycerol, trimethylol propane, pentaerythritol, tris(2-hydroxyethyl) isocyanurate, and the like; tetrols such as dipentaerythritol; and other sugar alcohols such as inositol, myoinositol, sorbitol, and the like.

In an embodiment, the sugar is a reducing sugar that includes a monosaccharide, disaccharide, oligosaccharide, polysaccharide, a derivative thereof, or a combination thereof. Particularly, the reducing sugar can be an aldose, ulosonic acid, ketose, ulronic acid, or a combination thereof. More particularly, examples of the reducing sugar include glyceraldehyde, erythrose, threose, ribose, arabinose, xylose, lyxose, allose, altrose, glucose, mannose, gulose, idose, galactose, talose, dihydroxyacetone, erythrulose, ribulose, xylulose, psicose, fructose, sorbose, tagatose, glucoronic acid, galacturonic acid, cellobiose, maltose, lactose, melibiose, maltulose, lactulose, isomaltose, laminaribiose, maltotriose, a derivative thereof, or a combination thereof.

As used herein, the term "monosaccharide" refers to a polyhydroxy aldehyde H—$[CHOH]_a$—CHO or polyhydroxy ketone H—$[CHOH]_b$—CO—$[CHOH]_c$—H with a, b, and c being independently three or more carbon atoms, specifically a, b, and c being independently about 3 to about 50, and more specifically a, b, and c being independently about 3 to about 25. "Monosaccharide" (as opposed to an oligosaccharide or polysaccharide) denotes a single unit, without glycosidic connection to other such units. In an embodiment, the monosaccharide includes an aldose, dialdose, aldoketose, ketose, diketose, deoxy sugar, amino sugar, and their derivatives. As used herein, "aldose" refers to a monosaccharide with an aldehydic carbonyl or potential aldehydic carbonyl group. As used herein, "ketose" refers to a ketonic carbonyl or potential ketonic carbonyl group. As used herein, the term "potential aldehydic carbonyl group" refers to the hemiacetal group arising from ring closure of the monosaccharide. As used herein, "dialdose" refers to a monosaccharide containing two (potential) aldehydic carbonyl groups. As used herein, "diketose" refers to a monosaccharide containing two (potential) ketonic carbonyl groups. As used herein, "ketoaldose" refers to a monosaccharide containing a (potential) aldehydic group and a (potential) ketonic group. It is noted that use of parenthesis around the word "potential" indicates that the group may be present or potentially present in the reducing sugar. As used herein, "deoxy sugar" refers to a monosaccharide in which an alcoholic hydroxy group has been replaced by a hydrogen atom, except at the anomeric carbon. As used herein, "amino sugar" refers to a monosaccharide in which an alcoholic hydroxy group has been replaced by an amino group. As used herein, "uronic acid" refers to a monocarboxylic acid derived from an aldose by replacement of the $CH_2OH$ group with a carboxy group. As used herein, "ulosonic acid" refers to a carboxylic acid derived from a ketose by replacement of the C1-hydroxyl group with a carboxy group, e.g, 3-deoxy-D-manno-oct-2-ulosonic acid.

Further, the D- or L-stereoisomer of the sugar, as applicable give a particular sugar, can be used as the second substrate.

The sugar can be a linear chain, cyclic configuration, or a combination thereof. In general, a temperature-dependent equilibrium exists between the linear and cyclic configurations of the sugar.

The sugar can be substituted. As used herein, the term "substituted sugar" refers to a sugar in which a hydrogen atom in a hydroxyl group of the sugar is replaced by a functional group. Examples of substituted reducing sugars include phosphate-containing sugars such as ribose-5-phosphate, ribose-3-phosphate, arabinose5-phosphate, arabinose-3-phosphate, glyceraldehyde-3-phosphate, and arabinose-3,5-diphosphate; acetylated reducing sugars such as 3,5-di-O-acetyl-D-ribose; and 5-O-benzoyl-D-arabinose. Examples of functional groups include phosphate, acetyl, hydrogen, alkyl, alkoxy, fluoroalkyl, cycloalkyl, heterocycloalkyl, cycloalkyloxy, aryl, aralkyl, aryloxy, aralkyloxy, heteroaryl, heteroaralkyl, alkenyl, alkynyl, $NH_2$, amine, alkyleneamine, aryleneamine, alkenyleneamine, and a combination thereof.

According to an embodiment, a buffer is present in the composition. The buffer (described more fully below) includes, e.g., 2-(N-morpholine) ethanesulfonic acid (MES), N-(2-acetamido) iminodiacetic acid (ADA), piperazine-N, N'-bis(2-ethanesulfonic acid) (PIPES), N-(2-acetamido)-2-aminoethanesulfonic acid (ACES), (2-aminoethyl)-trimethyl ammonium chloride hydrochloride (Cholamine), N,N-bis(2-hydroxy-ethyl)-2-aminoethane sulfonic acid (TES), 2-[4-(2-hydroxyethyl)-1-piperazinyl]ethanesulfonic acid (HEPES), tris(hydroxymethyl)aminomethane (TRIS), N-tris (hydroxyl-methyl)methylglycine (Tricine), N,N-bis(2-hydroxyethyl)-glycine (Bicine), 2-(N-cyclohexylamino) ethane-sulfonic acid (CHES), acetic acid, phosphoric acid, citric acid, ethylenediaminetetraacetic acid, boric acid, ethylenediaminetetraacetic acid), a salt thereof, and the like. It is contemplated that the second substrate is an aforementioned buffer compound or a combination thereof.

In an embodiment, the second substrate is an amino acid. It is contemplated that the coupling of the second substrate to the first substrate involves the amide group of the second substrate. The amino acid is naturally occurring amino acid or a synthetic $\alpha$, $\beta$, $\gamma$, or $\delta$ amino acid. Additionally, the amino acid includes, amino acids found in proteins. e.g., alanine, arginine, asparagine, aspartate, cysteine, glutamate, glutamine, glycine, histadine, isoleucine, leucine, lysine, methionine, phenylalanine, proline, serine, threonine, tryptophan, tyrosine, valine, and the like. In an embodiment, the amino acid is in an L-configuration. In some embodiments, the amino acid is a derivative of alanyl, argininyl, asparaginyl, aspartoyl, cysteinyl, glutaminyl, glutaroyl, glycinyl, histidinyl, isoleucinyl, leucinyl, lysinyl, methioninyl, phenylalaninyl, prolinyl, serinyl, threoninyl, tryptophanyl, tyrosinyl, valinyl, $\beta$-alanyl, $\beta$-argininyl, $\beta$-asparaginyl, $\beta$-aspartoyl, $\beta$-cysteinyl, $\beta$-glutaminyl, $\beta$-glutaroyl, $\beta$-glycinyl, $\beta$-histidinyl, $\beta$-isoleucinyl, $\beta$-leucinyl, $\beta$-lysinyl, $\beta$-methioninyl, $\beta$-phenylalaninyl, $\beta$-prolinyl, $\beta$-serinyl, $\beta$-threoninyl, $\beta$-tryptophanyl, $\beta$-tyrosinyl, $\beta$-valinyl. It is contemplated that, the term "amino acid" is an independent disclosure of each of the esters of $\alpha$, $\beta$, $\gamma$, or $\delta$ forms of alanine, arginine, asparagine, aspartate, cysteine, glutamate, glutamine, glycine, histadine, isoleucine, leucine, lysine, methionine, phenylalanine, proline, serine, threonine, tryptophan, tyrosine, valine in the D and L configurations.

Alcohols for use as the second substrate include $C_1$-$C_{15}$ alcohols, specifically $C_1$-$C_{10}$ alcohols, and more specifically $C_1$-$C_6$ alcohols. The alcohol can be linear chain, branched, cyclic, or a combination thereof. Exemplary alcohols include aliphatic alcohols such as methanol, ethanol, 1-propanol, 2-propanol, n-butanol, 2-butanol, 2-methyl-2-propanol, and higher homologues (e.g., cyclohexanol); dihydroxy alcohols such as ethylene glycol, propylene glycol, and 1,4-dihydroxybutane; trihydroxy alcohols such as glycerine; cycloaliphatic alcohols such as cyclohexanol and substituted cyclohexanols; and phenols and substituted phenols.

In an embodiment, the second substrate is a fatty acid, a fatty acid metal salt, an oxy fatty acid, a fatty acid amide, an alkylene bis(fatty acid) amide, a fatty acid partially saponified ester, a fatty acid alcohol ester, a fatty acid polyhydric alcohol ester, a fatty acid polyhydric alcohol partial ester, or a fatty acid polyglycol ester.

The fatty acid can have 6 to 40 carbon atoms, as exemplified by oleic acid, stearic acid, lauric acid, hyroxystearic acid, behenic acid, arachidonic acid, linoleic acid, linolenic acid, recinoleic acid, palmitic acid, montanic acid, or a combination thereof. An alkali metal salt or an alkaline earth metal salt of a fatty acid having 6 to 40 carbon atoms can be the fatty acid metal salt, as exemplified by calcium stearate, sodium montanate, or calcium behenate. The oxy fatty acid includes 1,2-oxystearic acid and the like. Fatty acid esters include a stearic acid ester, oleic acid ester, linoleic acid ester, linolenic acid ester, adipic acid ester, behenic acid ester, arachidonic acid ester, montanic acid ester, isostearic acid ester, and the like. The fatty acid partially saponified esters include, e.g., montanic acid partially saponified esters.

In an embodiment, the second substrate is a fatty acid amides having 6 or more carbon atoms, as exemplified by aleinic acid amide, erucic acid amide, and behenic acid amide. The alkylene bis(fatty acid) amide can have, e.g., 6 or more carbon atoms, as exemplified by methylene bis (stearic acid) amide, ethylene bis(stearic acid) amide, and N,N-bis(2-hydroxyethyl)stearic acid amide. Fatty acid esters having 6 or more carbon atoms include ethyl stearate, butyl stearate, ethyl behenate, stearyl stearate, stearyl oleate, and the like.

The fatty acid polyhydric alcohol esters include glycerol tristearate, glycol distearate, glycerol monostearate, pentaerythritol tetrastearate, pentaerythritol tristeareate, pentaerythritol dimyristate, pentaerythritol monostearate, pentaerythritol adipate stearate, and sorbitan monobehenate. The fatty acid polyglycol esters include polyethylene glycol fatty acid esters and polypropylene glycol fatty acid esters.

In some embodiments, the second substrate is fluorescent, luminescent, phosphorescent, chemiluminescent, or chromagenic compound molecule. Such compounds that may be used include a variety of organic or inorganic small molecules commonly referred to as a dye, label, or indicator. Examples include a fluorescein, a rhodamine, an oxazine, an acridine dye, a cyanine dye, and the like, particularly fluorescein diphosphate (tetraammonium salt), fluorescein 3'(6')-O-alkyl-6'(3')-phosphate, 9H-(1,3-dichloro-9,9-dimethylacridin-2-one-7-yl)phosphate (diammonium salt), 4-methylumbelliferyl phosphate, resorufin phosphate, 4-trifluoromethylumbelliferyl phosphate, umbelliferyl phosphate, 3-cyanoubelliferyl phosphate, 9,9-dimethylacridin-2-one-7-yl phosphate, 6,8-difluoro-4-methylumbelliferyl phosphate, and derivatives thereof. According to an embodiment, such compounds contain an OH or NH group, which participates in a hydrolysis reaction with the first substrate in the formation of the nucleotide analog.

In some embodiments, the second substrate is a small molecule having, e.g., an OH, NH, or SH group available for reaction with the first substrate. In addition to the OH, NH, or SH group, such small molecules also can include another functional group such as a hydroxyl, amino, thio, aldehyde, ketone, or carboxyl group, carboxylic ester, imide ester, orthoester, carbonate, isocyanate, isothiocyanate, aldehyde, ketone, thione, alkenyl, acrylate, methacrylate, acrylamide, sulfone, maleimide, disulfide, iodo group, epoxy, sulfonate, thiosulfonate, silane, alkoxysilane, and halosilane.

As disclosed above, an enzyme catalyzes the reaction between the first substrate and second substrate to form the nucleotide analog. In an embodiment, the enzyme includes a protein having an amino acid sequence with a homology of greater than or equal to 25%, specifically greater than or equal to 30%, more specifically greater than or equal to 50%, further specifically greater than or equal to 70%, further specifically greater than or equal to 80%, further specifically greater than or equal to 90%, and further specifically greater than or equal to 95% compared to a first amino acid sequence comprising

```
                                            (SEQ ID NO: 1)
MSKLLREVTPEERRLYYSGEWDAKKLPEFIVESIERREFGFDHTGEGPSD

RKNAFSDVRDLEDYIRATAPYAAYSSVAFYRNPQEMEGWLGAELVFDIDA

KDLPLRRCQNEHPSGQVCPICLEDAKELARDTLIILKEDFGFENIHVVYS

GRGYHIRVIDEWALKLDSKARERILSYVSAAEEVTFDDIQKRYIMLSSGY

FRVFRLRFGYFIQRINENHLKNIGLKRSTAEKLLDEKTRQDIVEKFVNKG

LLAAFPEGVGYRTLLRLFGLSTTFSKAYFDGRVTVDLKRILRLPSTLHSK

VGLVATYIGSDEKRLEKFDPFKDAVPEFRKEEVQKAYQEWKELHEG.
```

In some embodiments, the enzyme is a synthetic, recombinant, gene-activated, or natural (i.e., from a natural source) enzyme. As such, the enzyme can be a wild type or a modified enzyme. Natural sources include, e.g. a microbial source (bacteria, archaea, or fungi) or a plant cell. The enzyme may be derived by isolation from an organism, purified, or used as a cell lysate. In an embodiment, the enzyme is used as a purified recombinant protein. In certain embodiments, the enzyme is from a member of the domain archaea.

An exemplary source of the enzyme is a primase that has catalytic activity for coupling the first substrate and the second substrate to form the nucleotide analog. Archaea and eukaryotic organisms have primases that contain a small catalytic subunit that associates with a larger subunit to form a complex. The usual function of these primases is to form an oligonucleotide primer when acting on a nucleic acid strand. Although eukaryotic primases cannot initiate growth of oligonucleotide chains with deoxyribonucleoside triphosphates (dNTPs), a number of archaeal primase complexes initiate chain growth with dNTPs. Moreover, it has been discovered that the enzyme herein (namely, the enzyme with the above first amino acid sequence or the defined homology to the first amino acid sequence) not only produces oligonucleotides from dNTPs but also does so with ribonucleoside triphosphates (NTPs). Further, the enzyme herein, apart from making an oligonucleotide primer chain, has been found to catalyze the formation of the nucleotide analog by catalyzing reaction between the first substrate and the second substrate. According to an embodiment, the enzyme catalyzes production of glycerol-deoxyriboadenosine monophosphate (glycerol-dAMP) and Tris-deoxyriboadenosine monophosphate (Tris-dAMP) from deoxyriboadenosine triphosphate (dATP).

In an embodiment, the enzyme is an Archaeal primase. Archaea is a domain of unicellular organisms. As used herein, "archaeal" refers to an organism or a primase from an organism of the domain Archaea. Many species of Archaea are adapted to extreme environmental conditions and include thermophilic organisms, psychorphilic, acidophiles, alkalophiles, halophiles, and methanogens (methane producing organisms) such that an archaeal primase retains its catalytic activity under these conditions in a native archaeal organism, when extracted from an archaeal organism, or produced synthetically or recombinantly. Without wishing to be bound by theory, archaea have primases containing a small catalytic subunit that associates with a larger subunit to form a complex or a primase composed of both subunits encoded on one polypeptide chain, e.g, nanoarcheon. We have discovered the small subunit of the archaeal primase functions alone to produce the nucleotide analog from the first substrate and the second substrate. Therefore, in an embodiment, the enzyme has the first amino acid sequence (or a sequence having the homology defined above), which is a small subunit. In another embodiment, the enzyme comprises a complex that includes a small subunit comprising the first amino acid sequence (or a sequence having the homology defined above) and a large subunit. According to an embodiment, the large subunit of the enzyme is a protein having a second amino acid sequence comprising an amino acid sequence with a homology of at least 30% compared to an amino acid sequence comprising

```
                                            (SEQ ID NO: 2)
MLDPFGKRAESLIREEFGDLLALLERVPSAISVEEPISLVSWMLESENPP

QELVEVDNLEELRDLFKFYALLGAASISPYGLEAEVVKRATLRLYSERIK

ASKNLSETMLPVVPVGENEIPHNDLNILERRMDRNLSPEEKEKLKIKYKI

PIKDLLNLWGSSLKEVYIRNGYAYLRWETALKMWEKAFEKRFERAVNILY

EYRDELPEFYHRLREKLEEIAEEYFKERGEMFKGTASPLRFDLFPPCVKE
```

```
-continued
ALKGVPAGMRNYAITVLLTSFLSYARICPNPPKKDVRIKDCINDLKIIEE

EILPVIIEAGNRCKPPLFEDQPHEIKNIWYHLGFGLTDSPTMEDSGNSTW

YFPPNCDKIRANAPQLCKPDKYCRGIKNPLSYYLKRLYLEGKKKEGET

SE.
```

In an embodiment, the second amino acid sequence is from natural, recombinant, or synthetic source.

It is contemplated that the enzyme is from an archaea genus. Exemplary, archaea genera include *Acidianus, Acidilobus, Acidococcus, Aciduliprofundum, Aeropyrum, Archaeoglobus, Bacilloviridae, Caldisphaera, Caldivirga, Caldococus, Cenarchaeum, Desulfurococcus, Ferroglobus, Ferroplasma, Geogemma, Geoglobus, Haladaptaus, Halalkalicoccus, Haloalcalophilium, Haloarcula, Halobacterium, Halobaculum, Halobiforma, Halococcus, Haloferax, Halogeometricum, Halomicrobium, Halopiger, Haloplanus, Haloquadratum, Halorhabdus, Halorubrum, Halosarcina, Halosimplex, Halostagnicola, Haloterrigena, Halovivax, Hyperthermus, Ignicoccus, Ignisphaera, Metallosphaera, Methanimicrococcus, Methanobacterium, Methanobrevibacter, Methanocalculus, Methantxaldococcus, Methanocella, Methanococcoides, Methanococcus, Methanocorpusculum, Methanoculleus, Methanofollis, Methanogenium, Methanohalobium, Methanohalophilus, Methanolacinia, Methanolobus, Methanomethylovorans, Methanomicrobium, Methanoplanus, Methanopyrus, Methanoregula, Methanosaeta, Methanosalsum, Methanosarcina, Methanosphaera, Melthanospirillum, Methanothermobacter, Methanothermococcus, Methanothermus, Methanothrix, Methanotorris, Nanoarchaeum, Natrialba, Natrinema, Natronobacterium, Natronococcus, Natronolimnobius, Natronomonas, Natronorubrum, Nitracopumilus, Palaeococcus, Picrophilus, Pyrobaculum, Pyrococcus, Pyrodictium, Pyrolobus, Staphylothermus, Stetteria, Stygiolobus, Sulfolobus, Sulfophobococcus, Sulfurisphaera, Thermocladium, Thermococcus, Thermodiscus, Thermofilum, Thermoplasma, Thermoproteus, Thermosphaera, Vulcanisaeta*, and the like.

Exemplary archaeal species from which the enzyme may be derived from include *Aeropyrum pernix, Archaeglobus fulgidus, Archaeoglobus fulgidus, Desulforcoccus* species TOK, *Methanobacterium thermoantorophicum, Methanococcus jannaschii, Pyrobaculum aerophilum, Pyrobaculum calidifontis, Pyrobaculum islandicum, Pyrococcus abyssi, Pyrococcus* GB-D, *Pyrococcus glycovorans, Pyrococcus horikoshii, Pyrococcus* spp. GE23, *Pyrococcus* spp. ST700, *Pyrococcus woesii, Pyrodictium occultum, Sulfolobus acidocaldarium, Sulfolobus solataricus, Sulfolobus tokodalii, Thermococcus aggregans, Thermococcus barossii, Thermococcus celer, Thermococcus fumicolans, Thermococcus gorgonarius, Thermococcus hydrothermalis, Thermococcus onnurineus* NA1, *Thermococcus pacificus, Thermococcus profundus, Thermococcus siculi, Thermococcus* spp. GE8, *Thermococcus* spp. JDF-3, *Thermococcus* spp. TY. *Thermococcus thioreducens, Thermococcus zilligti, Thermoplasma acidophilum, Thermoplasma volcanium, Acidianus hospitalis, Acidilobus sacharovorans, Aciduliprofundum boonei, Aeropyrum pernix, Archaeoglobus fulgidus, Archaeoglobus profundus, Archaeoglobus veneficus, Caldivirga maquilingensis, Candidatus Korarchaeum cryptofilum, Candidatus Methanoregula boonei, Candidatus Nitrosoarchaeum limnia, Cenarchaeum symbiosum, Desulfurococcus kamchatkensis, Ferroglobus placidus, Ferroplasma acidarmanus, Halalkalicoccus jeotgali, Haloarcula hispanica, Holoarcula marismortui, Halobacterium salinarum, Halobacterium* species, *Halobiforma lucisalsi, Haloferax volvanii, Halogeometricum borinquense, Halomicrobium mukohataei, halophilic archaceon* sp. DL31, *Halopiger xanaduensis, Haloquadratum walsbyi, Halorhabdus tiamatea, Halorhabdus utahensis, Halorubrum lacusprofundi, Haloterrigena turkmenica, Hyperthermus butylicus, Igniococcus hospitalis, Ignisphaera aggregans, Metallosphaera cuprina, Metallosphaera sedula, Methanobacterium* sp. AL-21, *Methanobacterium* sp. SWAN-1, *Methanobacterium thermoautrophicum, Methanobrevibacter ruminantium, Methanobrevibacter smithii, Methanocaldococcus fervens, Methanocaldococcus infernus, Methanocaldococcus jannaschii, Methanocaldococcus* sp. FS406-22, *Methanocaldococcus vulcanius, Methanocella conradii, Methanocella paludicola, Methanocella* sp. Rice Cluster I (RC-I). *Methanococcoides burtonii, Methanococcus aeolicus, Methanococcus maripaludis, Methanococcus vannielii, Methanococcus voltae, Methanocorpusculum labreantum, Methanoculleus marisnigri, Methanohalobium evestigatum, Methanohalophilus mahii, Methanoplanus petrolearius, Methanopyrus kandleri, Methanosaeta concilii, Methanosaeta harundinacea, Methanosaeta thermophila, Methanosalsum zhilinae, Methanosarcina acetivorans, Methanosarcina barkeri, Methanosarcina mazei, Methanosphaera stadtmanae, Methanosphaerula palustris, Methanospiriullum hungatei, Mathanothermobacter marburgensis, Methanothermococcus okinawensis, Methanothermus fervidus, Methanotorris igneus, Nanoarchaeum equitans, Natrialba asiatica, Natrialba magadii, Natronomonas pharaonis, Nitrosopumilus maritimus, Picrophilus torridus, Pyrobaculum aerophilum, Pyrobaculum arsenaticum, Pyrobaculum calidifontis, Pyrobaculum islandicum, Pyrobaculum* sp. 1860, *Pyrococcus abyssi, Pyrococcus furiosus, Pyrococcus horikoshii, Pyrococcus* sp. NA42, *Pyrococcus yayanosii, Pyrolobus fumarii, Staphylothermus hellenicus, Staphylothermus marinus, Sulfolobus acidocaldirius, Sulfolobus islandicus, Sulfolobus solfataricus, Sulfolobus tokodaii, Thermococcus barophilus, Thermococcus gammatolerans, Thermococcus kodakaraensis, Thermococcus litoralis, Thermococcus onnurineus, Thermococcus sibiricus, Thermococcus* sp. 4557, *Thermococcus* sp. AM4, *Thermofilum pendens, Thermoplasma acidophilum, Thermoplasma volcanium, Thermoproteus neutrophilus, Thermoproteus tenax, Thermoproteus uzoniensis, Thermosphaera aggregans, Vulcanisaeta distributa, Vulcanisaeta moutnovskia*, and the like.

In an embodiment, the enzyme is a primase including a first subunit from an archaea, a large subunit from an archaea, or a combination thereof. In a particular embodiment, the enzyme is a primase from *Thermococcus kodakaraensis*. In some embodiments, the enzyme is a single chain encoded by a plasmid or chromosome.

According to an embodiment, the archaeal primase is a thermophile. Thermophilic archaea are classified by a temperature respective of their optimum growth. A moderate thermophile grows best in a temperature from 45° C. to 65° C.; an extreme thermophile grows best in a temperature from 65° C. to 80° C.; and a hyperthermophile grows best in a temperature greater than 80° C. An archaea that grows best in a temperature from 25° C. to 45° C. is designated as a mesophile, and an archaea that grows best in a temperature from −5° C. to 25° C. is designated as a psychrophile.

It is contemplated that a metal cation is present in an embodiment of the substrate composition. Without wishing to be bound by theory, the metal cation affects the activity of the enzyme with respect to the first substrate and the second substrate. The metal cation includes an alkaline earth metal cation (e.g., a cation of Mg, Ca, Sr, or Ba), a transition metal cation (e.g., a cation of Mn, Fe, Cr, V, Ni, Co, Cu, Zn, and the like), or a combination comprising at least one of the foregoing. In some embodiments, the metal cation is $Mg^{2+}$, $Mn^{2+}$, $Mn^{3+}$, or a combination thereof. The amount of the metal cation can be selected to vary (i.e., either decrease or increase) the activity of the enzyme. In an embodiment, the metal cation is present in an amount effective so that the enzyme is active with respect to catalyzing formation of the nucleotide analog from the first substrate and the second substrate. In some embodiments, the amount of the metal cation is selected to optimize the activity of the enzyme so that the nucleotide analog is produced at a selected rate or in a selected total amount or concentration. Without wishing to be bound by theory, it is believed that, when the metal cation is present in the substrate composition, the metal coordinates to the phosphate groups ($P^1$, $P^2$, and $P^3$) of the first substrate to direct the first substrate binding in the active site of the enzyme.

According to an embodiment, a buffer is present in the composition. The buffer includes a compound that maintains the pH of the composition within a certain pH value range such that the pH does not vary beyond a selected pH range due to a change in a concentration in response to addition of an acid or base, evaporation or dilution of the composition, or combining the composition with some extraneous source of basic or acidic material. Exemplary buffers include Good's buffers. Good's buffers are described in N. E. Good et al., "Hydrogen Ion Buffers for Biological Research." *Biochemistry* 5, 467 (1966), which is incorporated herein by reference in its entirety. Good's buffers are typically zwitterionic buffers and have a $pK_a$ from 6.15 to 8.75 such as 2-(N-morpholino) ethanesulfonic acid (MES), N-(2-acetamido) iminodiacetic acid (ADA), piperazine-N,N'-bis(2-ethanesulfonic acid) (PIPES), N-(2-acetamido)-2-aminoethanesulfonic acid (ACES), (2-aminoethyl)-trimethyl ammonium chloride hydrochloride (Cholamine), N,N-bis(2-hydroxy-ethyl)-2-aminoethane sulfonic acid (TES), 2-[4-(2-hydroxyethyl)-1-piperazinyl]ethanesulfonic acid (HEPES), tris(hydroxymethyl)aminomethane (TRIS), N-(tri(hydroxylmethyl)methyl)glycine (Tricine), N,N-bis(2-hydroxyethyl)-glycine (Bicine), 2-(N-cyclohexylamino) ethane-sulfonic acid (CHES), and the like.

Other exemplary buffers include acetate buffer (e.g., acetic acid, sodium acetate), phosphate buffer (e.g., phosphoric acid, sodium phosphate), citrate buffer (e.g., citric acid, sodium citrate), borate buffer, tris HCL buffer (e.g., tris (hydroxylmethyl)aminomethane, hydrochloric acid). TE buffer (e.g., tris, ethylenediaminetetraacetic acid). TAE buffer (e.g., tris, acetic acid, ethylenediaminetetraacetic acid), TBE buffer (tris, boric acid, ethylenediaminetetraacetic acid), and the like. In one embodiment, the buffer is tris.

According to an embodiment, the first substrate and second substrate react, as catalyzed by the enzyme, and form the nucleotide analog. In an embodiment, the nucleotide analog has a structure of formula 28.

$R-Q^1-P^1-L-Q$            Formula 28 wherein R, $Q^1$, $P^1$, L, and Q are as defined previously. Additionally, R and $Q^1$ are from the second substrate. The first substrate $P^1$, linker L, and base Q are from the first substrate. Thus, the nucleotide analog is a product having a bond between $P^1$ from the first substrate and $Q^1$ of the second substrate. The $Q^1-P^1$ bond formation is catalyzed by the enzyme.

Consequently, in an embodiment, the nucleotide analog includes structures such as

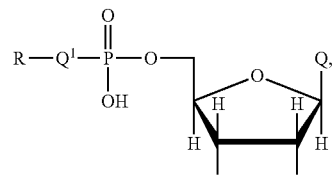

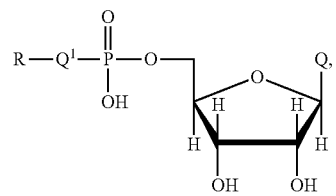

and the like.

Exemplary nucleotide analogs thus include

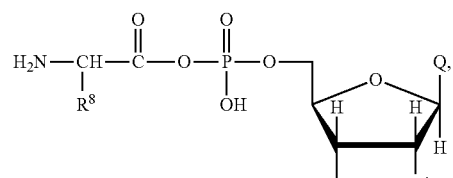

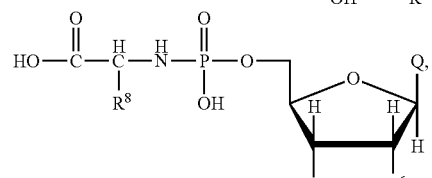

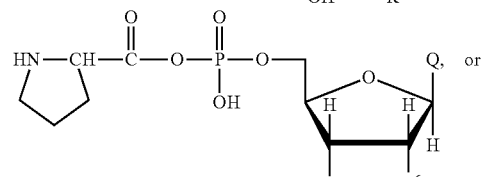

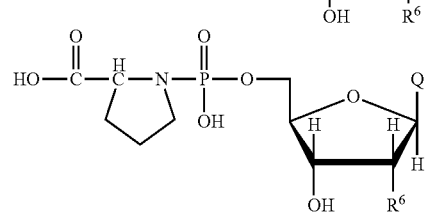

wherein $R^8$ is a functional group selected from H, $CH_3$,

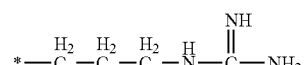

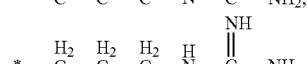

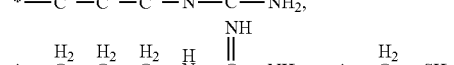

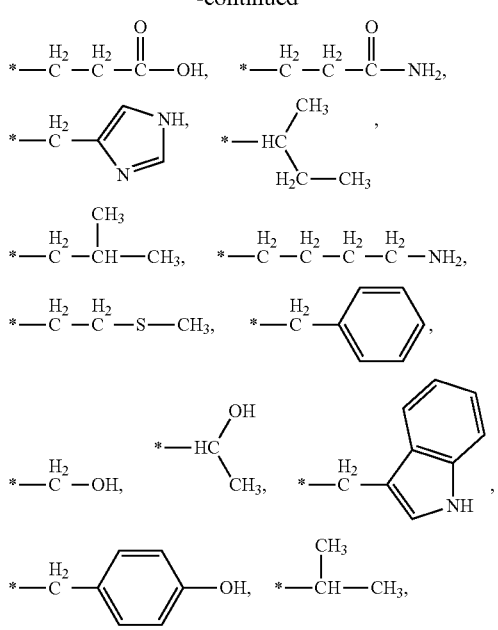
and the like.
Further exemplary nucleotide analogs include
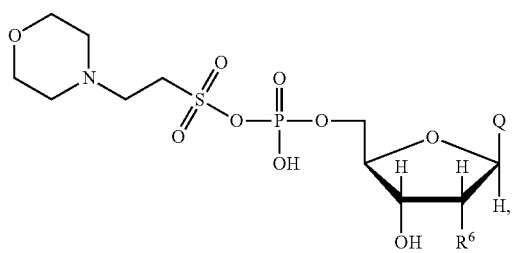
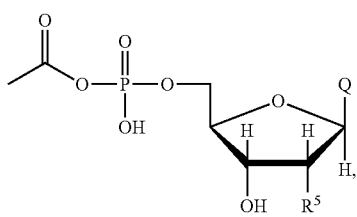
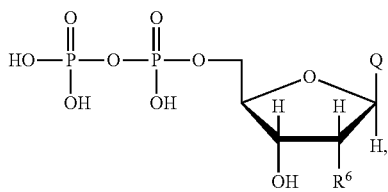
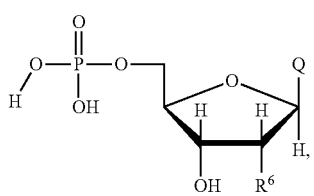
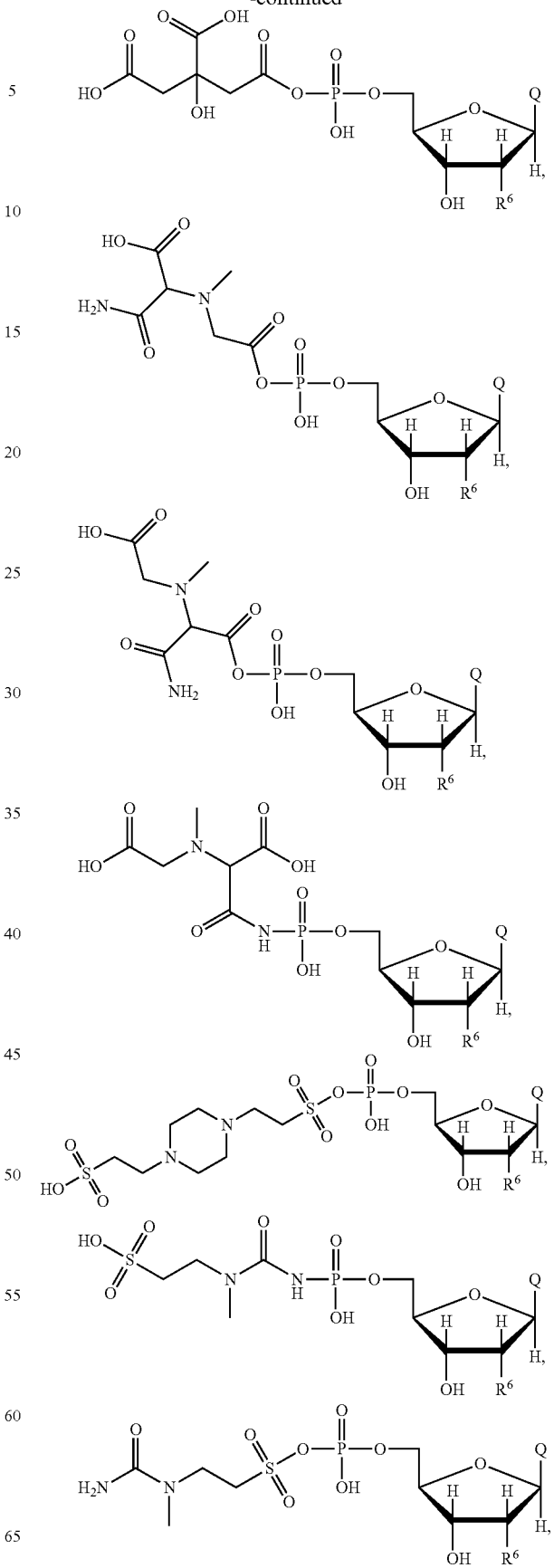

-continued
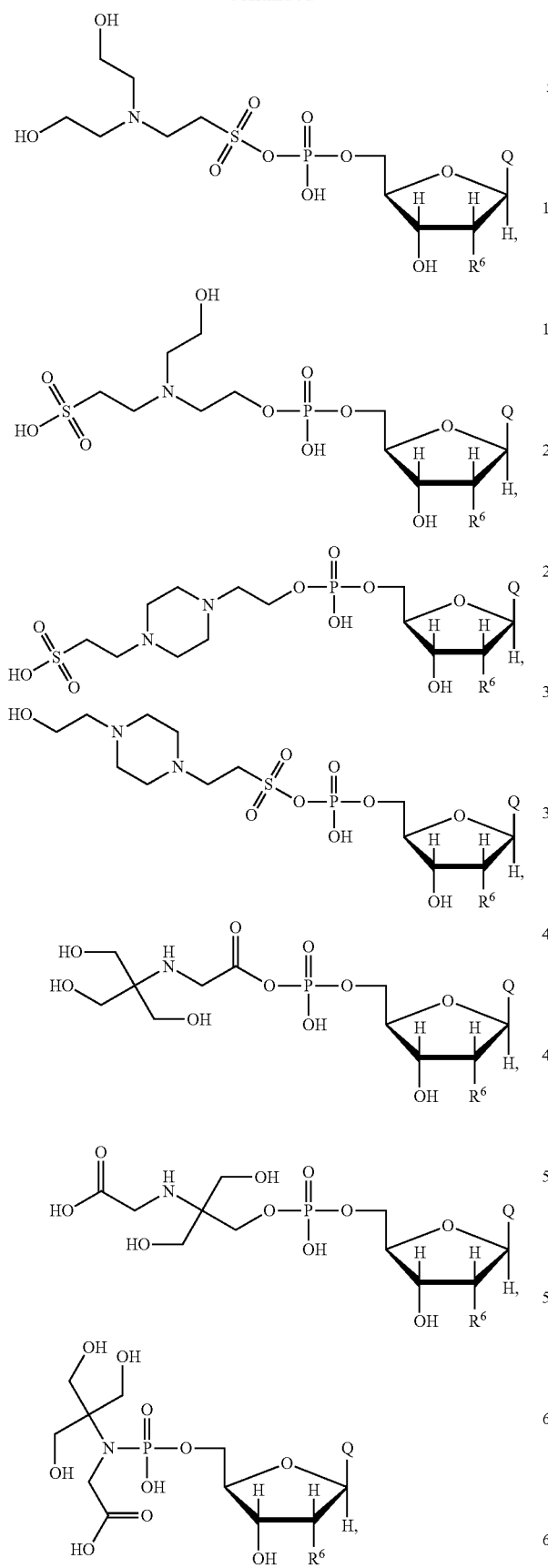
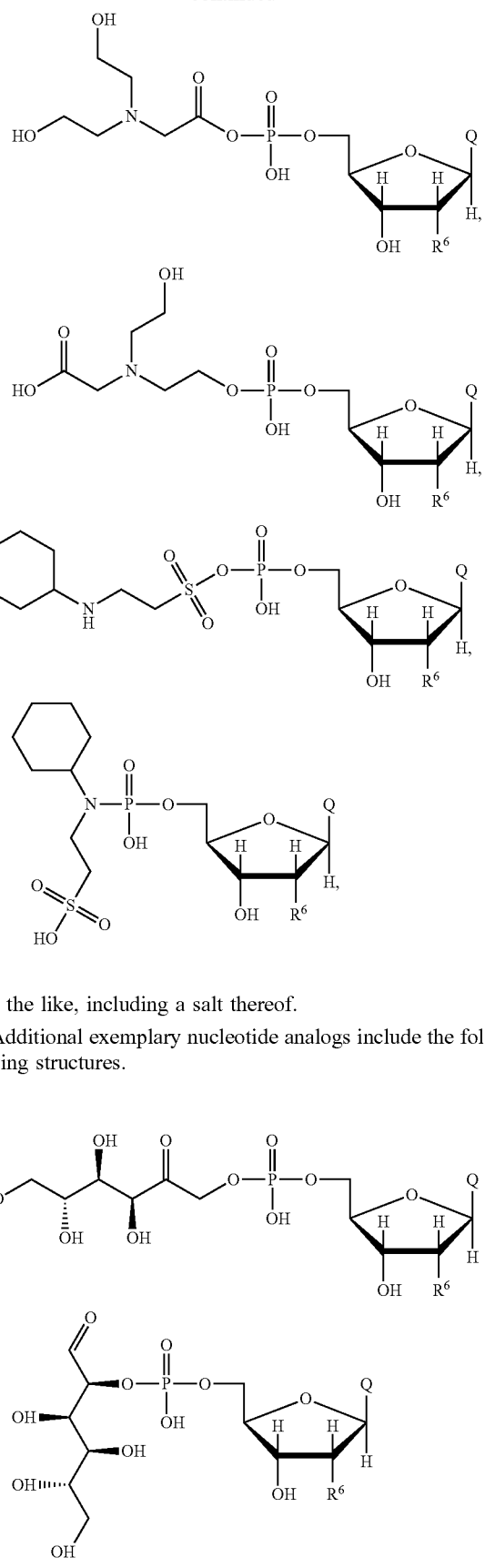
and the like, including a salt thereof.
Additional exemplary nucleotide analogs include the following structures.

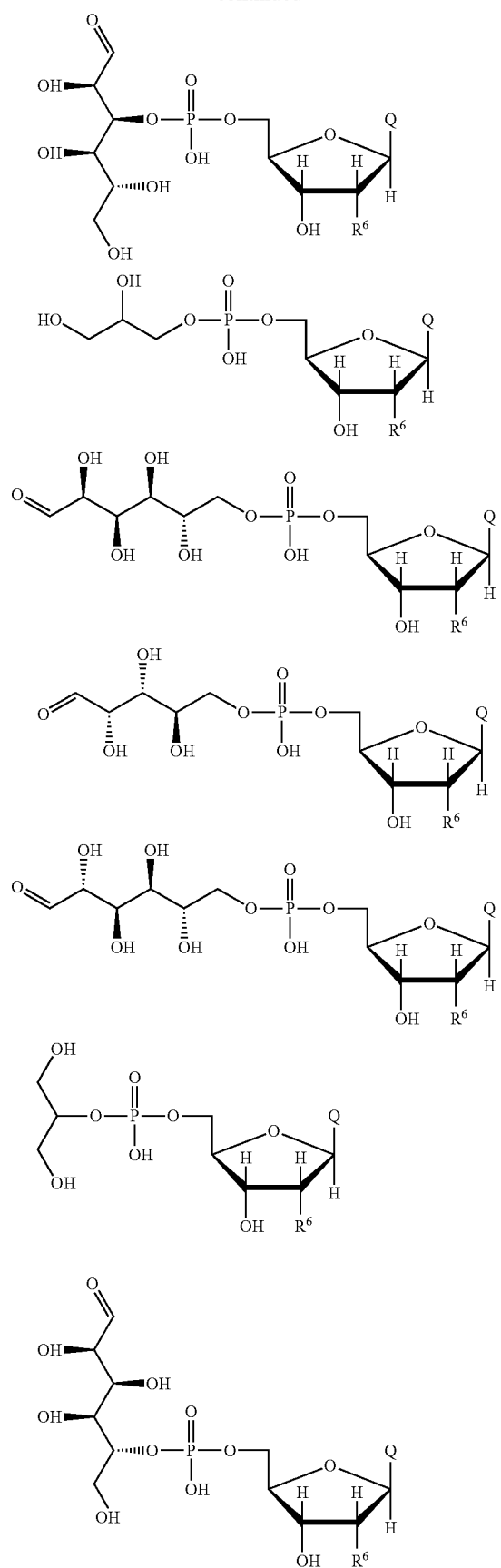
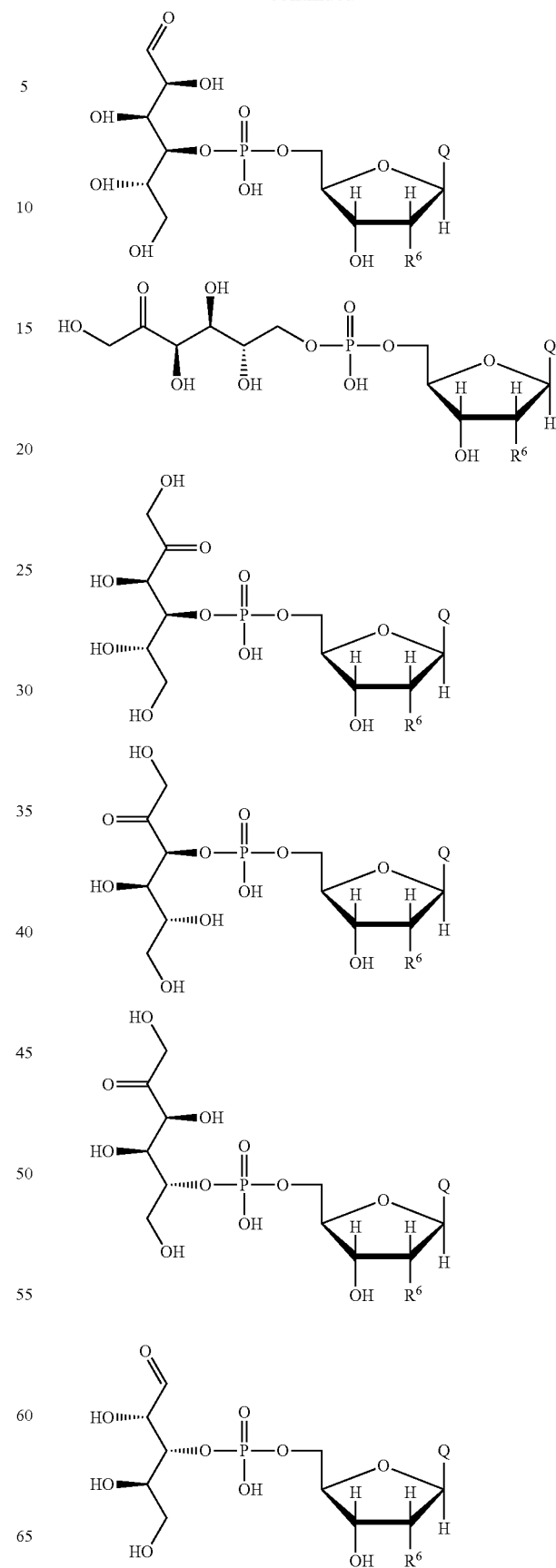

31
-continued
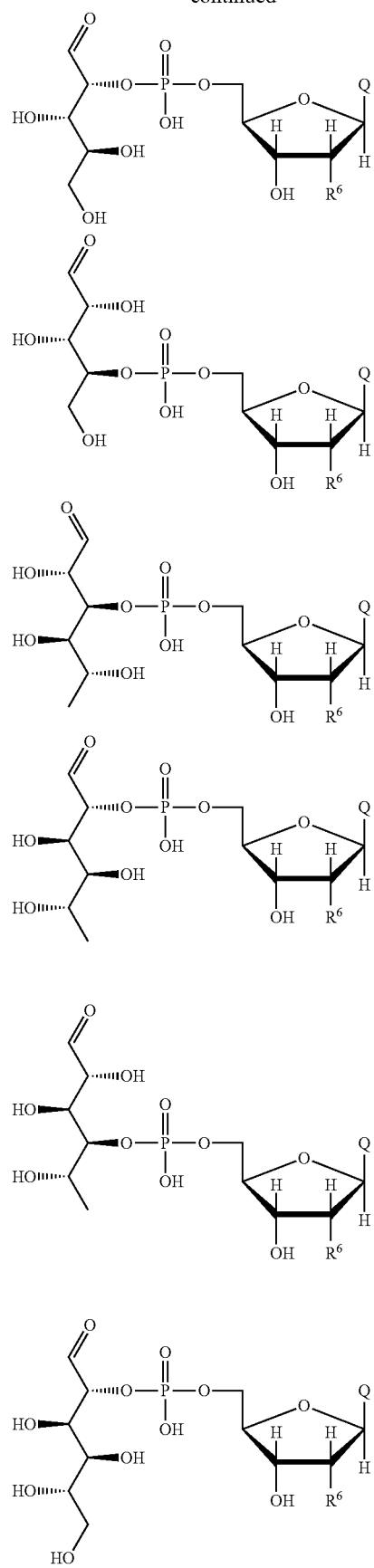
32
-continued
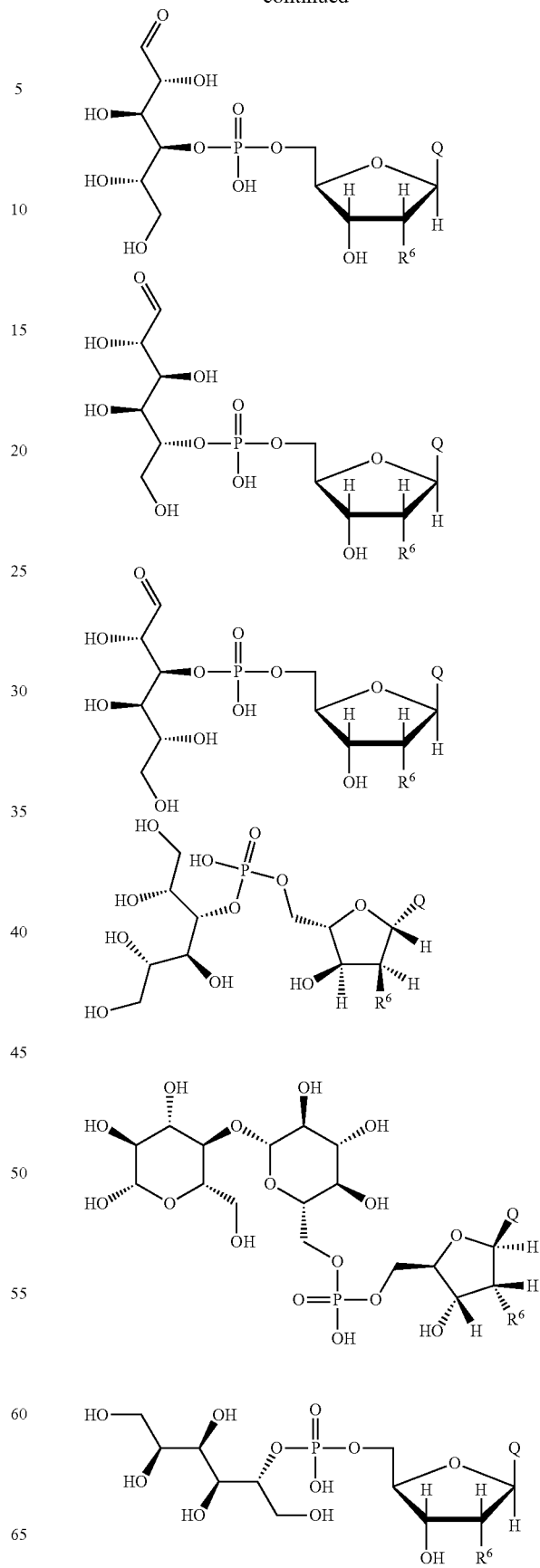

33
-continued
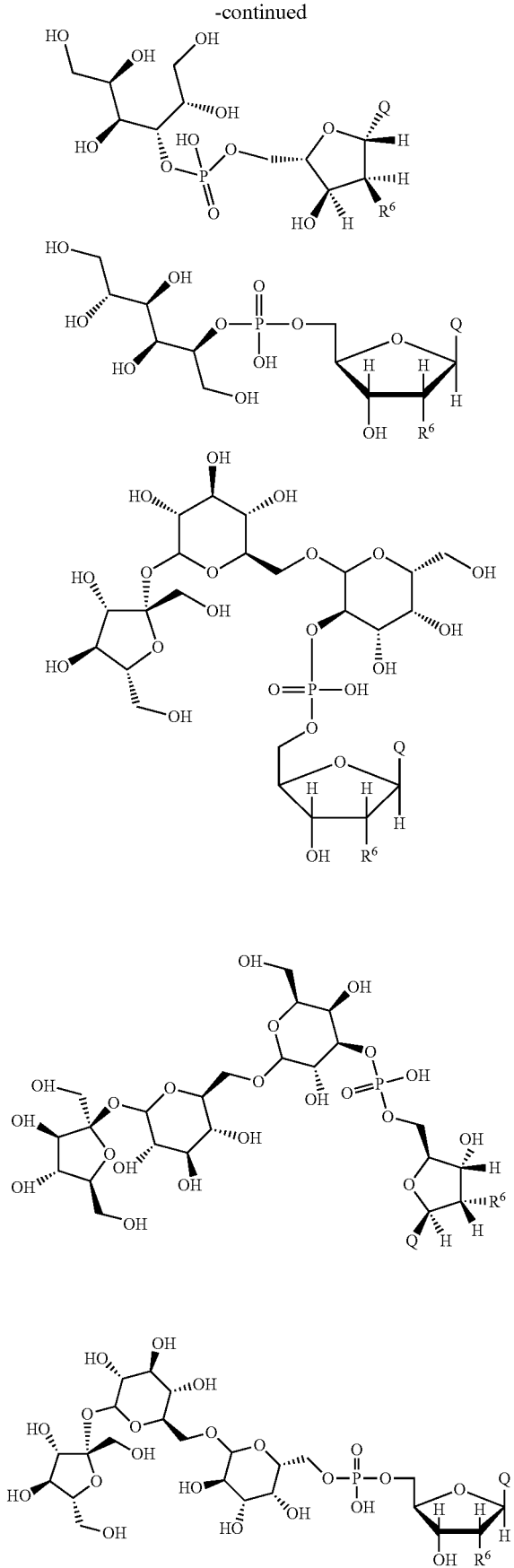
34
-continued
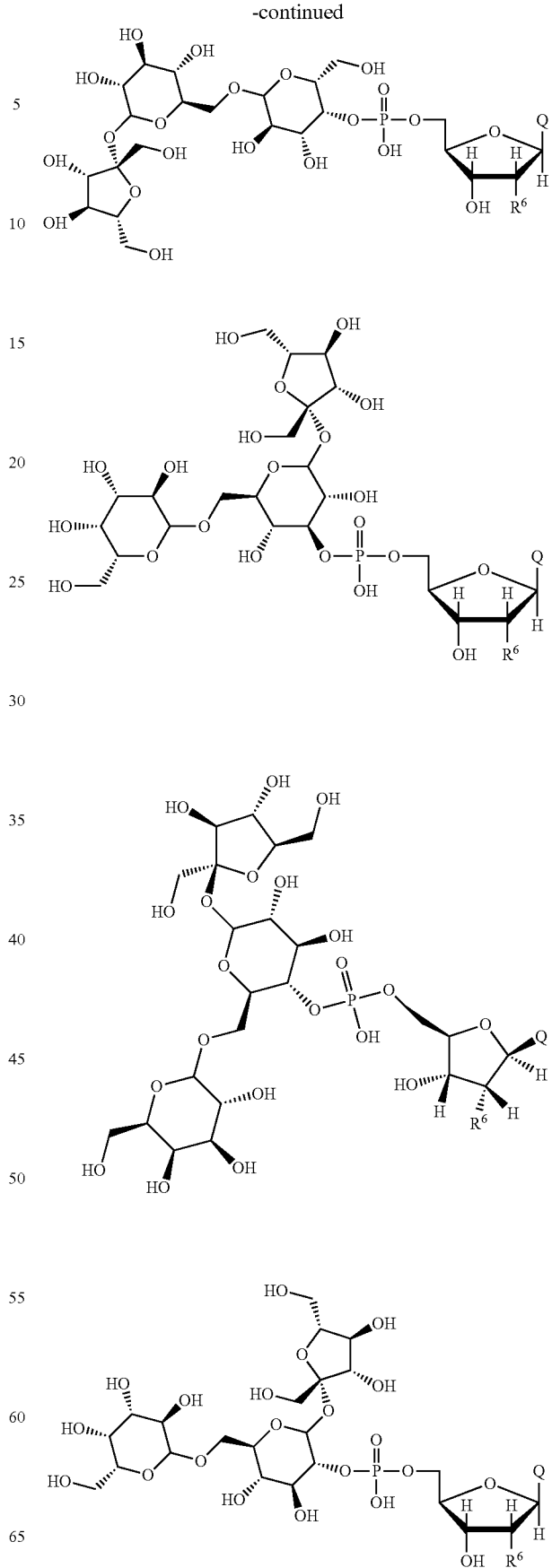

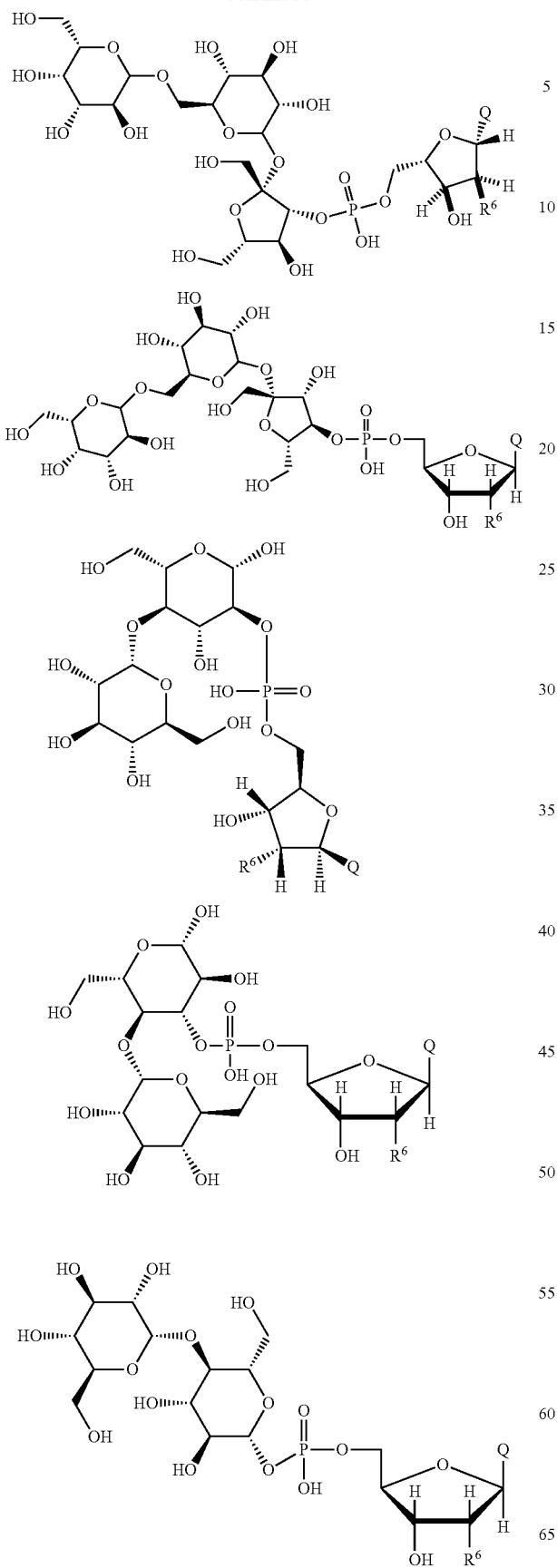
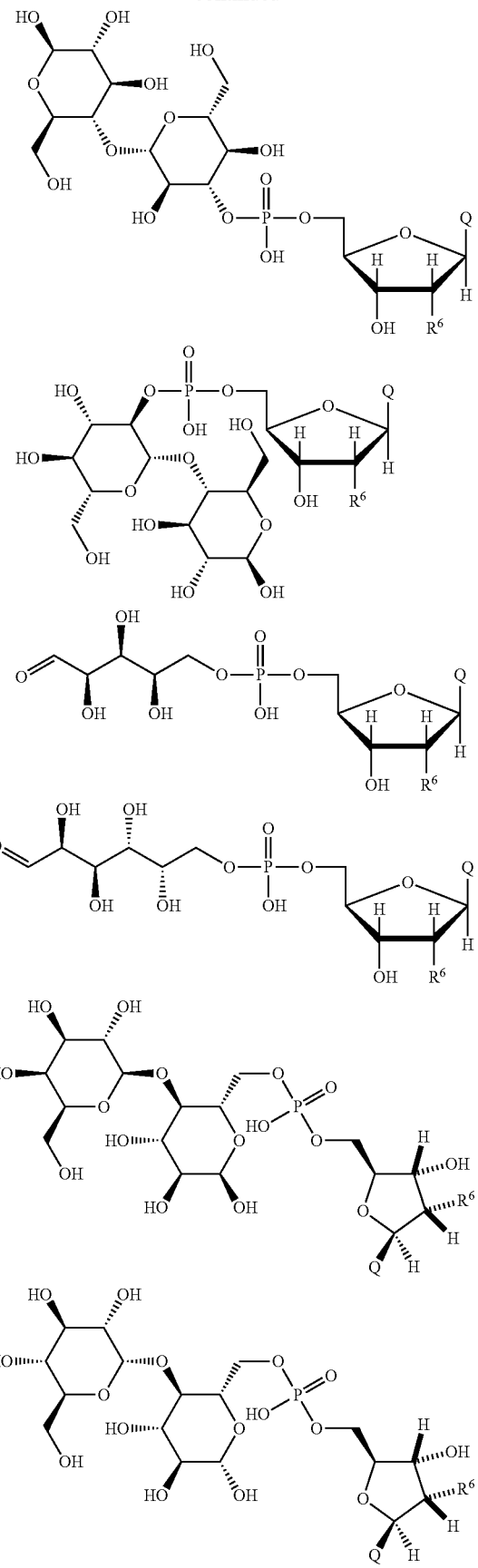

37
-continued
38
-continued
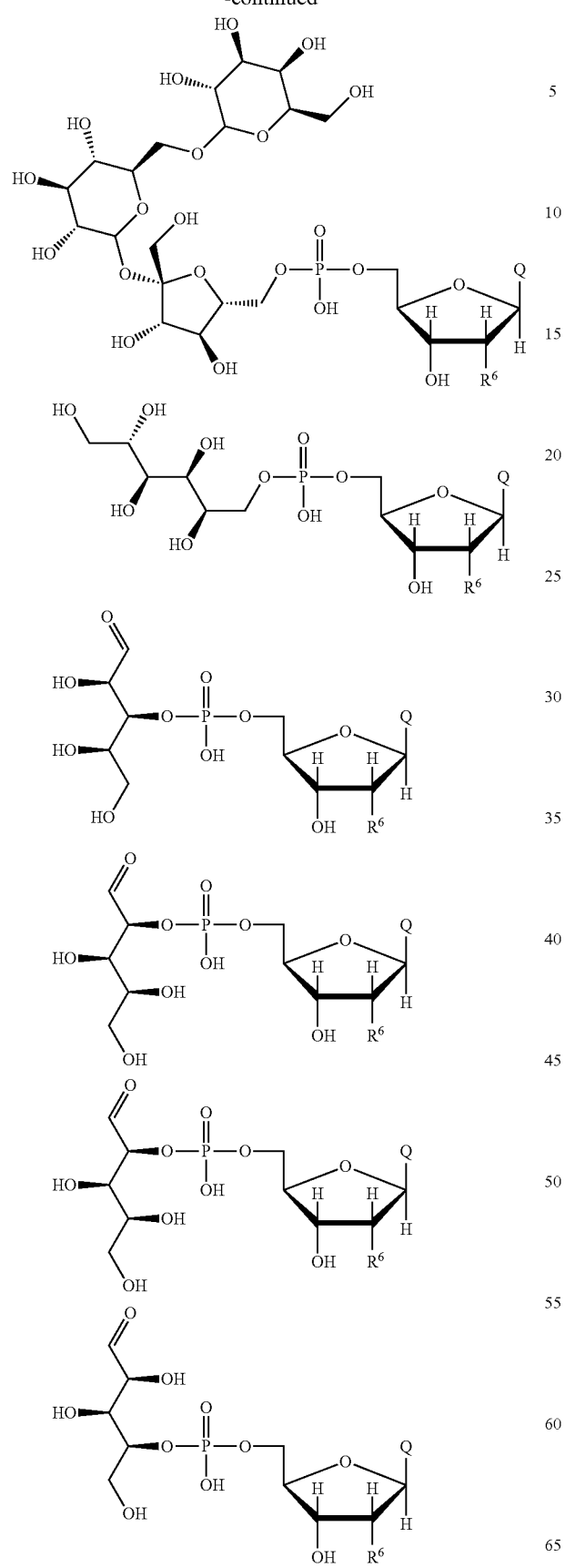
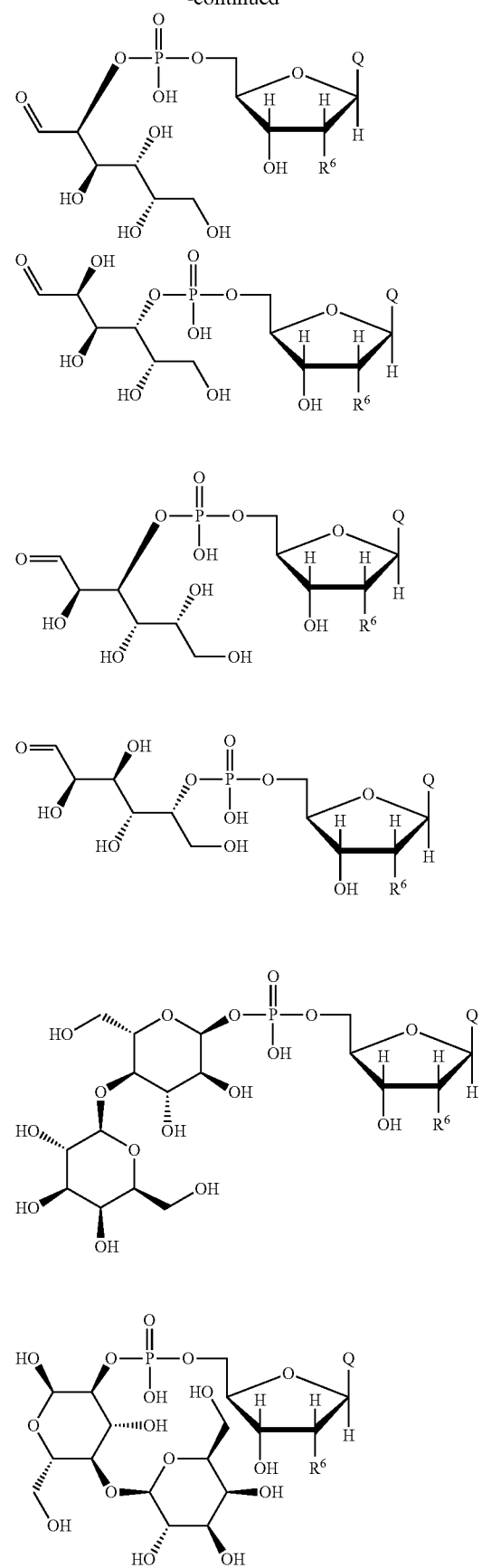

39
-continued
40
-continued
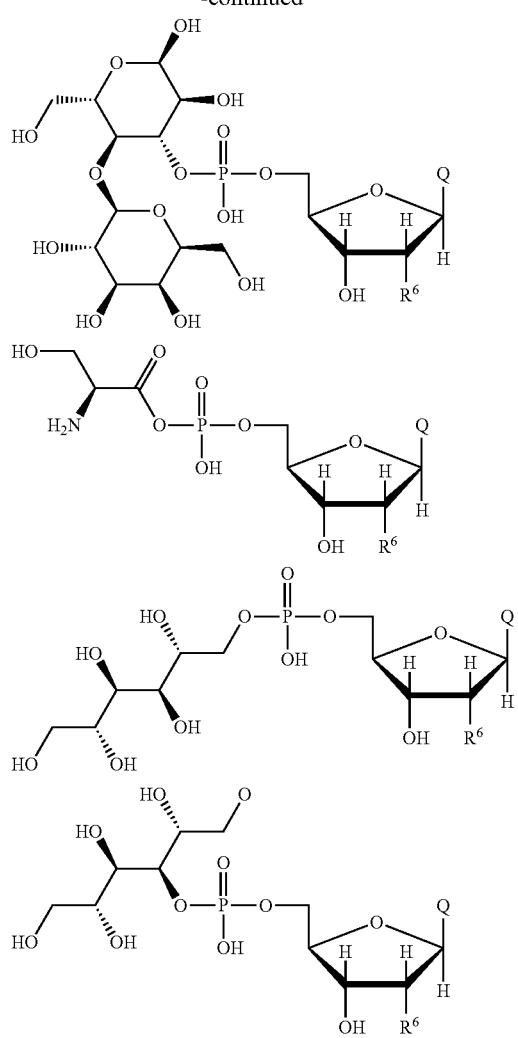
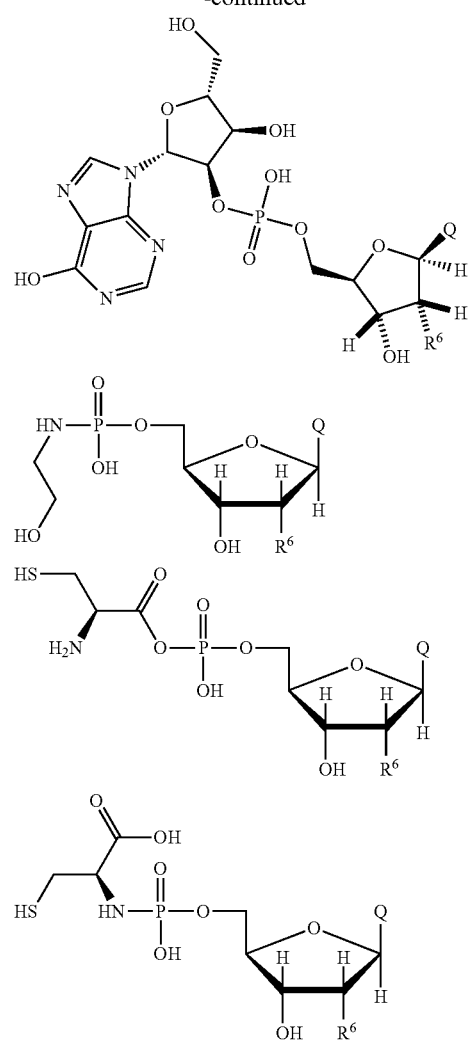
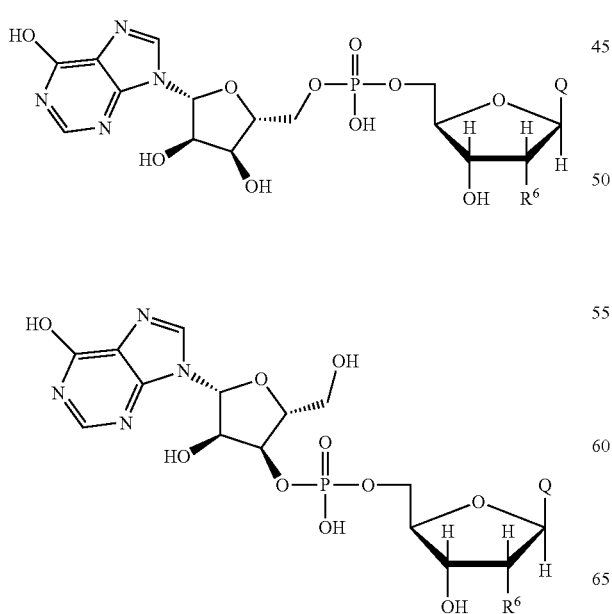

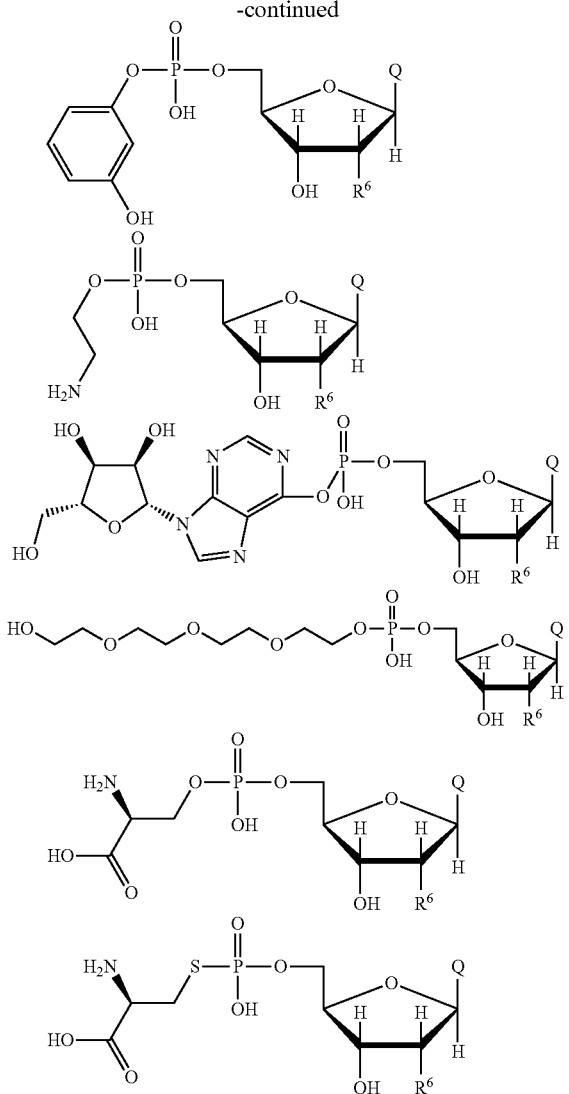

In an embodiment, an R-group, Q-group, or L-group in the first substrate, second substrate, or nucleotide analog is blocked with a protecting group. A protecting group is a species that prevents a portion of a molecule from undergoing a chemical reaction or transformation but is removable from the molecule following completion of a reaction or transformation. In an embodiment, the protecting group is removed from the first substrate, second substrate, or the nucleotide product to deprotect a protected functional group (e.g., OH). The protecting group typically is removable (and hence, labile) under conditions that do not degrade the nucleotide analog. In certain embodiments, a capping group is attached to certain functional groups of the nucleotide analog (or first substrate or second substrate). The capping group, in contrast to the protecting group, permanently binds to a portion of a target molecule and prevent further chemical transformation of that segment.

According to an embodiment, the first substrate, second substrate, or nucleotide analog includes a protecting group. Representative protecting groups are disclosed in Greene, *Protective Groups in Organic Synthesis*, 2nd ed., (John Wiley & Sons, 1991); *Oligonucleotides And Analogues A Practical Approach*, Ekstein, F. Ed. (IRL Press, N.Y., 1991); and Beaucage et al. *Tetrahedron* 48, 2223 (1992), the disclosure of each of which is incorporated herein in its entirety.

Exemplary protecting groups include Fmoc, t-butoxycarbonyl (t-BOC), 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtr), 4-methoxytrityl (Mmt), 4-methoxy-2,3,6-trimethylbenrzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl—Bzl), 2-chlorobenzyloxycarbonyl (2-Cl—Z), 2-bromobenzyloxycarbonyl (2-Br—Z), Benzyloxymethyl (Bom), cyclohexyloxy (cHxO), t-butoxymethyl (Bom), t-butoxy (tBuO), t-Butyl (tBu), Acetyl (Ac), and Trifluoroacetyl (TFA). Additional protecting groups include 2,2,5,7,8-pentamethyl-chroman-6-sulphonyl (Pmc); 2,4,5-trichlorophenyl; 2-bromobenzyloxycarbonyl (Br—Z); 2-chlorobenzyloxycarbonyl (Cl—Z); 2-nitrobenzoyl (NBz); 2-nitrophenylsulphenyl (Nps); 4-methylbenzyl (Meb); 4-nitrophenyl (ONp); 4-toluenesulphonyl (Tosyl, Tos); 9-fluorenylmethyloxycarbonyl (Fmoc); acetyl (Ac); anisyl; benzoyl (Bz); benzyl (Bzl); benzyloxycarbonyl (Z); benzyloxymethyl (Bom); diphenylmethyl (Dpm); ethyl (Et); formyl (CHO); methyl (Me); N-hydroxysuccinimide (ONSu, Osu); pentafluorophenyl (Pfp); t-butyl (t-Bu); t-butyloxycarbonyl (Boc); thioanizyl; thiocresyl; trifluoroacetyl (Tfa); triphenylmethyl (Trityl, Trt), and the like.

Exemplary hydroxyl protecting groups include acetyl, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, benzoyl, p-phenylbenzoyl, 2,6-dichlorobenzyl, diphenylmethyl, p-nitrobenzyl, triphenylmethyl (trityl), 4,4'-dimethoxytrityl, trimethylsilyl, triethylsilyl, t-butyldimethylsilyl, t-butyldiphenylsilyl, triphenylsilyl, triisopropylsilyl, benzoylformate, chloroacetyl, trichloroacetyl, trifluoroacetyl, pivaloyl, 9-fluorenylmethyl carbonate, mesylate, tosylate, triflate, trityl, monomethoxytrityl, dimethoxytrityl, trimethoxytrityl, 9-phenylxanthine-9-yl (Pixyl), or 9-(p-methoxyphenyl)xanthine-9-yl (MOX), and the like.

In an embodiment, the enzyme has catalytic activity toward forming the nucleotide analog from the first substrate and the second substrate. It is contemplated that the enzyme is active in the presence of salt at low to high concentration. Such salts include those found in naturally accruing environments such as geysers, the Great Salt Lake, the Dead Sea, the oceans, and the like. Salts include various cations, e.g., alkali metals such as potassium and sodium, alkaline earth metals such as calcium, magnesium, barium, and strontium, and the like with an anion (e.g., a halogen, formate, acetate, and the like). In some embodiments, the salt concentration is from 0 molar (M) to 6 M, specifically from 0.1 M to 5 M, and more specifically from 1 M to 4 M.

According to an embodiment, the substrate composition includes a solvent. The solvent can be selected so that the first substrate, second substrate, or enzyme have appreciable solubility in the solvent or is selected to control the available amount of the first substrate or second substrate in the solvent for forming the reaction product. In this regard, the solvent is a polar solvent (e.g., an aqueous solvent) or a nonpolar solvent. For a first substrate, second substrate, or enzyme that is hydrophobic, a polar solvent and surfactant can be included in the substrate composition so that the hydrophobic compound is available to produce the nucleotide analog.

The solvent may include polar protic solvents, polar aprotic solvents, or a combination comprising at least one of these. The solvent may include an electrolyte in the form of a salt, or a pH adjustment agent (e.g., by addition of acid or base), or a buffering agent.

An aqueous solvent is, e.g., water, and organic solvents include an alcohol (e.g. methanol, ethanol, isopropanol, and the like), dimethylsulfone, acetone, an acetate, dimethsulfoxide, dimethylformamide, γ-butyrolactone, tetrahydrofuran, propylene carbonate, ethylene glycol, an ether, an aromatic solvent (e.g. benzene, toluene, p-xylene, ethylbenzene, and the like), or a combination comprising at least one of the foregoing.

Exemplary solvents thus include water including buffered or pH adjusted water; alcohols, such as methanol, ethanol, propanol, isopropanol, butanol, t-butanol, octanol, cyclohexanol, ethylene glycol, ethylene glycol methyl ether, ethylene glycol ethyl ether, ethylene glycol butyl ether, propylene glycol, propylene glycol methyl ether, propylene glycol ethyl ether, diethylene glycol, triethylene glycol, dipropylene glycol, tripropylene glycol, cyclohexanol, and the like; polar aprotic solvents such as dimethylsulfoxide, sulfolane, ethylene carbonate, propylene carbonate, N,N-dimethylformamide, N,N-dimethylacetamide, N-methylpyrrolidone, gamma butyrolactone, and the like; or a combination comprising at least one of the foregoing solvents.

According to an embodiment, a surfactant is included in the substrate composition to disperse the first substrate or second substrate in the solvent. Useful surfactants include fatty acids of up to 22 carbon atoms such as stearic acids and esters and polyesters thereof, poly(alkylene glycols) such as poly(ethylene oxide), poly(propylene oxide), and block and random poly(ethylene oxide-propylene oxide) copolymers such as those marketed under the trademark PLURONIC by BASF. Other surfactants include polysiloxanes, such as homopolymers and copolymers of poly(dimethylsiloxane), including those having functionalized end groups, and the like. Other useful surfactants include those having a polymeric dispersant having poly(alkylene glycol) side chains, fatty acids, or fluorinated groups such as perfluorinated $C_{1-4}$ sulfonic acids grafted to the polymer backbone. Polymer backbones include those based on a polyester, a poly(meth)acrylate, a polystyrene, a poly(styrene-(meth)acrylate), a polycarbonate, a polyamide, a polyimide, a polyurethane, a polyvinyl alcohol, or a copolymer comprising at least one of these polymeric backbones. Additionally, the surfactant can be anionic, cationic, zwitterionic, or non-ionic.

Exemplary cationic surfactants include but are not limited to alkyl primary, secondary, and tertiary amines, alkanolamides, quaternary ammonium salts, alkylated imidazolium, and pyridinium salts. Additional examples of the cationic surfactant include primary to tertiary alkylamine salts such as, for example, monostearylammonium chloride, distearylammonium chloride, tristearylammonium chloride; quaternary alkylammonium salts such as, for example, monostearyltrimethylammonium chloride, distearyldimethylammonium chloride, stearyldimethylbenzylammonium chloride, monostearyl-bis(polyethoxy)methylammonium chloride; alkylpyridinium salts such as, for example, N-cetylpyridinium chloride, N-stearylpyridinium chloride; N,N-dialkylmorpholinium salts; fatty acid amide salts such as, for example, polyethylene polyamine; and the like.

Exemplary anionic surfactants include alkyl sulfates, alkyl sulfonates, fatty acids, sulfosuccinates, and phosphates. Examples of an anionic surfactant include anionic surfactants having a carboxyl group such as sodium salt of alkylcarboxylic acid, potassium salt of alkylcarboxylic acid, ammonium salt of alkylcarboxylic acid, sodium salt of alkylbenzenecarboxylic acid, potassium salt of alkylbenzenecarboxylic acid, ammonium salt of alkylbenzenecarboxylic acid, sodium salt of polyoxyalkylene alkyl ether carboxylic acid, potassium salt of polyoxyalkylene alkyl ether carboxylic acid, ammonium salt of polyoxyalkylene alkyl ether carboxylic acid, sodium salt of N-acylsarcosine acid, potassium salt of N-acylsarcosine acid, ammonium salt of N-acylsarcosine acid, sodium salt of N-acylglutamic acid, potassium salt of N-acylglutamic acid, ammonium salt of N-acylglutamic acid; anionic surfactants having a sulfonic acid group; anionic surfactants having a phosphonic acid; and the like.

The nonionic surfactant can be, e.g., ethoxylated fatty alcohols, alkyl phenol polyethoxylates, fatty acid esters, glycerol esters, glycol esters, polyethers, alkyl polyglycosides, amineoxides, or a combination thereof. Exemplary nonionic surfactants include fatty alcohols (e.g. cetyl alcohol, stearyl alcohol, cetostearyl alcohol, oleyl alcohol, and the like); polyoxyethylene glycol alkyl ethers (e.g., octaethylene glycol monododecyl ether, pentaethylene glycol monododecyl ether, and the like); polyoxypropylene glycol alkyl ethers (e.g., butapropylene glycol monononyl ether); glucoside alkyl ethers (e.g., decyl glucoside, lauryl glucoside, octyl glucoside); polyoxyethylene glycol octylphenol ethers (e.g., Triton X-100 (octyl phenol ethoxylate)); polyoxyethylene glycol alkylphenol ethers (e.g., nonoxynol-9); glycerol alkyl esters (e.g., glyceryl laurate); polyoxyethylene glycol sorbitan alkyl esters (e.g., polysorbates such as sorbitan monolaurate, sorbitan monopalmitate, sorbitan monostearate, sorbitan tristearate, sorbitan monooleate, and the like); sorbitan alkyl esters (e.g., polyoxyethylene sorbitan monolaurate, polyoxyethylene sorbitan monopalmitate, polyoxyethylene sorbitan monostearate, polyoxyethylene sorbitan monooleate, and the like); cocamide ethanolamines (e.g., cocamide monoethanolamine, cocamide diethanolamine, and the like); amine oxides (e.g., dodecyldimethylamine oxide, tetradecyldimethylamine oxide, hexadecyl dimethylamine oxide, octadecylamine oxide, and the like); block copolymers of polyethylene glycol and polypropylene glycol (e.g., poloxamers available under the trade name Pluronics, available from BASF); polyethoxylated amines (e.g., polyethoxylated tallow amine); polyoxyethylene alkyl ethers such as polyoxyethylene stearyl ether; polyoxyethylene alkylene ethers such as polyoxyethylene oleyl ether, polyoxyalkylene alkylphenyl ethers such as polyoxyethylene nonylphenyl ether; polyoxyalkylene glycols such as polyoxypropylene polyoxyethylene glycol; polyoxyethylene monoalkylates such as polyoxyethylene monostearate; bispolyoxyethylene alkylamines such as bispolyoxyethylene stearylamine; bispolyoxyethylene alkylamides such as bispolyoxyethylene stearylamide; alkylamine oxides such as N,N-dimethylalkylamine oxide; and the like Zwitterionic surfactants (which include a cationic and anionic functional group on the same molecule) include, for example, betaines, such as alkyl ammonium carboxylates (e.g., $[(CH_3)_3N^+—CH(R)COO^-]$ or sulfonates (sulfo-betaines) such as $[RN^+(CH_3)_2(CH_2)_3SO_3^-]$, where R is an alkyl group). Examples include n-dodecyl-N-benzyl-N-methylglycine $[C_{12}H_{25}N^+(CH_2C_6H_5)(CH_3)CH_2COO^-]$, N-allyl N-benzyl N-methyltaurines $[C_nH_{2n+1}N^+(CH_2C_6H_5)(CH_3)CH_2CH_2SO_3^-]$.

According to an embodiment, the first substrate, second substrate, and enzyme are present in an amount effective for reaction to occur to form the nucleotide analog.

Additives such as the buffer, surfactant, metal cation, and the like are present in the substrate composition in an amount from 0 weight percentage (wt %) to 50 wt %, specifically 0 wt % to 30 wt %, and more specifically 0 wt % to 10 wt %, based on a weight of the substrate composition.

The nucleotide analog is produced in a yield of greater than or equal to 40%, specifically greater than or equal to 60%, and more specifically from 30% to 95%, based on a weight amount of the first substrate.

In an embodiment, a process for making the nucleotide analog includes combining a first substrate includes a compound of formula 1

$$P^3-P^2-P^1-L-Q \quad \text{Formula 1}$$

with a second substrate includes a compound of formula 27

$$R-Q^1-R^5 \quad \text{Formula 27}$$

to form a substrate composition; contacting the substrate composition with an enzyme; and catalyzing, with the enzyme, formation of the nucleotide analog of formula 28 from the first substrate and the second substrate.

$$R-Q^1-P^1-L-Q \quad \text{Formula 28}$$

The enzyme includes an amino acid sequence with a homology of greater than or equal to 25%, specifically greater than or equal to 30%, more specifically greater than or equal to 50%, further specifically greater than or equal to 70%, further specifically greater than or equal to 80%, further specifically greater than or equal to 90%, and further specifically greater than or equal to 95% compared to a first amino acid sequence comprising

```
                                        (SEQ ID NO: 1)
MSKLLREVTPEERRLYYSGEWDAKKLPEFIVESIERREFGFDHTGEGPSD

RKNAFSDVRDLEDYIRATAPYAAYSSVAFYRNPQEMEGWLGAELVFDIDA

KDLPLRRCQNEHPSGQVCPICLEDAKELARDTLIILKEDFGFENIHVVYS

GRGYHIRVIDEWALKLDSKARERILSYVSAAEEVTFDDIQKRYIMLSSGY

FRVFRLRFGYFIQRINENHLKNIGLKRSTAEKLLLDEKTRQDIVEKFVNKG

LLAAFPEGVGYRTLLRLFGLSTTFSKAYFDGRVTVDLKRILRLPSTLHSK

VGLVATYIGSDEKRLEKFDPFKDAVPEFRKEEVQKAYQEWKELHEG.
```

In an embodiment, the process for making the nucleotide analog is performed in a pH from 1 to 14, specifically from 2 to 9, and more specifically from 3 to 8. Additionally, the catalyzed reaction is performed at a temperature from 4° C. to 130° C., specifically from 15° C. to 110° C., and more specifically from 20° C. to 90° C. According to some embodiments, the reaction proceeds at a pressure from subatmospheric to 5 atmospheres, specifically from atmospheric pressure to 3 atmospheres, and more specifically from atmospheric pressure to 3 atmospheres. An inert (e.g., a noble gas or N2) or reactive gas (e.g., hydrazine, oxygen, and the like) can be used to form a head pressure above the substrate composition or bubbled through the substrate composition. Likewise, other gases may be introduced or present such as $H_2S$, $CO_2$, $CO$, $NH_3$, $CH_4$, and the like. Moreover, the reaction environment for forming the nucleotide analog supports anaerobic organisms such as by an oxygen deficient or oxygen free environment.

In some embodiments, a buffer is present in the substrate composition. Alternatively, a buffer is absent in the substrate composition.

According to an embodiment, the nucleotide analog is isolated or purified. Moreover, unreacted first substrate or second substrate as well the enzyme can be isolated or purified in a manner similar to that used for the nucleotide analog. It is contemplated that nucleotide analog can be isolated or purified by a chromatographic technique such as column chromatography (e.g., flash chromatography) or HPLC, or detected by thin layer chromatography or gel electrophoresis. The nucleotide analog also can be purified and detected by liquid chromatography (LC) and mass spectrometry (MS). Preparative LC-MS is an effective method used for the purification of small organic molecules such as the compounds described herein.

In an embodiment, recrystallization of the nucleotide analog or salt thereof is performed to increase purity or increase product yield. The recrystallization solvent is selected to dissolve a moderate quantity of the nucleotide analog but is readily removed from the purified product. Other examples of purification of the nucleotide analog include sublimation, which includes a heating under vacuum, e.g. using a cold finger, and crystallization from a melt.

In some embodiments, the nucleotide analog includes optical isomers. It is contemplated that such optical isomers may be prepared from their respective optically active precursors by the procedures described above or by resolving racemic mixtures of the nucleotide analog. The resolution can be carried out in the presence of a resolving agent, by chromatography or by repeated crystallization or by some combination of these techniques. When the compounds described herein contain olefinic double bonds, other unsaturation, or other centers of geometric asymmetry, the compounds herein include, e.g. E and Z geometric isomers or cis- and trans-isomers. Likewise, all tautomeric forms can also be included.

In some embodiments, the nucleotide analog has an asymmetric center and occurs as racemates, racemic mixtures, individual diastereomers or enantiomers, with all isomeric forms being included. The nucleotide analog having a chiral center can exist in and be isolated in optically active and racemic forms. Optically active forms of the nucleotide analog can be prepared by, for example, resolution of the racemic form by recrystallization techniques, by synthesis from optically-active starting materials, or by chromatographic separation using a chiral stationary phase or by enzymatic resolution. One can either purify the respective first substrate or second substrate and then form the nucleotide analog, or purify the nucleotide analog that is formed by the enzyme.

Exemplary methods to obtain optically active nucleotide analogs include physical separation of crystals by manually separating macroscopic crystals of the individual enantiomers; simultaneous crystallization where the individual enantiomers are separately crystallized from a solution of the racemate; enzymatic resolutions where partial or complete separation of a racemate occurs by virtue of differing rates of reaction for the enantiomers with an enzyme; enzymatic asymmetric synthesis where the enzyme herein produces an enantiomerically pure or enriched enantiomer of the nucleotide analog; chiral liquid chromatography; chiral gas chromatography; extraction with chiral solvents; or transport across chiral membranes Chiral chromatography, including but not limited to simulated moving bed chromatography, is used in one embodiment. Chiral stationary phases are commercially available.

In some embodiments, the first substrate, second substrate, or nucleotide analog include a protecting group. The protecting group is removed (also referred to as deprotecting). That is, a hydroxy protecting group or an amino protecting group is removed from the first substrate, second substrate, or nucleotide analog.

Removing a hydroxy protecting group includes, e.g., treatment with an acid (e.g., for acetyl, benzyl, β-methoxyethoxymethyl ether, dimethoxytrityl, methoxymethyl ether, methoxytrityl, p-methoxybenzyl ether, methylthiomethyl ether, pivaloyl, tetrahydropyranyl, trityl, silyl ether, and ethoxyethyl ether hydroxy protecting groups), treatment with a base (e.g., for acetyl, benzoyl and pivaloyl hydroxy protecting groups), hydrogenolysis (e.g., for benzyl, benzyloxymethyl, methoxytrityl, p-methoxybenzyl ether and trityl hydroxy protecting groups), oxidation (e.g., for p-methoxybenzyl ether hydroxy protecting group), or treatment with $BBr_3$ is methylene chloride (e.g., for a methyl ether hydroxy protecting group).

In addition, removing an amino protecting group includes, e.g., treatment with an acid (e.g., for tert-butyloxycarbonyl and tosyl amino protecting groups), hydrogenolysis (e.g., for carbobenzyloxy, p-methoxybenzyl carbonyl, benzyl, p-methoxybenzyl, and 3,4-dimethoxybenzyl amino protecting groups), treatment with a base (e.g., for 9-fluorenylmethyloxycarbonyl, acetyl, and benzoyl amino protecting groups), or treatment with ammonium cerium nitrate (e.g., for p-methoxyphenyl amino protecting group).

In an embodiment, making the reaction product includes introducing the substrate composition and enzyme in, e.g., a well of a multi-well plate. The enzyme catalyzes formation of the nucleotide analog from the first substrate and the second substrate in the wells of the plate. It is contemplated that a different combination of first substrate, second substrate, or enzyme along with other components (e.g., metal cation, solvent, and the like) are present in different wells of the plate. In this manner, different wells produce different nucleotide analogs. Further, the resulting nucleotide analog is analyzed to determine the identity of the nucleotide analog per well. This is performed by manual sampling or autosampling of the composition in the wells. In this manner, many nucleotide analogs are made simultaneously and numerous reaction conditions and combinations of first substrates, second substrates, and enzymes are investigated.

According to an embodiment, the first substrate, second substrate, or enzyme is immobilized on a solid phase support before forming the nucleotide analog. Accordingly, the nucleotide analog when formed is attached to the solid phase support. Alternatively, the nucleotide analog is not attached to the solid phase support. In some embodiments, some nucleotide analog is attached to the solid phase support and some nucleotide analog is not attached to the solid phase support.

Any solid phase support is used for immobilization provided that the first substrate, second substrate, or enzyme can be coupled to the solid phase support. In some embodiments, the solid phase support is selected so that the first substrate, second substrate, and enzyme attaches to the solid phase support in a configuration so as not to block production of the reaction product. In an embodiment, the solid phase support is selected so that the first substrate, second substrate or enzyme attaches to the solid phase support such that enzyme active site is blocked or the first substrate or second substrate are unavailable to form the reaction product. Here, the formation of the nucleotide analog is modulated by releasing the enzyme, first substrate, or second that was attached to the solid phase support so that the nucleotide analog is formed. In some embodiments, the first substrate, second substrate or enzyme remain attached after the nucleotide analog is formed. In some embodiments, the first substrate, second substrate or enzyme is released from the solid phase support after the nucleotide analog is formed.

Exemplary solid phase supports include Merrifield resins, ArgoGel (available from Argonaut, San Francisco, Calif.), Sasrin resin (a polystyrene resin available from Bachem Bioscience, Switzerland), TentaGel S AC, TentaGel PHB, or TentaGel S $NH_2$ resin (polystyrene-polyethylene glycol copolymer resins available from Rappe Polymere, Tubingen, Germany). Alternatively, contemplated solid supports may also include glass, quartz, or ceramic as well as a polymer coated metal or plastic support. Another preferred solid support comprises a soluble polymer support fabricated by, e.g., copolymerization of polyethylene glycol, polyvinylalcohol, or polyvinylalcohol with polyvinyl pyrrolidine or derivatives thereof.

Coupling the first substrate, second substrate or enzyme to the solid phase support generally depends on the type of solid phase support in relation to the first substrate, second substrate or enzyme. Non-limiting coupling methods are described in *Organic Synthesis on Solid Phase*, F. Z. Dorwald et al., (John Wiley & Sons; ISBN: 3527299505) and *Solid-Phase Synthesis Combinatorial Technologies*, P. Seneci, (John Wiley & Sons; ISBN: 0471331953), which are incorporated by reference herein in their entirety.

The process for forming the nucleotide analog is efficient, robust, and comports with green chemistry principles (such as producing little or no waste). Furthermore, the reaction is a one-pot, one-step, high-yield reaction. Since, e.g. archaea survive and thrive over a diverse temperature, pressure or pH range, the nucleotide analog can be produced over a large range of temperatures, pressures, or pH values as well as salinity concentrations. Moreover, the reaction is applicable to multi-well plates and similar arrays (e.g., a 96- or 384-well plate format) for rapid and automated screening. As such, nucleotide analogs are generated that are not easily achieved by chemical synthesis.

The nucleotide analogs herein have numerous beneficial uses. In an embodiment, the nucleotide analog is a prodrug. Such material can be used as an antibacterial, antiviral, or anticancer prodrug. Moreover, the nucleotide analogs herein are useful in treating an adverse physiological consequence of a bacteria, virus, or cancer. In another embodiment, the nucleotide analog is a feed material or foodstuff, e.g., for livestock. In a particular, embodiment, the nucleotide analog is a dNMP-amino acid adduct that is used as nutrient feed for cattle, pigs, and the like. Such animals are known to have nutrient deficiencies due to lack of bioabsorption of certain nutrients in conventional feed and nutritional supplements currently available.

Various terms are used herein. As used herein, "alkenyl" means a linear or branched chain, monovalent hydrocarbon group having at least one carbon-carbon double bond (e.g., ethenyl (—HC=$CH_2$)).

As used herein, "alkenylene" means a linear or branched chain, divalent hydrocarbon group having at least one carbon-carbon double bond (e.g., ethenylene (—HC=CH—)), optionally substituted with one or more substituents where indicated, provided that the valence of the alkyl group is not exceeded.

As used herein, "alkoxy" means an alkyl group that is linked via an oxygen (i.e., —O-alkyl). Nonlimiting examples of C1 to C30 alkoxy groups include methoxy groups, ethoxy groups, propoxy groups, isobutyloxy groups, sec-butyloxy groups, pentyloxy groups, iso-amyloxy groups, and hexyloxy groups.

As used herein, "alkoxyalkyl" means an alkyl radical substituted with one or more alkoxy groups.

As used herein, "alkyl" means a linear or branched chain, saturated, monovalent hydrocarbon group (e.g., methyl or hexyl), optionally substituted with one or more substituents where indicated, provided that the valence of the alkyl group is not exceeded. Alkyl groups include, for example, groups having from 1 to 50 carbon atoms (C1 to C50 alkyl).

As used herein, "C1 to C15 alkylamine group" is a group of the formula -Q-N(Rw)(Rz), wherein Q is a C1 to C15 alkenylene, and Rw and Rz are independently hydrogen, a C1 to C14 alkyl, a C1 to C14 alkenyl, a C1 to C14 alkynyl, a C3 to C14 cycloalkyl or a C6 to C14 aryl; such that the total number of carbon atoms in Q, Rw, and Rz is from 1 to 15.

As used herein, "alkylaryl" means an alkyl group covalently linked to a substituted or unsubstituted aryl group that is linked to a compound.

As used herein, "alkylene" means a linear or branched chain, saturated, divalent aliphatic hydrocarbon group, (e.g., methylene ($-CH_2-$) or, propylene ($-(CH_2)_3-$)).

As used herein, "alkylene" means a linear, branched or cyclic divalent aliphatic hydrocarbon group, and may have from 1 to about 18 carbon atoms, more specifically 2 to about 12 carbons. Exemplary alkylene groups include methylene ($-CH_2-$), ethylene ($-CH_2CH_2-$), propylene ($-(CH_2)_3-$), cyclohexylene ($-C_6H_{10}-$), methylenedioxy ($-O-CH_2-O-$), or ethylenedioxy ($-O-(CH_2)_2-O-$).

As used herein, "alkyne" means a linear or branched chain hydrocarbon having at least one carbon-carbon triple bond.

As used herein, "alkynyl" means a linear or branched chain, monovalent hydrocarbon group having at least one carbon-carbon triple bond (e.g., ethynyl).

As used herein, "alkynylene" means a linear or branched chain divalent aliphatic hydrocarbon that has one or more unsaturated carbon-carbon bonds, at least one of which is a triple bond (e.g., ethynylene).

As used herein, "amide" means a group of the formula $-C(O)-N(Rx)(Ry)$ or $-N-C(O)-Rx$, wherein Rx is an alkyl, an alkenyl, an alkynyl, a cycloalkyl or an aryl group; and Ry is hydrogen or any of the groups listed for Rx.

As used herein, "aryl" refers to a hydrocarbon group having an aromatic ring, and includes monocyclic and polycyclic hydrocarbons wherein the additional ring(s) of the polycyclic hydrocarbon may be aromatic or nonaromatic (e.g., phenyl or napthyl).

As used herein, "arylalkyl" means a substituted or unsubstituted aryl group covalently linked to an alkyl group that is linked to a compound (e.g., a benzyl is a C7 arylalkyl group).

As used herein, "arylalkylene" group is an aryl group linked via an alkylene moiety. The specified number of carbon atoms (e.g., C7 to C30) means the total number of carbon atoms present in both the aryl and the alkylene moieties. Representative arylalkyl groups include, for example, benzyl groups.

As used herein, "arylene" means a divalent group formed by the removal of two hydrogen atoms from one or more rings of an arene, wherein the hydrogen atoms may be removed from the same or different rings (e.g., phenylene or napthylene).

As used herein, "aryloxy" means an aryl moiety that is linked via an oxygen (i.e., $-O$-aryl).

As used herein, an asterisk (i.e., "*") denotes a point of attachment, e.g., a position linked to the same or different atom or chemical formula.

As used herein, "cycloalkylene" means a divalent radical formed by the removal of two hydrogen atoms from one or more rings of a cycloalkyl group (a nonaromatic hydrocarbon that comprises at least one ring).

As used herein, "cycloalkynyl" means an aliphatic monocyclic or polycyclic group having at least one carbon-carbon triple bond, wherein all ring members are carbon (e.g., cyclohexynyl).

As used herein, "cycloalkenylene" means an aliphatic 5-15-membered monocyclic or polycyclic, divalent radical having at least one carbon-carbon double bond, which comprises one or more rings connected or bridged together. Unless disclosed otherwise, the cycloalkenylene radical can be linked at any desired carbon atom provided that a stable structure is obtained. If the cycloalkenylene radical is substituted, this may be so at any desired carbon atom, once again provided that a stable structure is obtained. Examples thereof are cyclopentenylene, cyclohexenylene, cycloheptenylene, cyclooctenylene, cyclononenylene, cyclodecenylene, norbornenylene, 2-methylcyclopentenylene, 2-methylcyclooctenylene.

As used herein, "cycloalkyl" means a monovalent group having one or more saturated and/or partially saturated rings in which all ring members are carbon (e.g., cyclopropyl, cyclobutyl, cyclopentyl, cyclohexyl, cycloheptyl, cyclooctyl, and partially saturated variants of the foregoing, such as cycloalkenyl groups (e.g., cyclohexenyl) or cycloalkynyl groups.

As used herein, "cycloalkenyl" means a monovalent group having one or more rings and one or more carbon-carbon double bond in the ring, wherein all ring members are carbon (e.g., cyclopentyl and cyclohexyl).

As used herein, the prefix "hetero" means that the compound or group includes an atom that is a heteroatom (e.g., 1, 2, or 3 heteroatom(s)), wherein the heteroatom(s) is each independently N, O, S, Si, or P.

Reference herein is made to various heterocyclic groups. Within such groups, the term "hetero" means a group that comprises at least one ring member that is a heteroatom (e.g., 1 to 4 heteroatoms, each independently N, O, S, P, or Si). In each instance, the total number of ring members may be indicated (e.g., a 3- to 10-membered heterocycloalkyl). If multiple rings are present, each ring is independently aromatic, saturated, or partially unsaturated, and multiple rings, if present, may be fused, pendant, spirocyclic or a combination thereof. Heterocycloalkyl groups comprise at least one non-aromatic ring that contains a heteroatom ring member. Heteroaryl groups comprise at least one aromatic ring that contains a heteroatom ring member. Non-aromatic and/or carbocyclic rings may also be present in a heteroaryl group, provided that at least one ring is both aromatic and contains a ring member that is a heteroatom.

As used herein, a "heteroalkyl" group is an alkyl group that comprises at least one heteroatom covalently bonded to one or more carbon atoms of the alkyl group. Each heteroatom is independently chosen from N, O, S, Si, or P.

As used herein, "heteroarylalkyl" means a heteroaryl group linked via an alkylene moiety.

As used herein, "heteroarylene" means a divalent radical formed by the removal of two hydrogen atoms from one or more rings of a heteroaryl moiety, wherein the hydrogen atoms may be removed from the same or different rings (preferably the same ring), each of which rings may be aromatic or nonaromatic.

As used herein, "independently" indicates that the variable, which is independently applied, varies independently from application to application. Thus, in a compound such as R"XYR", wherein R" is "independently carbon or nitrogen," both R" can be carbon, both R" can be nitrogen, or one R" can be carbon and the other R" nitrogen.

As used herein, "isolated" refers to a composition that includes at least 85% to 90% by weight, specifically 95% to 98% by weight, and even more specifically, 99% to 100% by weight of a particular compound in the composition, the remainder comprising other chemical compounds.

As used herein, "substituted" means a compound or radical substituted with at least one (e.g., 1, 2, 3, 4, 5, 6 or more) substituents independently selected from a halide (e.g., F, Cl⁻, Br⁻, I⁻), a hydroxyl, an alkoxy, a nitro, a cyano, an amino, an azido, an amidino, a hydrazino, a hydrazono, a carbonyl, a carbamyl, a thiol, a C1 to C6 alkoxycarbonyl, an ester, a carboxyl, or a salt thereof, sulfonic acid or a salt thereof, phosphoric acid or a salt thereof, a $C_1$ to $C_{20}$ alkyl, a $C_2$ to $C_{16}$ alkynyl, a $C_6$ to $C_{20}$ aryl, a $C_7$ to $C_{13}$ arylalkyl, a $C_1$ to $C_4$ oxyalkyl, a $C_1$ to $C_{20}$ heteroalkyl, a $C_3$ to $C_{20}$ heteroaryl (i.e., a group that comprises at least one aromatic ring, wherein at least one ring member is other than carbon), a $C_3$ to $C_{20}$ heteroarylalkyl, a $C_3$ to $C_{20}$ cycloalkyl, a $C_3$ to $C_{15}$ cycloalkenyl, a $C_6$ to $C_{15}$ cycloalkynyl, a $C_5$ to $C_{15}$ heterocycloalkyl, or a combination including at least one of the foregoing, instead of hydrogen, provided that the substituted atom's normal valence is not exceeded.

As used herein, "extremophile" refers to an organism that exhibits optimal growth under extreme environment conditions. Extremophiles include acidophiles, alkaliphiles, halophiles, thermophiles (including hyerthermophiles and psychrophiles), metalo-tolerant organisms, osmophiles, and xerophiles.

The compositions, compounds, and methods herein are further illustrated by the following examples, which are non-limiting.

EXAMPLES

Abbreviations used below are mg=milligrams: μg=micrograms; mL=milliliter: μL=microliter; M=molar; mM=millimolar; μ=micromolar; h=hour(s); min=minute(s); DTT=dithiothreitol; BSA=Bovine Serum Albumin; PEI=polyethyleneimine P_i=phosphate; PPi=pyrophosphate; dNMP=deoxyribonucleoside monophosphate; dAMP=deoxyribonucleoside monophosphate; PriS=small subunit of primase; PriL=large subunit of primase; m=mutant (when used in context of an enzyme); M=molecular mass markers; TLC=thin layer chromatography; and NMR=nuclear magnetic resonance.

Preparation of Proteins.

*Thermococcus kodakaraensis* primase proteins were prepared and isolated as described below. All enzymes were stored at −80° C. and were stable through repeated freezing and thawing.

Expression Constructs.

The genes encoding the large subunit of primase (PriL, TK1790, p46) were amplified using PCR from the *T. kodakaraensis* genomic DNA and cloned into pET-21a (Novagen). The gene encoding the small primase subunit (PriS, TK1791, p41) was amplified using PCR from the *T. kodakaraensis* genomic DNA and cloned into pET-28a (Novagen). All constructs encode proteins containing an in-frame His6 tag at the C terminus. A variant form of PriS in which the conserved Asp-97 and Asp-99 were replaced by Ala (D97A/D99A) was generated using QuikChange (Stratagene). This variant is referred to as mutant (m) p41, and a *T. kodakaraensis* primase complex (p41-p46) containing this variant is referred to as a mutant complex (m p41-p46).

Expression and Purification of Recombinant Proteins.

For protein expression, plasmids encoding the various proteins were transformed into *E. coli* BL21 DE3 Rosetta cells (Invitrogen). Expression was induced by the addition of 0.5 mM isopropyl-1-thio-β-D-galactopyranoside when the culture reached an A600 of ~0.6 followed by incubation for 16 h at 16° C. Cells were collected by centrifugation, resuspended in buffer containing 50 mM Tris-HCl (pH 8.0), 500 mM NaCl, 10 mM imidazole, and 10% glycerol, incubated at 55° C. for 30 min, and then sonicated. The lysate was clarified by centrifugation and loaded onto a Ni2+ column (GE Healthcare). The column was washed with buffer containing 50 mM Tris-HCl (pH 8.0), 500 mM NaCl, 50 mM imidazole, and 10% glycerol. The His6-tagged proteins were eluted from the column with buffer containing 50 mM Tris-HCl (pH 8.8), 500 mM NaCl, 10% glycerol, 250 mM imidazole. Proteins were stored at −80° C.

The PriS-PriL (p41-p46) complex was made as follows. Thirty mg of purified PriS (or PriS D97A/D99A) were incubated with 36 mg of purified PriL (resulting in 1:1 molar ratio) at 25° C. for 1 h. Following incubation, the mixture was dialyzed against buffer containing 50 mM Tris-HCl (pH 8.0), 500 mM NaCl, 2 mM DTT, and 10% glycerol. An aliquot of the complex (200 μg in 200 μL) was subjected to Superdex 200 gel filtration analysis. More than 90% of the proteins were isolated as the stoichiometric p41-p46 complex.

Commercial Enzymes.

The enzymes and their sources included: spleen phosphodiesterase (46 units/mg, Amersham Biosciences); yeast inorganic pyrophosphatase and micrococcal nuclease (Worthington Biochemical) muscle myokinase, snake venom phosphodiesterase, yeast hexokinase, and calf intestinal phosphatase (CIP) (Sigma-Aldrich); and 3-phospho-glyceraldehyde dehydrogenase and 3-phosphoglycerate kinase (Roche Applied Science).

Small Scale Production of Nucleotide Analogs.

Small-scale batches of reactions were prepared to analyze production of nucleotide analogs from various starting materials. Reaction mixtures having a total volume of 20 μL and containing 2 mM DTT, 10 mM magnesium acetate, 100 μM labeled dNTP or rNTP, 50 μg/ml BSA, and 1.25 μM enzyme were incubated at 70° C. for a specified time. Typically, enzyme preparations were diluted with a solution containing 50% glycerol, 0.02 M Tris-HCl (pH 8.0), 1 mM DTT, 10 μM EDTA, and 50 μg/ml BSA (with a glycerol diluent). The reaction mixture also contained a reagent listed in Table 1. The reagent typically was present in the reaction mixture at a concentration of 40 mM. These reagents reacted with the dNTP or rNTP to form various nucleotide analogs, and exemplary nucleotide analogs also are shown in the Table 1. Although one product nucleotide analog usually is shown Table 1 for each reagent (except for Tris), other nucleotide analogs were formed from the reagents listed in Table 1 for those reagents that have more than one hydroxy (OH) group or amine (NH) group, as illustrated for Tris in Table 1. That is, each OH or NH group generally was reactive toward the dNTP or rNTP to some extent in forming a nucleotide analog.

TABLE 1
| Reagent | dNTP | Exemplary Nucleotide Analog |
|---|---|---|
| Tris | dATP | (O-Tris-dAMP) <br> (N-Tris-dAMP) |
| Glycerol | dATP | (Glycerol-dAMP) |
| Ethanolamine | dATP | |
| HEPES | dATP | |
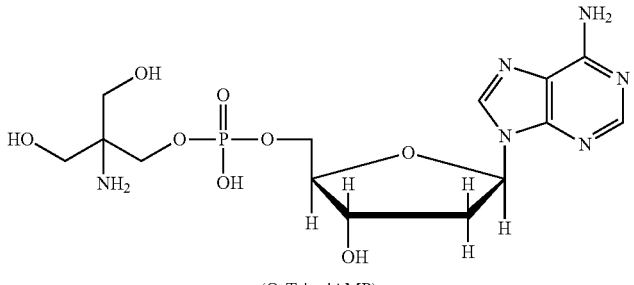
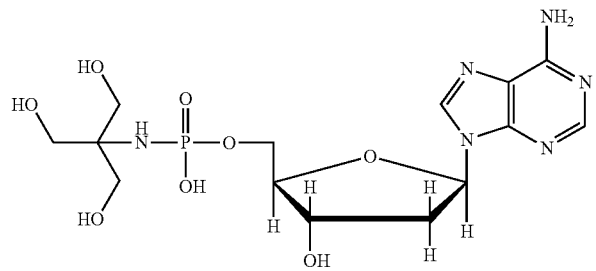
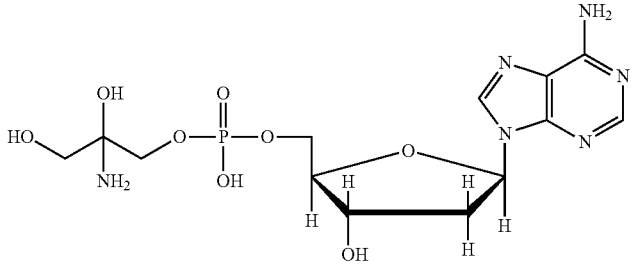
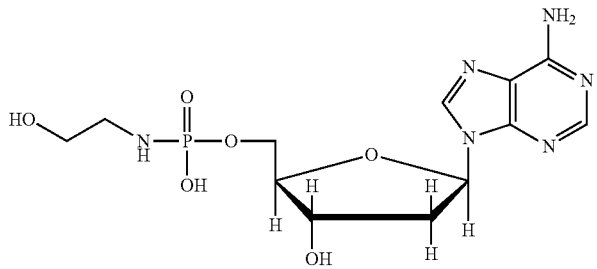
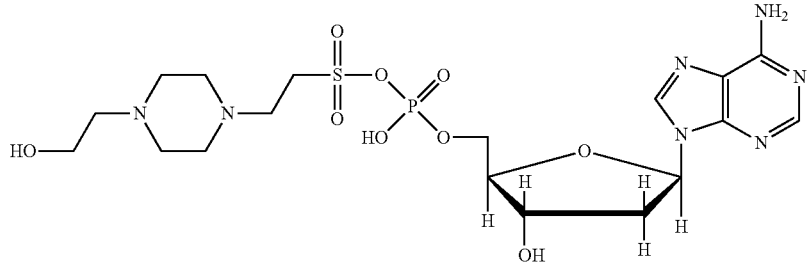

TABLE 1-continued
| Reagent | dNTP | Exemplary Nucleotide Analog |
|---|---|---|
| Glucose | dATP | 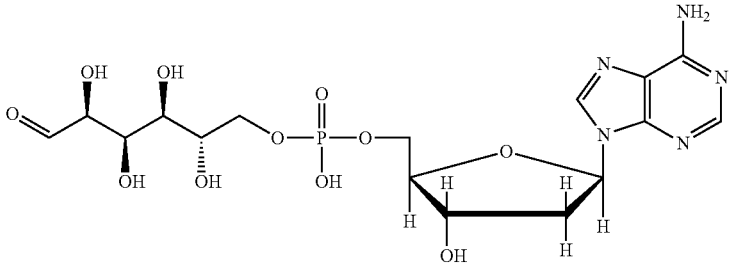 |
| Fructose | dATP | 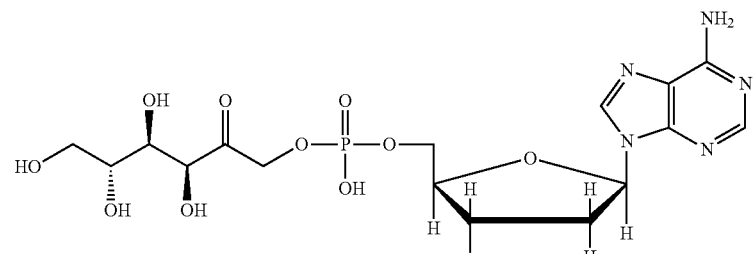 |
| Arabinose | dATP | 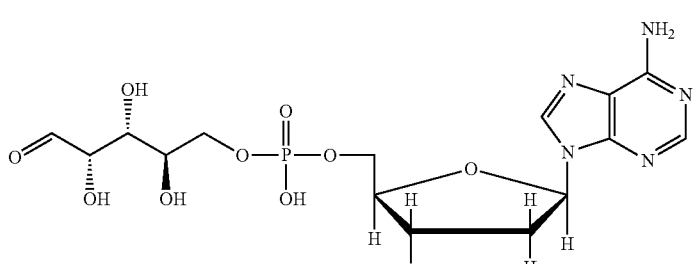 |
| Rhamnose | dATP | 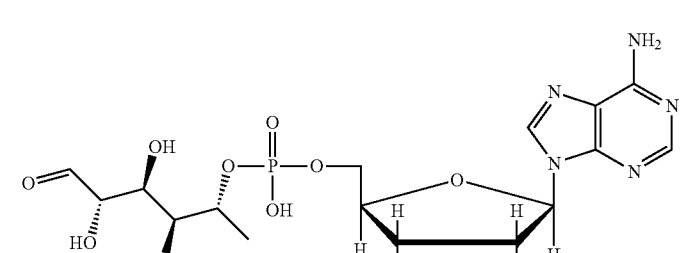 |
| Mannose | dATP | 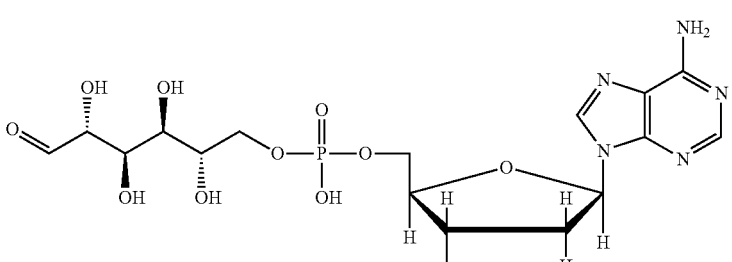 |

TABLE 1-continued

| Reagent | dNTP | Exemplary Nucleotide Analog |
|---|---|---|
| Xylose | dATP | |
| Galactose | dATP | |
| Lactose | dATP | |
| cellobiose | dATP | |
| Maltose | dATP | |

TABLE 1-continued
| Reagent | dNTP | Exemplary Nucleotide Analog |
|---|---|---|
| Raffinose | dATP | 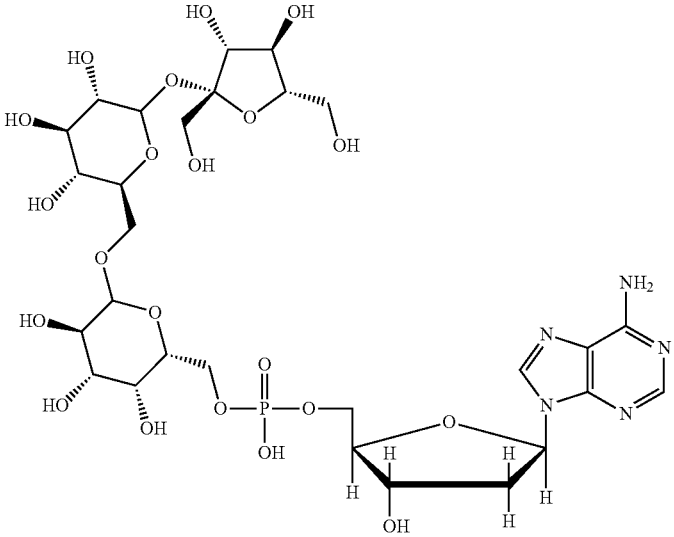 |
| Sorbitol | dATP | 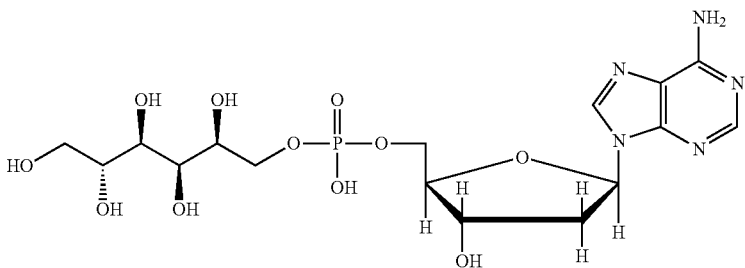 |
| Resorcinol | dATP | 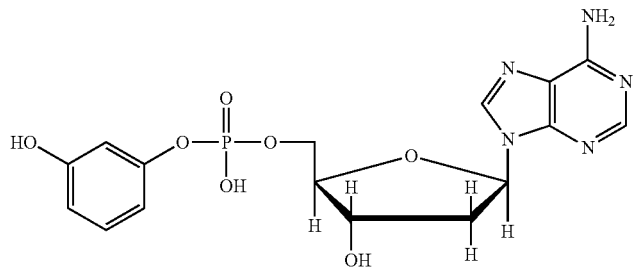 |
| Tetraethylene-glycol | dATP | 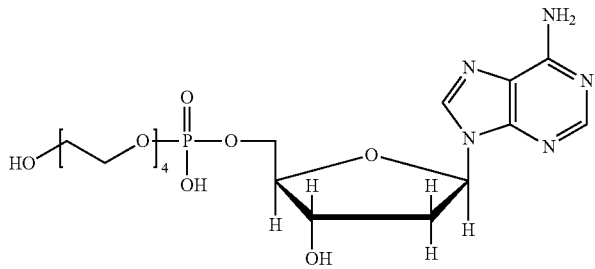 |

TABLE 1-continued

| Reagent | dNTP | Exemplary Nucleotide Analog |
|---|---|---|
| Inosine | dATP | 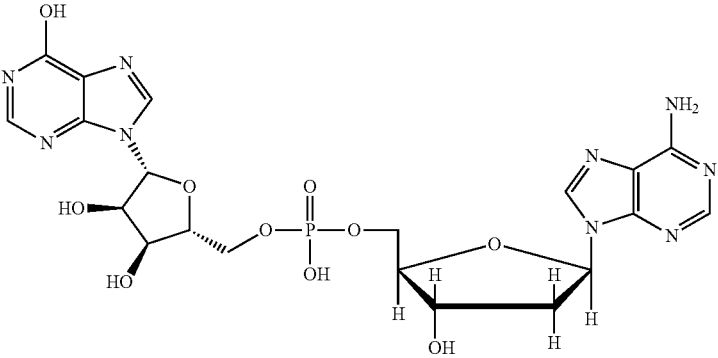 |
| Mannitol | dATP | 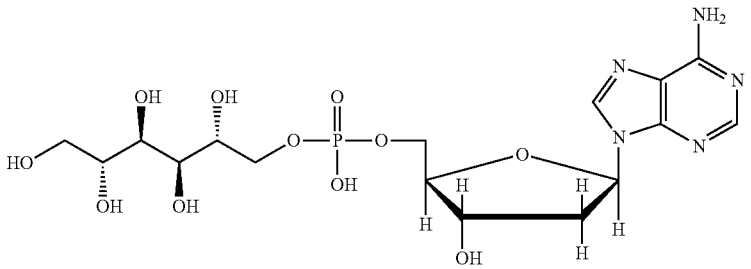 |
| Serine | dATP | 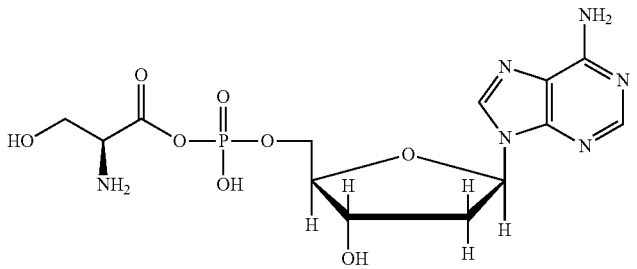 |
| Cysteine | dATP | 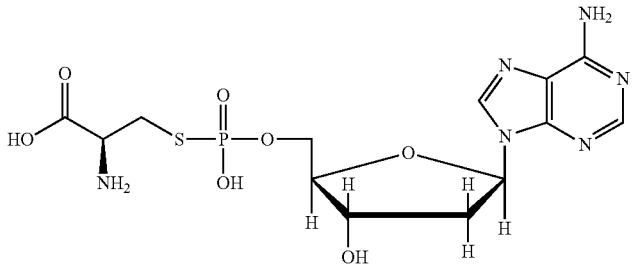 |

For analysis, aliquots of the resulting reaction mixture were subjected to ascending TLC in a solvent until the solvent front reached ~1 cm from the top of a PEI cellular plate strip (Brinkmann Instruments). PEI strips were air-dried and subjected to autoradiography or phosphorimaging. Aliquots of the reaction mixture also were subjected to 8 M urea-20% PAGE separation for 2 h to 3 h at 300 V in 1× Tris-borate-EDTA. Gels were usually subjected to autoradiography wet. Frozen gels were wrapped in paper towels to prevent moisture condensation.

Larger Scale Production of Nucleotide Analogs.

The process described for small-scale batches is scalable to larger batches by using proportionate amounts of compounds. As an alternate to the small-scale batches described above, larger scale batches were prepared. Here, reaction mixtures having a total volume of 0.25 ml (>10× the volume of the small-scale batch) and containing 40 mM of a reagent from Table 1, 10 mM magnesium acetate, 80 µM dATP, 50 µg/ml BSA, and 5.84 µM p41 subunit (containing 0.64 M glycerol following dilution in the glycerol diluent described above) were incubated for 30 min at 70° C. Incubation with the p41 subunit and TLC analysis on PEI plates showed greater than 60% conversion of starting material (i.e., the reagent and dNTP) into nucleotide analog products (dNMP derivatives). Experiments were also performed using heavy isotopes incorporated in dNTP, but the presence of a heavy isotope did not alter the utilization of dNTP in the reaction.

Samples from reaction mixtures were analyzed using a capillary reverse phase liquid chromatography system coupled to an Orbitrap Discovery mass spectrometer in negative mode. Negative mode nanospray mode was set to −1.5 kV, and chromatographic flow rate was <20 nl/min. Fragmentation was achieved using high collision dissociation at 45% energy. Isotope-labeled samples were run both individually and combined. By analyzing the mass difference between heavy and light fragmentation pattern, the identity of each fragmentation peak was established.

Preparation of [γ-$^{32}$P]dATP. Reaction mixtures (120 µl) containing optionally 50 mM Tris-HCl at pH 8.0, 6 mM magnesium acetate, 2.5 mM cysteine, 10 mM 3-phosphoglycerate, 40 µM NAD, 0.2 mM dATP, 2 µg of 3-phosphoglycerate kinase, 40 µg of 3-phosphoglyceraldehyde dehydrogenase, and $^{32}$P (7.68×10$^7$ cpm) were incubated for 60 min at 37° C. Mixtures were treated with 100 µl of 10% charcoal slurry (previously washed with 1 N HCl and H$_2$O until neutral), 50 µl of 1 N HCl, and 50 µl of 10 mM sodium phosphate, pH 7.5. Charcoal was collected by centrifugation, washed three times with 0.3 ml of 10 mM sodium phosphate buffer, pH 7.5, and then washed twice with 0.3 ml of H$_2$O. Charcoal adsorbed material was eluted with three washes of 100 µl of H$_2$O-ethanol-concentrated NH$_4$OH mixture (1:1, 0.08), which were pooled and concentrated in vacuo. The dried material was suspended in 0.2 ml of 1×TE and centrifuged at 20,000 rpm in an Eppendorf centrifuge at 4° C. Approximately 45% of the input $^{32}$P was recovered in the eluted material. Assuming quantitative incorporation of $^{32}$P into dATP, [γ-$^{32}$P]dATP would be expected to contain 3200 cpm/pmol. The 32P recovery (3.5×107 cpm) suggested that ~11 nmol of dATP was isolated. TLC on PEI cellular plates in 0.5 M ammonium formate, pH 3.5, indicated that the preparation contained 94% [γ-$^{32}$P]dATP and 6% $^{32}$P$_i$ (phosphate). Incubation with excess glucose and hexokinase resulted in the transfer of the $^{32}$P present in [γ-$^{32}$P]dATP quantitatively to glucose 6-phosphate.

Preparation of [βγ-$^{32}$P]dATP.

Reaction mixtures (120 µl) containing 20 mM Tris-HCl, pH 8.0, 10 mM magnesium acetate, 0.4 mM cysteine, 2 mM 3-phosphoglycerate, 18 nM NAD, $^{32}$Pi (6×10$^8$ cpm), 0.25 mM dATP, 25 nM dAMP, 20 µg of 3-phosphoglycerate kinase, 30 µg of 3-phospho glyceraldehyde dehydrogenase, and 5 µg of muscle myokinase were incubated at 37° C. for 60 min. Following incubation, 100 µl of 20% charcoal and 220 µl of 1 N HCl were added. After 20 min on ice, the mixture was centrifuged, washed four times with 0.4 ml of 5 mM sodium phosphate buffer, pH 7.5, and then washed once with 0.5 ml of H2O. The adsorbed material was eluted with a freshly prepared mixture of H2O-ethanol-NH4OH (400 µL, six times).

The washings were combined, vacuum-dried, and suspended in 0.2 ml of 1×TE. Approximately 40% of the $^{32}$P$_i$ added to the reaction was recovered (2.36×10$^8$ cpm). Based on the level of dATP added and assuming complete utilization of the $^{32}$P$_i$, the isolated dATP had a specific activity of ~20,000 cpm/pmol with $^{32}$P distributed equally between the β and γ phosphate residues of dATP. TLC on PEI plates in 0.5 M ammonium formate (pH 3.5) indicated that the preparation contained 92% [$^{32}$P]dATP and 8% [$^{32}$P]dADP; treatment with hexokinase and glucose resulted in the quantitative disappearance of [γ-$^{32}$P]dATP and formation of equally labeled dADP and glucose 6-phosphate, in keeping with the equal distribution of $^{32}$P between the β and γ phosphate residues of dATP.

Example 1

Tris-dAMP and Glycerol Nucleotide Analogs

Tris-dAMP (both O-Tris-dAMP and N-Tris-dAMP) and glycerol-dAMP were prepared using the small-scale preparatory method as described above by including both Tris and glycerol in the reaction mixture with each reagent at a concentration of 40 mM. Labelled [α-$^{32}$P]dATP (4250 cpm/pmol) and [γ-$^{32}$P]dATP (2430 cpm/pmol) were used as the dNTP at a concentration of 100 µM in the reactions. Additionally, p41, p46, p41/p46 complex, p41(m), and p41(m)/p46 complex at a concentration of 0.5 µM (or at increased concentration of 1.25 µM) were used as the enzyme in separate experiments. The resulting *T. kodakaraensis* primase preparations were incubated for 30 min at 70° C. Aliquots (5 µL) from reactions were separated by urea-PAGE and subjected to autoradiography. As shown by the urea-PAGE photo in FIG. 1, [α-$^{32}$P]dATP forms Tris-dAMP and glycerol-dAMP, but [γ-$^{32}$P]dATP does not. Moreover, no nucleotide analog (Tris-dAMP or glycerol-dAMP) was formed when the mutant (i.e., p41(m) or p41(m)/p46) form of the enzyme was used. Further, p46 alone did not produce a nucleotide analog. However, p41 the p41/p46 complex formed Tris-dAMP and glycerol-dAMP. When the amount of the p41/p46 complex was increased from 0.5 µM to 1.25 µM, the amount of the Tris-dAMP and glycerol-dAMP products increased.

Figure 2:
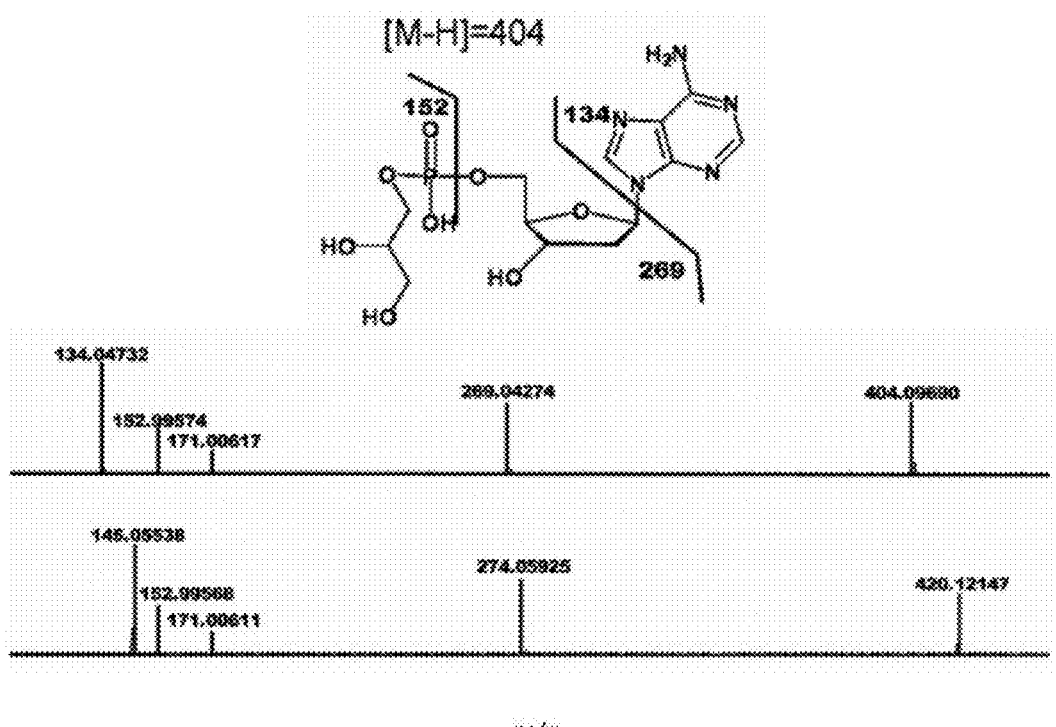
FIG. 2 shows a mass spectrum for a glycerol-dAMP nucleotide analog.

The nucleotide analogs were isolated and subjected to mass spectrometric analysis as described above. FIG. 2 shows the mass spectrum for glycerol-dAMP obtained from two different experiments. The upper spectrum in FIG. 2 was produced from the glycerol-dAMP product using [$^{12}$C, $^{14}$N] dATP as the dNPT in the reaction mixture, and the lower spectrum in FIG. 2 was produced from the glycerol-dAMP product using [$^{13}$C, $^{15}$N]dATP as the dNPT in the reaction mixture.

Figure 3:
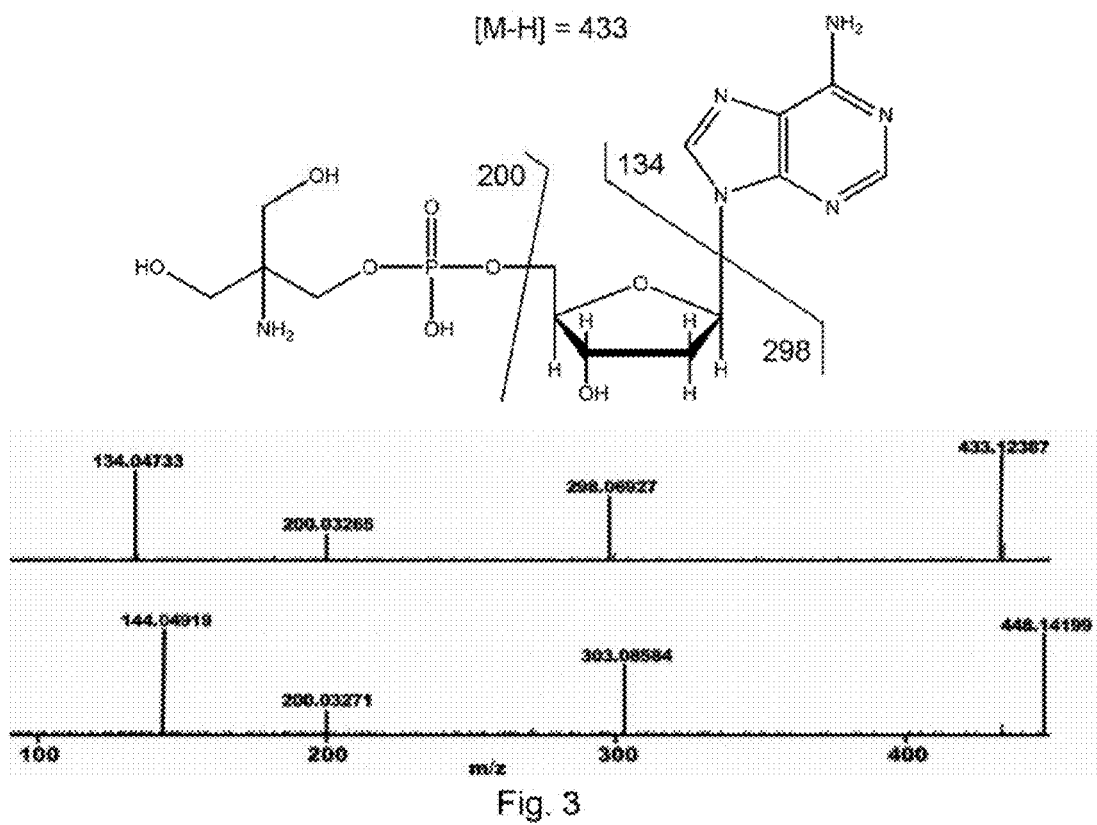
FIG. 3 shows a mass spectrum for a Tris-dAMP nucleotide analog.

Similarly, FIG. 3 shows the mass spectrum for Tris-dAMP obtained from two different experiments. The upper spectrum in FIG. 3 was produced from the Tris-dAMP product using [$^{12}$C, $^{14}$N]dATP as the dNPT in the reaction mixture, and the lower spectrum in FIG. 3 was produced form the Tris-dAMP product using [$^{13}$C, $^{15}$N]dATP as the dNPT in the reaction mixture.

The fragmentation pattern of the respective nucleotide analog is shown above the spectra in FIGS. 2 and 3.

Figure 5:
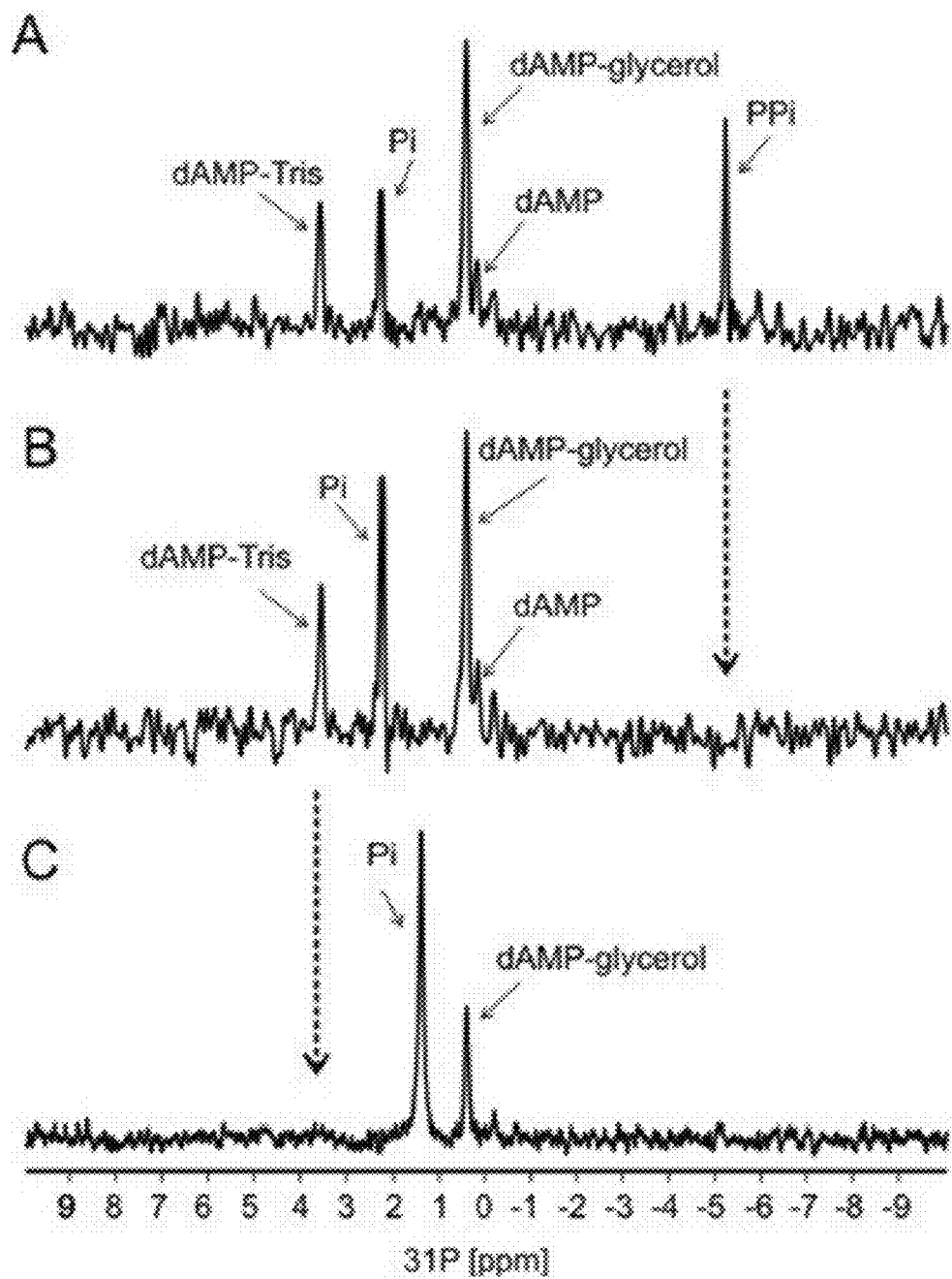
FIG. 5 shows NMR spectra for various experiments involving labelled dATP.

Nucleotide analogs formed in the reaction also were analyzed by $^{31}$P NMR to confirm the nature of the phosphorylated products (e.g., nucleotide analogs) formed in the reaction. Here, the nucleotide analogs prepared with [$^{12}$C, $^{14}$N]dATP, [$^{13}$C,$^{15}$N]dATP, and d-Tris (deuterated Tris) were analyzed. As shown in FIG. 5, initial one-dimensional $^{31}$P spectra of the reaction mixture (FIG. 5A) containing [$^{13}$C, $^{15}$N]ATP, glycerol, and d-Tris had four dominant $^{31}$P resonance peaks that were assigned to phosphorus atoms contained in the Tris-dAMP and glycerol-dAMP products, as well as signals from P$_i$ and PP$_i$. In addition, a minor peak was observed and assigned to dAMP. No signals were observed from the starting substrate dATP, indicating that the input dATP was converted quantitatively to products.

With reference to FIG. 5B, after a few days at room temperature, the one-dimensional $^{31}$P spectra of the same reaction mixture had only three dominant $^{31}$P peaks that were assigned to Tris-dAMP, glycerol-dAMP, dAMP, and P$_i$. In this spectrum, the PP$_i$ signal was absent, and the peak assigned to P$_i$ increased as compared to the spectrum in FIG. 5A, indicating that PP$_i$ was hydrolyzed to P$_i$. The changing amplitude of the P$_i$ and PP$_i$ resonance peaks was due to the presence of inorganic pyrophosphatase in *T. kodakaraensis* primase preparations.

To confirm the formation of Tris-dAMP, the d-Tris was replaced by glycerol, and glycine in the reaction mixture, and a one-dimensional $^{31}$P spectrum of the reaction mixture that also included [$^{13}$C,$^{15}$N]ATP was analyzed. As shown in FIG. 5C, $^{31}$P resonances assigned to glycerol-dAMP-glycerol and P$_i$ were observed, and the $^{31}$P resonance signal assigned to Tris-dAMP product was absent in the spectrum. For both the Tris-dAMP and the glycerol-dAMP, the $^{31}$P NMR confirmed that these nucleotide analogs formed via a 5' α-phosphorus linkage to dAMP. In addition. $^1$H NMR indicated no chemical modifications occurred to the base or sugar of the dAMP moiety in these products.

Example 2

Isotope Substitution of dNTP

Figure 4:
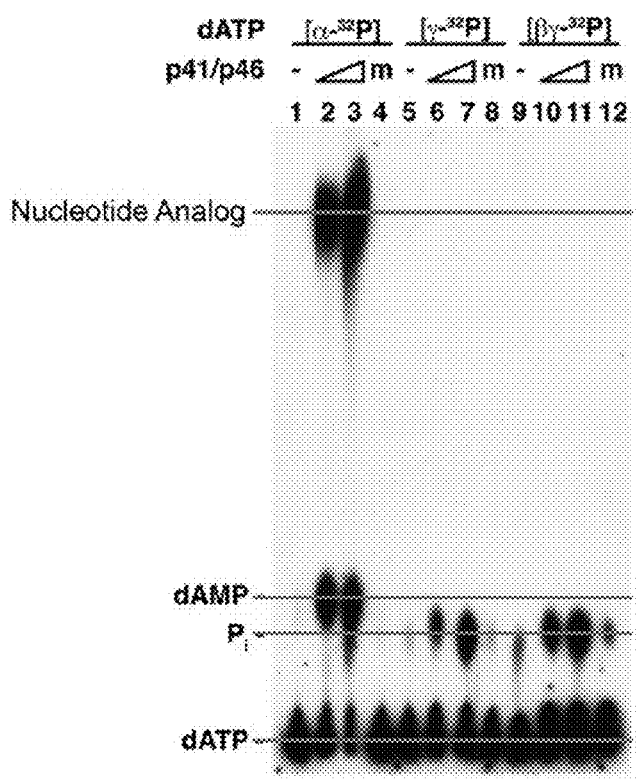
FIG. 4 shows a developed thin layer chromatography plate indicating production of various reaction products for various experiments.

Tris-dAMP (both O-Tris-dAMP and N-Tris-dAMP) and glycerol-dAMP were prepared using the small-scale preparatory method as described above by including both Tris and glycerol in the reaction mixture with each reagent at a concentration of 40 mM. Labelled [α-$^{32}$P]dATP (4×10$^3$ cpm/pmol), [γ-$^{32}$P]dATP (3.4×10$^3$ cpm/pmol), and [βγ-$^{32}$P] (5.1×10$^3$ cpm/pmol) were used as the dNTP in the reactions. Here, p41/p46 complex (at 0.25 μM or 0.75 μM) and p41(m)/p46 complex (0.75 M) were used as the enzyme in separate experiments. The resulting *T. kodakaraensis* primase preparations were incubated for 30 min at 70° C. Aliquots (1 μL) from reactions were separated by TLC on a PET plate developed in 0.3 M LiCl. As shown by the photo of the PEI plate in FIG. 4, [α-$^{32}$P]dATP forms Tris-dAMP and glycerol-dAMP in the presence of p41/p46 complex, but neither [γ-$^{32}$P]dATP nor [βγ-$^{32}$P] forms a nucleotide analog. Instead, with [γ-$^{32}$P]dATP and [βγ-$^{32}$P]dATP as the dNTP in the reaction mixture, phosphate P$_i$ is present on the developed PET plate. Furthermore, the mutant p41(m)/p46 complex also does not form a nucleotide complex.

Thus, nucleotide analog formation occurred for p41 and p41/p46 but not for p46 alone or for p41(m)/p46. Moreover, as the concentration of [α-$^{32}$P]dATP increased in the reaction mixture, the amount of nucleotide analog increased.

Figure 6:
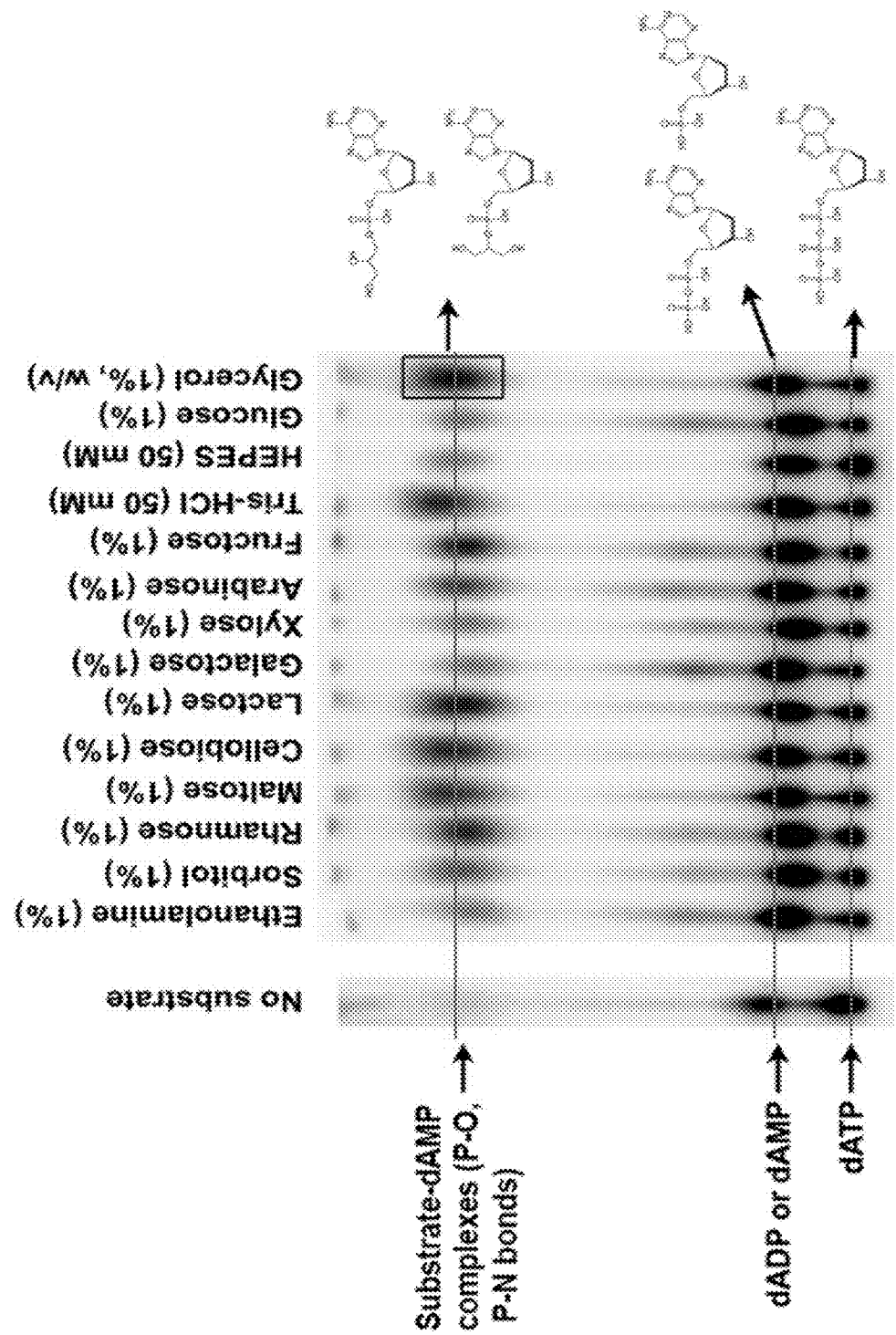
FIG. 6 shows developed images for several nucleotide analogs.

With reference to FIG. 6, a developed TLC plate is shown displaying bands for nucleotide analogs formed from reagents in Table 1.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity). The conjunction "or" is used to link objects of a list or alternatives and is not disjunctive; rather the elements can be used separately or can be combined together under appropriate circumstances.

What is claimed is:

1. A process for making a nucleotide analog, the process comprising:

combining a first substrate comprising a compound of formula 1

$$P^3—P^2—P^1-L-Q \quad \text{Formula 1}$$

with a second substrate comprising a compound of formula 27

$$R-Q^1-R^5 \quad \text{Formula 27}$$

to form a substrate composition;

contacting the substrate composition with an enzyme; and catalyzing, with the enzyme, formation of the nucleotide analog of formula 28 from the first substrate and the second substrate $$R-Q^1-P^1-L-Q \quad \text{Formula 28}$$

wherein the enzyme comprises an amino acid sequence having at least 90% identity to the amino acid sequence consisting of (SEQ ID NO. 1)
MSKLLREVTPEERRLYYSGEWDAKKLPEFIVESIERREFGFDHTGEGPSD

RKNAFSDVRDLEDYIRATAPYAAYSSVAFYRNPQEMEGWLGAELVFDIDA

KDLPLRRCQNEHPSGQVCPICLEDAKELARDTLIILKEDFGFENIHVVYS

GRGYHIRVIDEWALKLDSKARERILSYVSAAEEVTFDDIQKRYIMLSSGY

FRVFRLRFGYFIQRINENHLKNIGLKRSTAEKLLDEKTRQDIVEKFVNKG

LLAAFPEGVGYRTLLRLFGLSTTFSKAYFDGRVTVDLKRILRLPSTLHSK

VGLVATYIGSDEKRLEKFDPFKDAVPEFRKEEVQKAYQEWKELHEG;

L is a linker comprising a structure of formula 3, formula 6, formula 7, formula 8, formula 9, formula 10, formula 11, or formula 12,

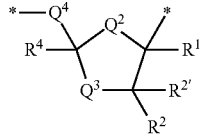

Formula 3

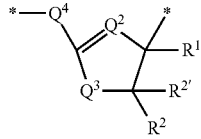

Formula 6

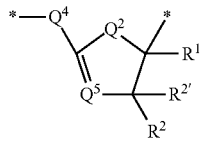

Formula 7

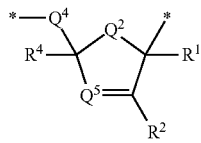

Formula 8

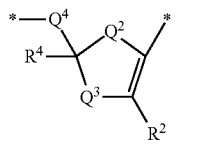

Formula 9

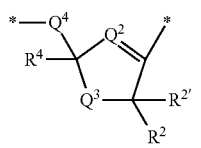

Formula 10

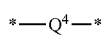

Formula 11

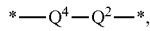

Formula 12 wherein * is a point of attachment;
  $Q^2$ and $Q^3$ are independently O, S, Se, NR, $CR_2$, or $C=CR_2$;
  $Q^4$ is O, S, NR, $CR_2$, $CR_2CR_2$, $CR_2O$, $CR_2OCR_2$, $CR_2S$, $CR_2SCR_2$, $CR_2NR$, $CR_2NRCR_2$, alkenylene, alkylene, alkyleneoxy, alkynylene, amide, aralkylene, arylene, aryleneoxy, cycloalkylene, fluoroalkylene, heteroaralkylene, heteroarylene, heterocycloalkylene, or a single bond;
  $Q^5$ is N or CR;
  $R^1$, $R^2$, $R^{2'}$, and $R^4$ are independently R, OR, SR, $NR_2$, NROR, $NRNR_2$, $N_3$, $NO_2$, CHO, CN, $C(=O)NH_2$, or $C(=O)OR$; alternatively, $R^2$ and $R^{2'}$ together are =O, =S, =N—R, or =$CR_2$; and
  R is independently H, F, Cl, Br, I, OH, SH, NHOH, $NHNH_2$, CHO, $C(=O)OH$, alkenyl, alkeneneamine, alkoxy, alkyl, alkyleneamine, alkynyl, amine, amino, aralkyl, aralkyloxy, aralkyloxy, aryl, aryleneamine, aryloxy, carbocyclic, carboxylic acid group or salt, cycloalkyl, cycloalkyloxy, haloalkyl, heteroaralkyl, heteroaryl, or heterocycloalkyl;

Q is a base comprising a structure of formula 13, formula 14, formula 15, or formula 16,

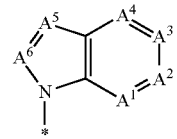

Formula 13

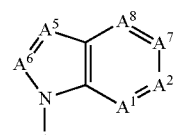

Formula 14

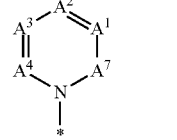

Formula 15

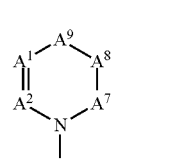

Formula 16 wherein $A^1$, $A^2$, $A^3$, $A^4$, $A^5$, and $A^6$ are independently N, C—$R^1$;
  $A^7$, $A^8$, $A^9$ is independently N—$R^1$, $C(R^1)_2$, C=O, C=C—$(R^1)_2$, C=N—$R^1$; and
  $R^1$ is as defined above;
$P^1$ and $P^2$ are respectively a first phosphate group and a second phosphate group independently having a structure of formula 25, and $P^3$ is a third phosphate group having a structure of formula 26,

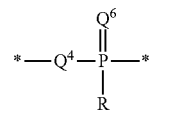

Formula 25

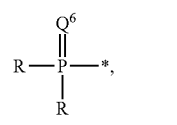

Formula 26 wherein $Q^6$ is O, NR, or S; and $Q^4$, R, and * are as defined above;
$Q^1$ is O, S, Se, NR, $CR_2$, or $C=CR_2$, cycloalkenylene, cycloalkylene, heterocycloalkenylene, heterocycloalkylene; and
$R^5$ is H, F, Cl, Br, I, OH, SH, NHOH, $NHNH_2$, CHO, alkenyleneamine, alkyleneamine, amine, aryleneamine, or carboxylic acid group or salt.

2. The method of claim 1, wherein the base Q comprises

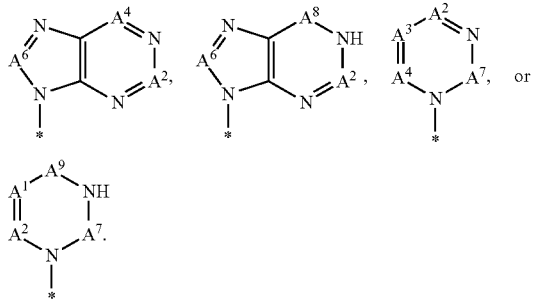

3. The method of claim 2, wherein the base Q comprises

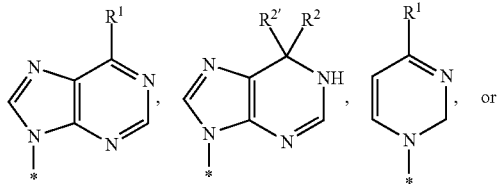

4. The method of claim 1 wherein the linker L comprises

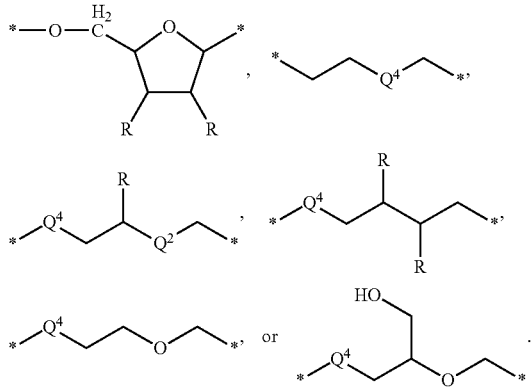

5. The method of claim 4, wherein the linker L is

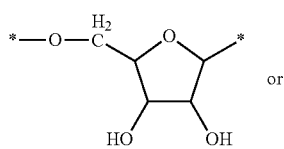

or

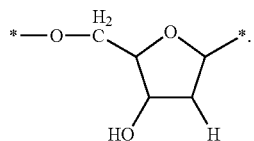

6. The method of claim 4, wherein P1 and P2 independently have a structure of formula 31, and P3 has a structure of formula 32

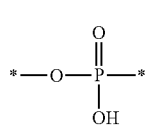

Formula 31

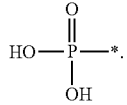

Formula 32

7. The method of claim 1, wherein the second substrate is an alcohol, an amino acid, a chromophore, a fatty acid, a sugar, or a combination comprising at least one of the foregoing.

8. The method of claim 1, wherein the second substrate is 2-(N-morpholine) ethanesulfonic acid (MES), N-(2-acetamido) iminodiacetic acid (ADA), piperazine-N,N'-bis(2-ethanesulfonic acid) (PIPES), N-(2-acetamido)-2-aminoethanesulfonic acid (ACES), (2-aminoethyl)-trimethyl ammonium chloride hydrochloride (Cholamine), N,N-bis(2-hydroxy-ethyl)-2-aminoethane sulfonic acid (TES), 2-[4-(2-hydroxyethyl)-1-piperazinyl]ethanesulfonic acid (HEPES), tris(hydroxymethyl) aminomethane (TRIS), N-tris(hydroxyl-methyl)methylglycine (Tricine), N,N-bis(2-hydroxyethyl)-glycine (Bicine), 2-(N-cyclohexylamino) ethane-sulfonic acid (CHES), acetic acid, phosphoric acid, citric acid, ethylenediaminetetraacetic acid, a salt thereof, or a combination comprising at least one of the foregoing.

9. The method of claim 1, wherein the nucleotide analog comprises

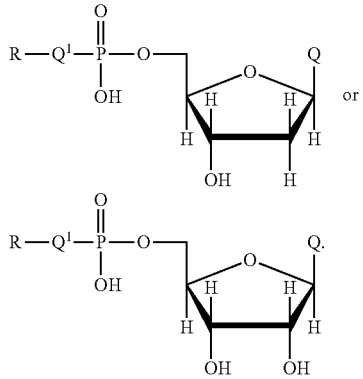

10. The method of claim 9, wherein the nucleotide analog is

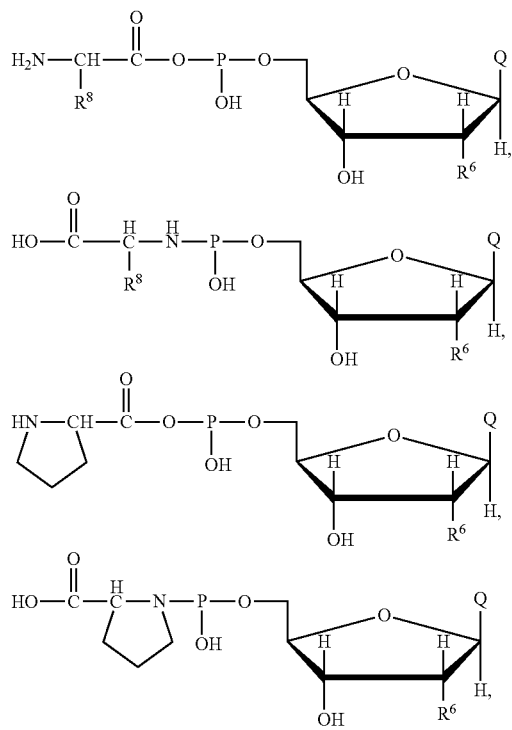

wherein R⁸ is a functional group selected from H, CH₃,

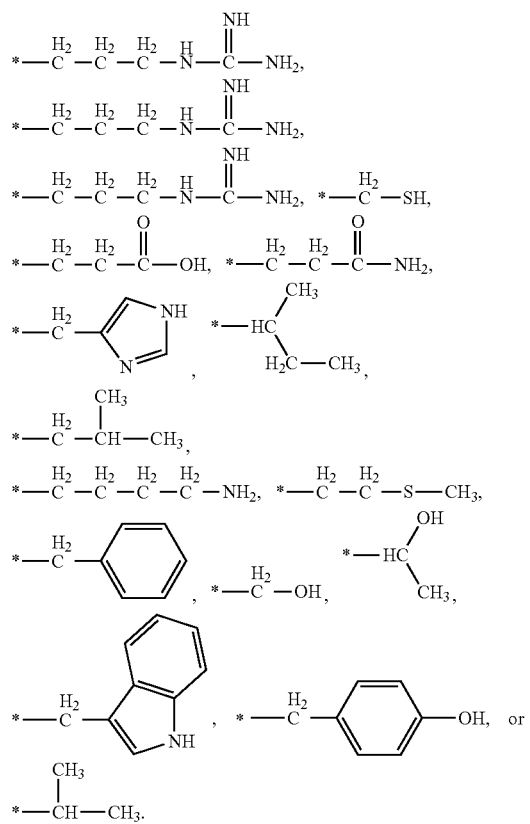

11. The method of claim 1, wherein the nucleotide analog is Tris-dAMP having the structure

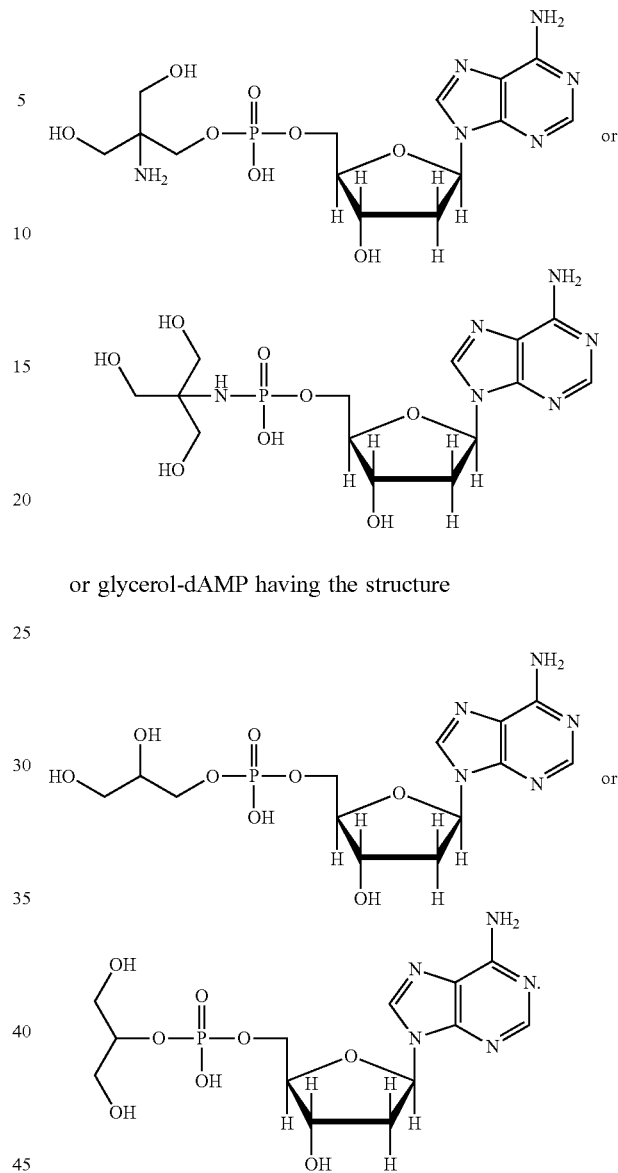

or glycerol-dAMP having the structure

12. The method of claim 1, wherein the enzyme is a single subunit or a complex comprising a small subunit and a large subunit arranged in a complex.

13. The method of claim 1, wherein the substrate composition further comprises an alkaline earth metal cation, a transition metal cation, or a combination comprising at least one of the foregoing in an amount effective so that the enzyme has activity with respect to catalyzing formation of the nucleotide analog.

14. The method of claim 1, further comprising immobilizing the first substrate, the second substrate, the enzyme, or a combination comprising at least one of the foregoing on a solid phase support during formation of the nucleotide analog.

15. The method of claim 1, wherein catalyzing formation of the nucleotide analog is conducted at a temperature from 4° C. to 130° C.

16. The method of claim 1, wherein the enzyme is has activity with respect to catalyzing formation of the nucleotide analog in a pH range from 1 to 14, inclusive of an entirety of the pH range.

17. A composition comprising:
a first substrate comprising a compound of formula 29

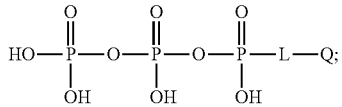

Formula 29 a second substrate comprising a compound of formula 27

R-Q$^1$-R$^5$;   Formula 27;

an enzyme comprising an amino acid sequence having at least 90% identity to the amino acid sequence consisting of (SEQ ID NO. 1)
MSKLLREVTPEERRLYYSGEWDAKKLPEFIVESIERREFGFDHTGEGPSD

RKNAFSDVRDLEDYIRATAPYAAYSSVAFYRNPQEMEGWLGAELVFDIDA

KDLPLRRCQNEHPSGQVCPICLEDAKELARDTLIILKEDFGFENIHVVYS

GRGYHIRVIDEWALKLDSKARERILSYVSAAEEVTFDDIQKRYIMLSSGY

FRVFRLRFGYFIQRINENHLKNIGLKRSTAEKLLDEKTRQDIVEKFVNKG

LLAAFPEGVGYRTLLRLFGLSTTFSKAYFDGRVTVDLKRILRLPSTLHSK

VGLVATYIGSDEKRLEKFDPFKDAVPEFRKEEVQKAYQEWKELHEG;

and
a nucleotide analog formed by the enzyme from the first substrate and the second substrate, the nucleotide analog comprising a compound of formula 30

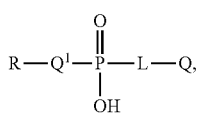

Formula 30 wherein L is a linker comprising a structure of formula 3, formula 6, formula 7, formula 8, formula 9, formula 10, formula 11, or formula 12

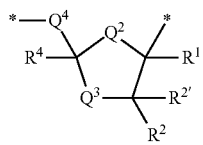

Formula 3

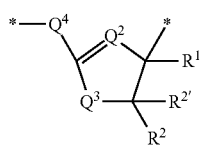

Formula 6

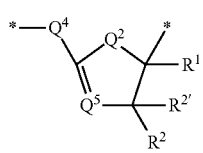

Formula 7

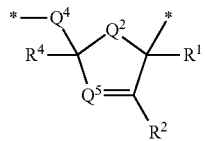

Formula 8

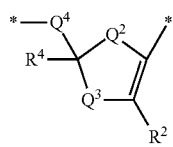

Formula 9

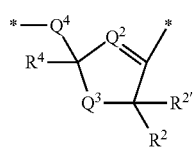

Formula 10

Formula 11

Formula 12 wherein * is a point of attachment;
Q$^2$ and Q$^3$ are independently O, S, Se, NR, CR$_2$, or C=CR$_2$;
Q$^4$ is O, S, NR, CR$_2$, CR$_2$CR$_2$, CR$_2$O, CR$_2$OCR$_2$, CR$_2$S, CR$_2$SCR$_2$, CR$_2$NR, CR$_2$NRCR$_2$, alkenylene, alkylene, alkyleneoxy, alkynylene, amide, aralkylene, arylene, aryleneoxy, cycloalkylene, fluoroalkylene, heteroaralkylene, heteroarylene, heterocycloalkylene, or a single bond;
Q$^5$ is N or CR;
R$^1$, R$^2$, R$^{2'}$, and R$^4$ are independently R, OR, SR, NR$_2$, NROR, NRNR$_2$, N$_3$, NO$_2$, CHO, CN, C(=O)NH$_2$, or C(=O)OR; alternatively, R$^2$ and R$^{2'}$ together are =O, =S, =N—R, or =CR$_2$; and
R is independently H, F, Cl, Br, I, OH, SH, NHOH, NHNH$_2$, CHO, C(=O)OH, alkenyl, alkenyleneamine, alkoxy, alkyl, alkyleneamine, alkynyl, amine, amino, aralkyl, aralkyloxy, aralkyloxy, aryl, aryleneamine, aryloxy, carbocyclic, carboxylic acid group or salt, cycloalkyl, cycloalkyloxy, haloalkyl, heteroaralkyl, heteroaryl, or heterocycloalkyl;
Q is a base comprising

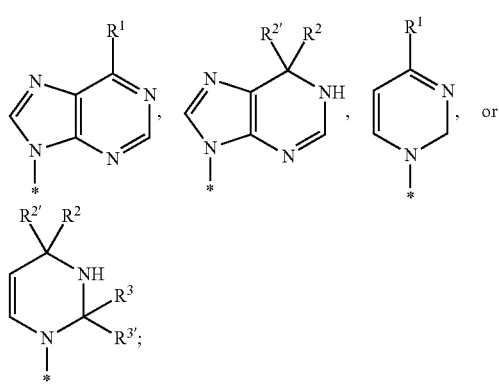

Q$^1$ is O, S, Se, NR, CR$_2$, or C=CR$_2$, cycloalkenylene, cycloalkylene, heterocycloalkenylene, heterocycloalkylene; and R[5] is H, F, Cl, Br, I, OH, SH, NHOH, NHNH$_2$, CHO, alkenyleneamine, alkyleneamine, amine, aryleneamine, or carboxylic acid group or salt.

18. The composition of claim 17, wherein the linker L is

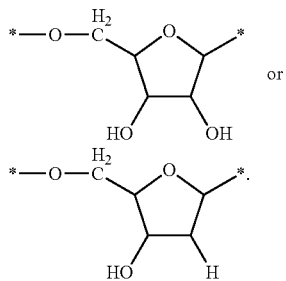

or

19. The composition of claim 18, wherein the second substrate is an alcohol, an amino acid, a chromophore, a fatty acid, a sugar, or a combination comprising at least one of the foregoing.

20. The composition of claim 19, wherein the nucleotide analog is

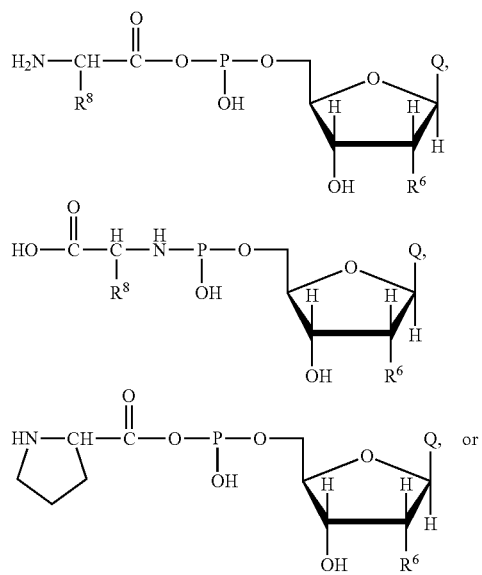

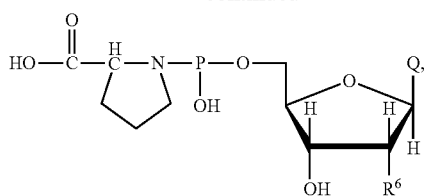

wherein R6 is H or OH;

R[8] is a functional group selected from H, CH$_3$,

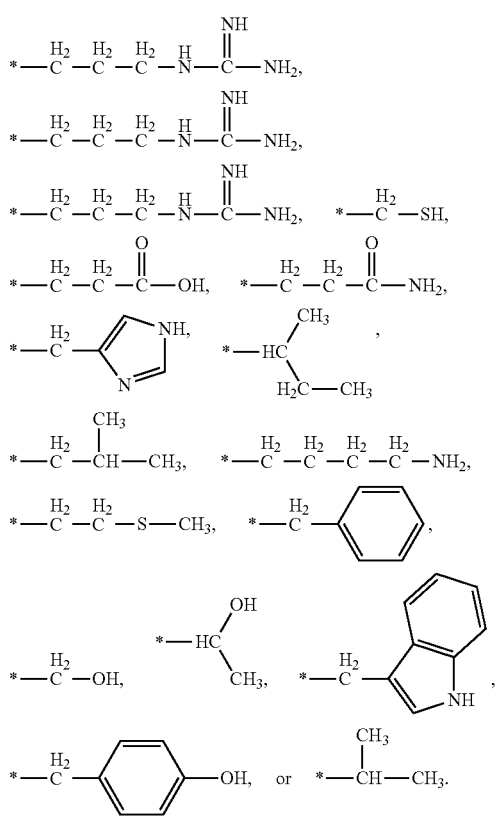

* * * * *

SEQUENCE LISTING

```
<160> NUMBER OF SEQ ID NOS: 2

<210> SEQ ID NO 1
<211> LENGTH: 346
<212> TYPE: PRT
<213> ORGANISM: Thermococcus kodakaraensis

<400> SEQUENCE: 1

Met Ser Lys Leu Leu Arg Glu Val Thr Pro Glu Glu Arg Arg Leu Tyr
1               5                   10                  15

Tyr Ser Gly Glu Trp Asp Ala Lys Lys Leu Pro Glu Phe Ile Val Glu
                20                  25                  30

Ser Ile Glu Arg Arg Glu Phe Gly Phe Asp His Thr Gly Glu Gly Pro
            35                  40                  45

Ser Asp Arg Lys Asn Ala Phe Ser Asp Val Arg Asp Leu Glu Asp Tyr
        50                  55                  60

Ile Arg Ala Thr Ala Pro Tyr Ala Ala Tyr Ser Ser Val Ala Phe Tyr
65                  70                  75                  80
```

```
Arg Asn Pro Gln Glu Met Glu Gly Trp Leu Gly Ala Glu Leu Val Phe
                 85                  90                  95

Asp Ile Asp Ala Lys Asp Leu Pro Leu Arg Arg Cys Gln Asn Glu His
            100                 105                 110

Pro Ser Gly Gln Val Cys Pro Ile Cys Leu Glu Asp Ala Lys Glu Leu
        115                 120                 125

Ala Arg Asp Thr Leu Ile Ile Leu Lys Glu Asp Phe Gly Phe Glu Asn
130                 135                 140

Ile His Val Val Tyr Ser Gly Arg Gly Tyr His Ile Arg Val Ile Asp
145                 150                 155                 160

Glu Trp Ala Leu Lys Leu Asp Ser Lys Ala Arg Glu Arg Ile Leu Ser
                165                 170                 175

Tyr Val Ser Ala Ala Glu Glu Val Thr Phe Asp Asp Ile Gln Lys Arg
            180                 185                 190

Tyr Ile Met Leu Ser Ser Gly Tyr Phe Arg Val Phe Arg Leu Arg Phe
        195                 200                 205

Gly Tyr Phe Ile Gln Arg Ile Asn Glu Asn His Leu Lys Asn Ile Gly
210                 215                 220

Leu Lys Arg Ser Thr Ala Glu Lys Leu Leu Asp Glu Lys Thr Arg Gln
225                 230                 235                 240

Asp Ile Val Glu Lys Phe Val Asn Lys Gly Leu Leu Ala Ala Phe Pro
                245                 250                 255

Glu Gly Val Gly Tyr Arg Thr Leu Leu Arg Leu Phe Gly Leu Ser Thr
            260                 265                 270

Thr Phe Ser Lys Ala Tyr Phe Asp Gly Arg Val Thr Val Asp Leu Lys
        275                 280                 285

Arg Ile Leu Arg Leu Pro Ser Thr Leu His Ser Lys Val Gly Leu Val
290                 295                 300

Ala Thr Tyr Ile Gly Ser Asp Glu Lys Arg Leu Glu Lys Phe Asp Pro
305                 310                 315                 320

Phe Lys Asp Ala Val Pro Glu Phe Arg Lys Glu Val Gln Lys Ala
                325                 330                 335

Tyr Gln Glu Trp Lys Glu Leu His Glu Gly
            340                 345

<210> SEQ ID NO 2
<211> LENGTH: 400
<212> TYPE: PRT
<213> ORGANISM: Thermococcus kodakaraensis

<400> SEQUENCE: 2

Met Leu Asp Pro Phe Gly Lys Arg Ala Glu Ser Leu Ile Arg Glu Glu
1               5                   10                  15

Phe Gly Asp Leu Leu Ala Leu Leu Glu Arg Val Pro Ser Ala Ile Ser
            20                  25                  30

Val Glu Glu Pro Ile Ser Leu Val Ser Trp Met Leu Glu Ser Glu Asn
        35                  40                  45

Pro Pro Gln Glu Leu Val Glu Val Asp Asn Leu Glu Glu Leu Arg Asp
    50                  55                  60

Leu Phe Lys Phe Tyr Ala Leu Leu Gly Ala Ala Ser Ile Ser Pro Tyr
65                  70                  75                  80

Gly Leu Glu Ala Glu Val Val Lys Arg Ala Thr Leu Arg Leu Tyr Ser
                85                  90                  95

Glu Arg Ile Lys Ala Ser Lys Asn Leu Ser Glu Thr Met Leu Pro Val
```

-continued

```
              100                 105                 110
Val Pro Val Gly Glu Asn Glu Ile Pro His Asn Asp Leu Asn Ile Leu
            115                 120                 125

Glu Arg Arg Met Asp Arg Asn Leu Ser Pro Glu Glu Lys Glu Lys Leu
130                 135                 140

Lys Ile Lys Tyr Lys Ile Pro Ile Lys Asp Leu Leu Asn Leu Trp Gly
145                 150                 155                 160

Ser Ser Leu Lys Glu Val Tyr Ile Arg Asn Gly Tyr Ala Tyr Leu Arg
                165                 170                 175

Trp Glu Thr Ala Leu Lys Met Trp Glu Lys Ala Phe Glu Lys Arg Phe
            180                 185                 190

Glu Arg Ala Val Asn Ile Leu Tyr Glu Tyr Arg Asp Glu Leu Pro Glu
        195                 200                 205

Phe Tyr His Arg Leu Arg Glu Lys Leu Glu Glu Ile Ala Glu Glu Tyr
    210                 215                 220

Phe Lys Glu Arg Gly Glu Met Phe Lys Gly Thr Ala Ser Pro Leu Arg
225                 230                 235                 240

Phe Asp Leu Phe Pro Pro Cys Val Lys Glu Ala Leu Lys Gly Val Pro
                245                 250                 255

Ala Gly Met Arg Asn Tyr Ala Ile Thr Val Leu Leu Thr Ser Phe Leu
            260                 265                 270

Ser Tyr Ala Arg Ile Cys Pro Asn Pro Pro Lys Lys Asp Val Arg Ile
        275                 280                 285

Lys Asp Cys Ile Asn Asp Leu Lys Ile Ile Glu Glu Glu Ile Leu Pro
    290                 295                 300

Val Ile Ile Glu Ala Gly Asn Arg Cys Lys Pro Pro Leu Phe Glu Asp
305                 310                 315                 320

Gln Pro His Glu Ile Lys Asn Ile Trp Tyr His Leu Gly Phe Gly Leu
                325                 330                 335

Thr Asp Ser Pro Thr Met Glu Asp Ser Gly Asn Ser Thr Trp Tyr Phe
            340                 345                 350

Pro Pro Asn Cys Asp Lys Ile Arg Ala Asn Ala Pro Gln Leu Cys Lys
        355                 360                 365

Pro Asp Lys Tyr Cys Arg Gly Ile Lys Asn Pro Leu Ser Tyr Tyr Leu
    370                 375                 380

Lys Arg Leu Tyr Leu Glu Gly Lys Lys Lys Glu Gly Glu Thr Ser Glu
385                 390                 395                 400
```